United States Patent
Bassett et al.

(10) Patent No.: US 11,992,627 B2
(45) Date of Patent: May 28, 2024

(54) ARTICLES COMPRISING MARKINGS AND RELATED METHODS

(71) Applicant: Access Vascular, Inc., Bedford, MA (US)

(72) Inventors: Michael Bassett, Hampton, NH (US); Daniel T. Donahue, Cambridge, MA (US); Matthew M. Mannarino, Burlington, MA (US)

(73) Assignee: Access Vascular, Inc., Billerica, MA (US)

( * ) Notice: Subject to any disclaimer, the term of this patent is extended or adjusted under 35 U.S.C. 154(b) by 267 days.

(21) Appl. No.: 17/361,025

(22) Filed: Jun. 28, 2021

(65) Prior Publication Data

US 2022/0088348 A1     Mar. 24, 2022

Related U.S. Application Data

(60) Provisional application No. 63/046,499, filed on Jun. 30, 2020.

(51) Int. Cl.
*A61M 25/01*     (2006.01)
*A61M 25/00*     (2006.01)

(52) U.S. Cl.
CPC . *A61M 25/0105* (2013.01); *A61M 2025/0008* (2013.01)

(58) Field of Classification Search
CPC ...... A61M 25/0105; A61M 2025/0008; A61M 25/0108; A61M 2025/0024; A61M 25/0074; A61M 25/0127; A61L 29/145
See application file for complete search history.

(56) References Cited

U.S. PATENT DOCUMENTS 3,220,960 A    11/1965   Vaclavkova
3,566,874 A     3/1971   Shepherd et al.
(Continued)

FOREIGN PATENT DOCUMENTS

CN     1579601 A     2/2005
CN   102580145 A     7/2012
(Continued)

OTHER PUBLICATIONS

U.S. Appl. No. 17/841,813, filed Jun. 16, 2022, Biggins et al.
(Continued)

*Primary Examiner* — Tiffany Legette
*Assistant Examiner* — William R Frehe
(74) *Attorney, Agent, or Firm* — Wolf, Greenfield & Sacks, P.C.

(57) ABSTRACT

Articles, such as catheters, comprising markings and associated methods are generally provided. The articles described herein may be configured to be exhibit one or more desirable properties. For instance, in some embodiments, an article comprises markings that are spaced from each other at known distances. Such markings may be employed to aid users of the article in measuring distances. As another example, an article may be configured to swell upon exposure to the fluid such that markings positioned thereon do not crack or delaminate. It is also possible for the article to be configured to swell upon exposure to the fluid in a known, predictable, and/or uniform manner. This swelling may cause the spacings between the markings to increase, and such increase may also be in a known, predictable, and/or uniform manner. When the fluid causing the article to swell is a bodily fluid, such as a fluid the article would be exposed to upon implantation into a patient, and the article swells such that the markings have a known spacing in the patient, the markings may advantageously be
(Continued)

employed to measure distances in the patient and/or the change in marking spacing may be employed to determine the swelling of the article in the patient.

15 Claims, 22 Drawing Sheets

(56) References Cited

U.S. PATENT DOCUMENTS

| | | | |
|---|---|---|---|
| 3,995,623 | A | 12/1976 | Blake et al. |
| 4,024,873 | A | 5/1977 | Antoshkiw et al. |
| 4,026,296 | A | 5/1977 | Stoy et al. |
| 4,073,733 | A | 2/1978 | Yamauchi et al. |
| 4,379,874 | A | 4/1983 | Stoy |
| 4,543,102 | A | 9/1985 | Defago et al. |
| 4,663,358 | A | 5/1987 | Hyon et al. |
| 4,943,618 | A | 7/1990 | Stoy et al. |
| 5,061,254 | A * | 10/1991 | Karakelle ............ A61L 29/06 604/530 |
| 5,225,120 | A | 7/1993 | Gravier et al. |
| 5,336,205 | A | 8/1994 | Zenzen et al. |
| 5,443,727 | A | 8/1995 | Gagnon |
| 5,449,382 | A | 9/1995 | Dayton |
| 5,508,036 | A | 4/1996 | Bakker et al. |
| 5,523,335 | A | 6/1996 | Whyzmuzis et al. |
| 5,578,075 | A | 11/1996 | Dayton |
| 5,601,538 | A | 2/1997 | Deem |
| 5,688,459 | A | 11/1997 | Mao et al. |
| 5,820,918 | A | 10/1998 | Ronan et al. |
| 5,928,279 | A | 7/1999 | Shannon et al. |
| 6,099,562 | A | 8/2000 | Ding et al. |
| 6,231,605 | B1 | 5/2001 | Ku |
| 6,271,278 | B1 | 8/2001 | Park et al. |
| 6,656,206 | B2 | 12/2003 | Corcoran et al. |
| 6,706,024 | B2 | 3/2004 | Modak et al. |
| 7,112,298 | B2 | 9/2006 | Kampa et al. |
| 7,329,695 | B2 | 2/2008 | Tucker et al. |
| 7,455,674 | B2 | 11/2008 | Rose |
| 7,485,670 | B2 | 2/2009 | Ruberti et al. |
| 7,619,009 | B2 | 11/2009 | Ruberti et al. |
| 7,631,760 | B2 | 12/2009 | Guelzow et al. |
| 7,745,532 | B2 | 6/2010 | Ruberti et al. |
| 7,845,670 | B2 | 12/2010 | Oberg |
| 8,017,139 | B2 | 9/2011 | Thomas et al. |
| 8,313,760 | B2 | 11/2012 | Hunter et al. |
| 8,470,035 | B2 | 6/2013 | Cruise et al. |
| 8,541,484 | B2 | 9/2013 | Choi et al. |
| 8,637,063 | B2 | 1/2014 | Kopesky et al. |
| 8,784,893 | B2 | 7/2014 | Daniloff et al. |
| 8,821,583 | B2 | 9/2014 | Myung et al. |
| 9,216,268 | B2 | 12/2015 | Liu et al. |
| 10,182,985 | B2 | 1/2019 | Bellinger et al. |
| 10,471,183 | B2 | 11/2019 | Biggins et al. |
| 10,485,898 | B2 | 11/2019 | Biggins et al. |
| 11,389,570 | B2 | 7/2022 | Biggins et al. |
| 11,577,008 | B2 | 2/2023 | Bassett et al. |
| 2001/0002411 | A1 | 5/2001 | Ronan et al. |
| 2002/0055710 | A1 | 5/2002 | Tuch |
| 2002/0138154 | A1 | 9/2002 | Li et al. |
| 2004/0092653 | A1 | 5/2004 | Ruberti et al. |
| 2004/0247867 | A1 | 12/2004 | Chaouk et al. |
| 2006/0240059 | A1 | 10/2006 | Bavaro et al. |
| 2006/0287650 | A1 | 12/2006 | Cao et al. |
| 2007/0129690 | A1 | 6/2007 | Rosenblatt et al. |
| 2008/0065010 | A1 | 3/2008 | Bavaro et al. |
| 2008/0075628 | A1 | 3/2008 | Judd et al. |
| 2008/0160062 | A1 | 7/2008 | Richards et al. |
| 2008/0208347 | A1 | 8/2008 | Muratoglu et al. |
| 2009/0010983 | A1 | 1/2009 | Melvik et al. |
| 2009/0075267 | A1 | 3/2009 | Siena et al. |
| 2009/0076495 | A2 | 3/2009 | Dando et al. |
| 2010/0087788 | A1 | 4/2010 | Rosenblatt et al. |
| 2010/0105801 | A1 | 4/2010 | Choi |
| 2010/0106103 | A1 * | 4/2010 | Ziebol ............ A61M 25/0105 604/265 |
| 2010/0145286 | A1 | 6/2010 | Zhang et al. |
| 2010/0152708 | A1 | 6/2010 | Li et al. |
| 2010/0204800 | A1 | 8/2010 | Thomas et al. |
| 2010/0210752 | A1 | 8/2010 | Muratoglu et al. |
| 2010/0234815 | A1 | 9/2010 | Do et al. |
| 2011/0000846 | A1 | 1/2011 | Ishizuka et al. |
| 2011/0027181 | A1 | 2/2011 | Amodei et al. |
| 2011/0091515 | A1 | 4/2011 | Zilberman et al. |
| 2011/0190683 | A1 * | 8/2011 | Gellman ........... A61M 25/0023 606/191 |
| 2011/0244010 | A1 | 10/2011 | Doshi |
| 2013/0046346 | A1 | 2/2013 | Thorwarth et al. |
| 2013/0338431 | A1 | 12/2013 | Shalon et al. |
| 2014/0045398 | A1 | 2/2014 | Zhang et al. |
| 2014/0058251 | A1 | 2/2014 | Stigall et al. |
| 2014/0178446 | A1 | 6/2014 | Zhu et al. |
| 2014/0287179 | A1 | 9/2014 | Kamioka et al. |
| 2016/0015863 | A1 | 1/2016 | Gupta et al. |
| 2016/0136389 | A1 * | 5/2016 | Christian .......... A61M 25/0043 604/523 |
| 2017/0143952 | A1 * | 5/2017 | Siess ................... A61M 60/268 |
| 2017/0173219 | A1 | 6/2017 | Biggins et al. |
| 2017/0182223 | A1 | 6/2017 | Biggins et al. |
| 2017/0340867 | A1 * | 11/2017 | Accisano, III ........ A61M 29/00 |
| 2018/0200185 | A1 | 7/2018 | Labib et al. |
| 2018/0250116 | A1 | 9/2018 | Mourhatch et al. |
| 2018/0369454 | A1 | 12/2018 | Mannarino et al. |
| 2019/0167942 | A1 | 6/2019 | Schonfeldt |
| 2020/0093965 | A1 | 3/2020 | Biggins et al. |
| 2020/0230295 | A1 | 7/2020 | Mannarino et al. |
| 2021/0069468 | A1 * | 3/2021 | Keating ............ A61B 17/221 |
| 2021/0275774 | A1 | 9/2021 | Doherty et al. |
| 2022/0378984 | A1 | 12/2022 | Biggins et al. |
| 2023/0256141 | A1 | 8/2023 | Bassett et al. |

FOREIGN PATENT DOCUMENTS

| | | |
|---|---|---|
| CN | 102634865 A | 8/2012 |
| EP | 0 532 037 A1 | 3/1993 |
| EP | 2075014 B1 | 7/2011 |
| JP | S52-21420 A | 2/1977 |
| JP | S55-106162 A | 8/1980 |
| JP | S58-014906 A | 1/1983 |
| JP | S61-226061 A | 10/1986 |
| JP | H01-299564 A | 12/1989 |
| JP | H10-306191 A | 11/1998 |
| JP | H11-130929 A | 5/1999 |
| JP | 2002-360685 A | 12/2002 |
| JP | 2007-500764 A | 1/2007 |
| JP | 2012-251057 A | 12/2012 |
| JP | 5820918 B1 | 11/2015 |
| KR | 2018-0110695 A | 10/2018 |
| WO | WO 92/07899 A2 | 5/1992 |
| WO | WO 97/41180 A1 | 11/1997 |
| WO | WO 99/44665 A2 | 9/1999 |
| WO | WO 01/68746 A1 | 9/2001 |
| WO | WO 2007/002004 A2 | 1/2007 |
| WO | WO 2014/077886 A1 | 5/2014 |
| WO | WO 2017/112878 A1 | 6/2017 |
| WO | WO 2018/237166 A1 | 12/2018 |

OTHER PUBLICATIONS

U.S. Appl. No. 17/944,966, filed Sep. 14, 2022, Bassett et al.
U.S. Appl. No. 16/586,787, filed Sep. 27, 2019, Biggins et al.
U.S. Appl. No. 16/014,886, filed Jun. 21, 2018, Mannarino et al.
U.S. Appl. No. 16/719,753, filed Dec. 18, 2019, Mannarino et al.
U.S. Appl. No. 17/193,258, filed Mar. 5, 2021, Doherty et al.
PCT/US2021/039427, Nov. 30, 2021, International Search Report and Written Opinion.
International Search Report and Written Opinion for International Application No. PCT/US2021/039427 dated Nov. 30, 2021.
[No Author Listed], Dimethyl Sulfoxide Physical Properties. Gaylord Chemical Company, L.L.C., Bulletin 101. Jun. 2014. 14 pages.

(56) References Cited

OTHER PUBLICATIONS

Chirilia et al., Poly(2-hydroxyethyl methacrylate) sponges as implant materials: in vivo and in vitro evaluation of cellular invasion. Biomaterials. 1993;14(1):26-38.

Fukumori et al., Significant improvement of mechanical properties for polyvinyl alcohol film prepared from freeze/thaw cycled gel. Open Journal of Organic Polymer Materials. 2013;3:110-116.

Kang, The synthesis of nanoporous hydrogels using sacrificial block copolymers. Dissertation. Massachusetts Institute of Technology. Jul. 21, 2006. 106 pages.

Peppas et al., Semicrystalline poly(vinyl alcohol) films and their blends with poly(acrylic acid) and poly(ethylene glycol) for drug delivery applications. Journal of Drug Delivery Science and Technology. 2004;14(4):291-297.

Sandeman et al., Adsorption of anionic and cationic dyes by activated carbons, PVA hydrogels, and PVA/AC composite. J Colloid Interface Sci. Jun. 15, 2011;358(2):582-92. doi: 10.1016/j.jcis. 2011.02.031. Epub Feb. 17, 2011.

Speybrouck et al., Successful superior thyroid artery embolisation using microporous beads. European Society for Vascular Surgery. 2012;24:e5-e6.

\* cited by examiner (OPEN)          (CLOSED)

ARTICLES COMPRISING MARKINGS AND RELATED METHODS

RELATED APPLICATIONS

This application claims priority under 35 U.S.C. § 119(e) to U.S. Provisional Application Ser. No. 63/046,499, filed Jun. 30, 2020, which is hereby incorporated by reference in its entirety for all purposes.

FIELD

The present invention relates generally to articles, such as catheters, comprising markings. The articles may be medical devices that are configured to be at least partially positioned within a patient, such as articles and/or devices that include elongated shafts that are configured to be positioned in a blood vessel or other patient conduit.

BACKGROUND

Current catheters and other patient-inserted medical devices exhibit various complications, including those related to thrombus formation when positioned in a patient's blood stream, such as when positioned within a vein, artery, and/or the heart of the patient. Thrombus formation can increase the risk of and/or lead to: infection; symptomatic deep vein thrombosis (DVT); pulmonary embolism (PE); asymptomatic thrombus, vessel trauma, and/or vessel occlusion. Complications seen with such devices lengthen hospital stays and increase morbidity and mortality.

There is a need for devices with reduced complications, such as reduced thrombus formation and/or other enhanced performance when positioned within a patient.

SUMMARY

Methods and articles related to marked catheters are generally provided. In some embodiments, a series of methods are provided. In some embodiments, a method comprises: with a marked catheter comprising markings that comprise multiple separate segments spaced along at least a portion of the catheter, wherein an average shortest distance between each segment and its nearest neighbor segment is a first distance in a first configuration of the marked catheter, performing the steps of: introducing a fluid to the marked catheter; and swelling at least a portion of the marked catheter from the first configuration to a second configuration, wherein the average shortest distance between each segment and its nearest neighbor segment in the second configuration becomes a second distance, and wherein a ratio of the second distance to the first distance is greater than or equal to 1.02:1 and less than or equal to 2:1.

In some embodiments, a method comprises: with a marked catheter comprising markings that comprise multiple separate segments spaced along at least a portion of the catheter, wherein an average shortest distance between each segment and its nearest neighbor segment is a first distance in a first configuration of the marked catheter, performing the steps of: introducing a fluid to the marked catheter; and swelling at least a portion of the marked catheter from the first configuration to a second configuration, wherein the average shortest distance between each segment and its nearest neighbor segment in the second configuration becomes a second distance, and wherein the second distance is equal to about 1 mm, about 10 mm, about 100 mm, about 1 cm, or about 10 cm.

In some embodiments, a series of articles are provided. In some embodiments, an article comprises a catheter having a plurality of markings. The markings comprise multiple separate segments spaced along at least a portion of a surface of the catheter. The article has a first configuration having a first water content greater than or equal to 2 w/w % and less than or equal to 40 w/w %. The average shortest distance between each segment and its nearest neighbor segment in the first configuration is a first distance. The article has a second configuration having a second water content of greater than or equal to 20 w/w % and less than or equal to 99.9 w/w %. The average shortest distance between each segment and its nearest neighbor segment in the second configuration is a second distance. The second water content is greater than the first water content. A ratio of the second distance to the first distance is greater than or equal to 1.02:1.

In some embodiments, an article comprises a catheter having a plurality of markings. The markings comprise multiple separate segments spaced along at least a portion of a surface of the catheter. The article has a first configuration having a first water content greater than or equal to 2 w/w % and less than or equal to 40 w/w %. An average shortest distance between each segment and its nearest neighbor segment in the first configuration is a first distance. The article has a second configuration having a second water content of greater than or equal to 20 w/w % and less than or equal to 99 w/w %. The average shortest distance between each segment and its nearest neighbor segment in the second configuration is a second distance. The second water content is greater than the first water content. The second distance is equal to about 1 mm, about 10 mm, about 100 mm, about 1 cm, or about 10 cm.

In some embodiments, an article comprises a catheter and markings. The markings comprise multiple separate segments spaced along at least a portion of a surface of the catheter. At least a portion of the catheter does not comprise the markings. In some embodiments, the article has substantially no thrombus accumulation. A level of thrombus accumulation for the markings is within 50% of a level of thrombus accumulation for the portions of the catheter that do not comprise the markings.

In some embodiments, an article comprises a markings composition comprising a salt, a dye, and a first water-soluble polymer.

In some embodiments, a method comprises disposing a markings composition on a catheter, allowing the markings composition to penetrate at least 10 nm into the catheter, and locking the markings composition into the catheter. The disposing step comprises automated ink-jet deposition. The locking step comprises thermal annealing, heat treatment, water desiccation, lyophilization, or a combination thereof.

In some embodiments, an article comprises a catheter and markings. The markings comprise multiple separate segments spaced along at least a portion of a surface of the catheter. At least a portion of the markings penetrate into the catheter at a depth of between 10 μm to 10 mm.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
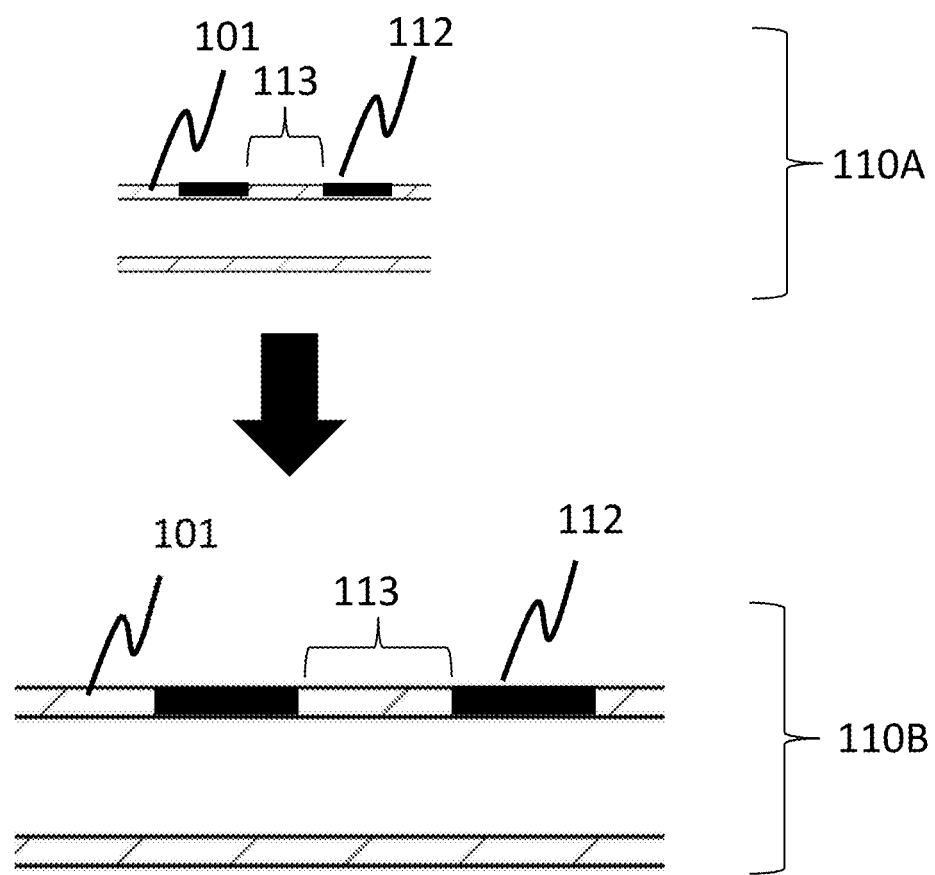
FIG. 1A illustrates a cross-sectional view of an exemplary device comprising markings, according to one set of embodiments.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

Articles, such as catheters, comprising markings and associated methods are generally provided. The articles described herein may be configured to be exhibit one or more desirable properties. For instance, in some embodiments, an article comprises markings that are spaced from each other at known distances. Such markings may be employed to aid users of the article in measuring distances and/or identifying the article. As another example, an article may be configured to swell upon exposure to the fluid such that markings positioned thereon do not crack or delaminate. It is also possible for the article to be configured to swell upon exposure to the fluid in a known, predictable, and/or uniform manner. This swelling may cause the spacings between the markings to increase, and such increase may also be in a known, predictable, and/or uniform manner. When the fluid causing the article to swell is a bodily fluid, such as a fluid the article would be exposed to upon implantation into a patient, and the article swells such that the markings have a known spacing in the patient, the markings may advantageously be employed to measure distances with respect to the patient (e.g., the depth to which the article has been inserted into the patient) and/or the change in marking spacing may be employed to determine the swelling of the article in the patient.

Another advantageous property that some articles described herein may exhibit is a resistance to thrombus accumulation that is advantageous (e.g., consistent with hydrophilic, non-thrombogenic surfaces, such as those of the articles described herein) and/or consistent across the article. A resistance to thrombus accumulation that is consistent with hydrophilic, non-thrombogenic surfaces may desirably prevent the formation of thrombi and/or substantially reduce the rate at which thrombi form when the article is positioned in a patient. Portions of an article implanted into a patient that have a relatively lower resistance to thrombus formation may, even if positioned in an article having an overall relatively high resistance to thrombus formation, serve to nucleate thrombi that may disadvantageously grow across the article. Therefore, a uniform resistance to thrombus formation may be particularly beneficial.

Processes and articles herein advantageously provide high strength materials with a true porous structure and other useful characteristics such as an unexpectedly good combination of biocompatibility and mechanical properties. Embodiments of porous solid materials are provided that have a combination of structural features independently chosen from pore sizes, tensile strength, Young's modulus, solids concentration, crosslinking type and degree, internal alignment, hydrophilicity, and composition for the materials and further, optionally, independently selecting end-user devices or intermediate materials having a desired aspect ratio for molded shapes, a lumen, a plurality of lumens, tubes with concentrically placed lumens or a range of tolerance of thickness, or a particular medical device: each of these are further detailed herein.

Advantageously, the markings may be, in some embodiments, seamless with the body of the catheter. In some such embodiments, the markings may provide measurements (e.g., for clinical insertion) without becoming a landmark for thrombus accumulation.

The methods and compositions described herein may be useful for providing artwork, labels, product descriptions, brands, logos, or the like to various articles (e.g., catheters, suture wings, medical devices, polymeric materials). For example, labels, markings, and/or identifiers may be provided to the articles described herein.

In an exemplary set of embodiments, a method comprises swelling a conduit comprising markings, such as a marked catheter, from a first unswollen configuration to a second swollen configuration. The markings may take the form of multiple separate segments spaced along at least a portion of a surface of the conduit. This swelling may cause the average shortest distance between the markings to increase from a first average shortest distance to a second average shortest distance. For instance, the method may comprise swelling the conduit such that a ratio of the first average shortest distance to the second average shortest distance is greater than or equal to 1.02:1 and less than or equal to 2:1. As another example, the method may comprise swelling the conduit such that the second average shortest distance is equal to about 1 mm, about 1 cm, or about 10 cm. In another exemplary set of embodiments, an article is provided. The article may comprise a conduit, such as a catheter, comprising a plurality of markings. The conduit may be configured such that it has a first unswollen configuration including a relatively low amount of water (e.g., of greater than or equal to 2 w/w % and less than or equal to 40 w/w %) and a second swollen configuration including a higher amount of water (e.g., of greater than or equal to 20 w/w % and less than or equal to 99 w/w %). The average shortest distance between the markings, which may take the form of multiple separate segments spaced along at least a portion of a surface of the conduit, may be larger in the swollen configuration than in the unswollen configuration. In some embodiments, the ratio of the average shortest distance between the markings in the swollen configuration to the spacing between the markings in the unswollen configuration is greater than or equal to 1.02:1 and less than or equal to 2:1. In some embodiments, the average shortest distance in the swollen conduit is equal to about 1 mm, about 1 cm, or about 10 cm.

In a third exemplary set of embodiments, an article is provided. The article may comprise a conduit, such as a catheter, that comprises markings in some portions and lacks markings in other portions. Both the markings and the conduit may be relatively resistant to thrombus formation. For instance, the article as a whole may have substantially no thrombus formation and/or the thrombus accumulation on the markings may be within 50% of the thrombus accumulation on the portions of the conduit lacking the markings.

In a fourth exemplary set of embodiments, a markings composition is provided. The markings composition may be suitable for deposition onto a conduit, such as a catheter, to form a marked conduit. The markings composition may comprise a salt, a dye, and a water-soluble polymer.

In a fifth set of exemplary embodiments, a method for forming an article is provided. The method comprises disposing a markings composition on a conduit, such as a catheter, to form markings thereon. In some embodiments, the markings composition may be deposited, and then allowed to penetrate a certain distance into the conduit (e.g., at least 10 nanometers, at least 10 microns). Subsequently, the markings may be locked into the conduit. Locking in the markings may comprise arresting their penetration into the catheter and/or chemically bonding them to the conduit. This may be accomplished by the application of a stimulus, such as heat, to the conduit and/or the markings composition. A variety of suitable deposition techniques may be employed, including automated ink-jet deposition and/or pad printing.

In some embodiments, locking comprises heat treatment, water desiccation, lyophilization, thermal annealing, or combinations thereof.

In some embodiments, the marking is deposited on a surface of the article.

In a sixth set of exemplary embodiments, an article is provided that comprises a conduit, such as a catheter, and markings. At least a portion of the markings may penetrate into the interior of the conduit. The depth of penetration may be between 10 nanometers and 10 microns, or between 10 nanometer and 10 mm, or between 10 microns and 10 mm. The markings may take the form of multiple separate segments spaced along the surface of the conduit.

For example, as illustrated in cross-sectional view in FIG. 1A, device 100 comprises conduit 110 (e.g., a catheter) and markings 112 spaced along at least a portion of conduit 110. In some embodiments, conduit 110 may have a first configuration 110A (e.g., an unswollen configuration) and a second configuration 110B (e.g., a swollen configuration). In some embodiments, markings have an average shortest distance 113 between markings. For example, swelling between first configuration 110A and second configuration 110B results in an increase in average shortest distance 113 between markings.

It should also be understood that some methods may comprise implanting the articles described herein at least partially into a patient, some methods may comprise fabricating the articles described herein, and some embodiments may relate to articles fabricated by the methods described herein.

One example of the articles provided herein are medical devices, such as catheters, including enhanced materials, such as materials configured to prevent thrombus formation or provide other enhanced performance when positioned in a patient. Methods of manufacturing these articles and/or medical devices are also provided. The enhanced materials described herein can be used to create catheter shafts and/or other device components that have a relatively high water content and/or neutral surface charge (e.g. to minimize the body's foreign body response). These enhanced materials can provide increased strength (e.g. for introduction into a blood vessel) and improved lumen patency, while reducing trauma to the vessel(s) into which the associated device is inserted. The enhanced materials can comprise materials with: hydrophilic properties; high strength; enhanced flexibility; and/or a nanoporous structure. The medical devices of the present inventive concepts can comprise catheters which can be inserted into a blood vessel of the patient without the need for an introducer (reducing that associated trauma to the vessel).

It is also possible for the devices described herein, and the associated techniques for disposing markings on devices to be performed on, devices other than medical devices. For instance, some embodiments relate to PVA films (e.g., as used in detergent pods), PVA membranes, and/or methods related to such devices.

Figure 1B:
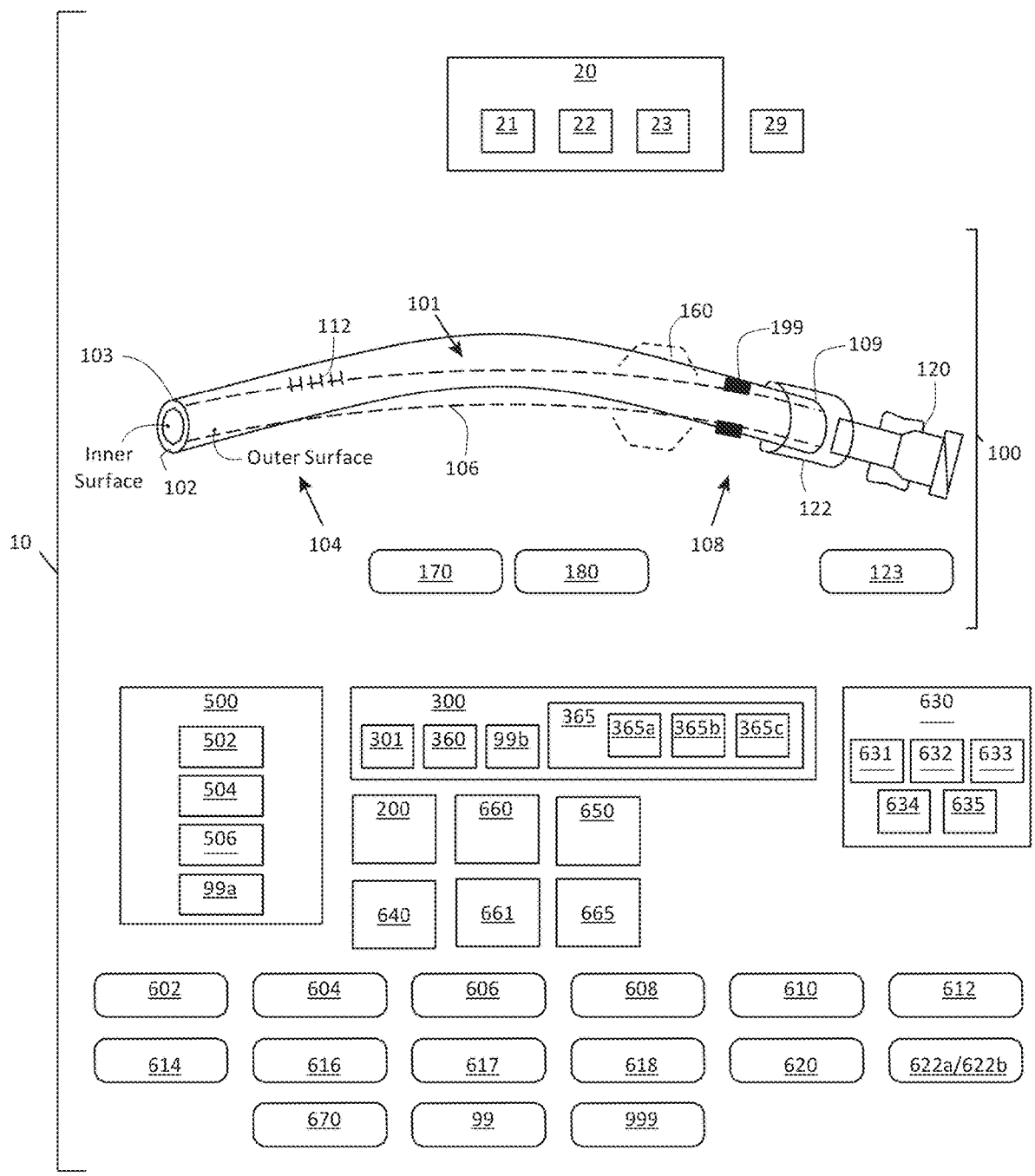
FIG. 1B illustrates a perspective view of a medical device and a schematic view of a system for producing the medical device, consistent with some embodiments.

Referring now to FIG. 1B, a perspective view of one example of an article is provided: a medical device comprising a conduit and a schematic of a system for producing the medical device. System 10 shown in FIG. 1B comprises medical device 100, as well as various components used to manufacture, package, and/or sterilize device 100. Device 100 can be shipped to a hospital, doctor's office, and/or other clinical setting (the "clinical site") for placement of device 100 into the patient. Device 100 can be implanted in the patient (e.g. in a surgical procedure) at an "implant location". Alternatively, device 100 can be inserted into a patient through the patient's skin at an "insertion location" (e.g. when device 100 passes through the skin and into a blood vessel of the patient). The implantation or insertion ("insertion" herein) procedure can be performed in an operating room, catheterization lab, and/or other location in which sterile procedures can be performed (the "procedure site").

Device 100 can comprise a tube, conduit 101 comprising a proximal portion 104 with a proximal end 103, a distal portion 108 with a distal end 109, and a lumen 106 therebetween. Conduit 101 can comprise a wall 102 surrounding lumen 106, such that wall 102 includes an inner surface (e.g. interior of conduit 101) and an outer surface (e.g. exterior of conduit 101). Conduit 101 can be constructed, or otherwise fabricated, from a polymeric material 20, such as is described herebelow. Device 100 can further include a mechanical interlock connector (e.g. a luer connector), connector 120, which can be configured to operably attach (e.g. fluidly attach) device 100 to another device. System 10 can include an extrusion device, extruder 500, which can be configured to produce one or more components of device 100, such as conduit 101 of device 100. System 10 can further include various tools, containers, solutions, equipment, devices, and/or other components that can be used to manufacture, package, and/or store device 100 and/or its components (e.g. conduit 101).

In some embodiments, device 100, extruder 500, and/or another component of system 10 is of similar construction and arrangement to the similar components described in applicant's co-pending applications.

Device 100 can comprise at least a portion of a medical device, such as a device configured to be implanted or otherwise inserted into a patient. In some embodiments, device 100 comprises a conduit 101 that is attached or attachable to another medical device, such as when device 100 comprises a catheter that is attached to a pump such as an implantable pump (e.g. an implantable pump configured to deliver a drug or other agent to the patient's vasculature, a ventricle of the brain, a space of the spine (e.g. the epidural or intrathecal space of the spine), and/or a location within the patient's gastrointestinal system (e.g. the stomach or intestine). Device 100 can comprise a catheter selected from the group consisting of: central venous catheter; peripheral central catheter; peripheral port catheter; central venous port catheter; midline catheter; peripheral catheter; tunneled catheter; dialysis access catheter; urinary catheter; neurological catheter; peritoneal catheter; intra-aortic balloon pump catheter; diagnostic catheter; interventional catheter; drug delivery catheter; drainage catheter; central nervous system catheter; hemodialysis catheter; and combinations of these.

Additionally or alternatively, device 100 can comprise a medical device selected from the group consisting of: shunt; wound drain, such as an external would drain (e.g. ventricular, ventriculoperitoneal, lumboperitoneal); infusion port; soft tissue patch; drug delivery device, such as an insulin pump; tubing; contraceptive device; feminine hygiene device; endoscope; graft; pacemaker; implantable cardioverter-defibrillator; cardiac resynchronization device; cardiovascular device lead, wherein conduit 101 can further comprise insulation for the lead; ventricular assist device; cochlear implant; endotracheal tube; tracheostomy tube; implantable sensor device (e.g. intravascular, transdermal, intracranial); ventilator pump; ophthalmic device, such as an ophthalmic drug delivery device; and combinations of these.

At least a portion of device 100 can be configured to contact bodily fluids within a patient. For example, device 100 can comprise an ex vivo and/or in vivo device, such as a blood contacting implant.

At least a portion of device 100 can be comprise a patient-inserted device, such as a percutaneously inserted device. At least a portion of device 100 can comprise a permanently inserted device. For example, device 100 can remain inserted within a patient for more than five years. At least a portion of device 100 can comprise a temporarily inserted device. For example, device 100 can remain inserted within a patient for no more than five years, such as no more than one year, such as no more than six months, such as no more than three months.

Conduit 101 can comprise one, two, or more nanoporous materials, microporous materials, and/or high-strength hydrogels. Conduit 101 be configured to prevent, or otherwise reduce (e.g., in comparison to other conduits), thrombus accumulation when implanted in a patient. The conduit, as a whole, may be configured such that it has a reduction in thrombus accumulation compared to polyurethane materials, and/or substantially no thrombus accumulation when positioned in one or more relevant environments (e.g., a bodily fluid, a patient). For instance, in some embodiments, a conduit may exhibit substantially no thrombus accumulation in comparison to an otherwise equivalent conduit formed from polyurethane. In some embodiments, conduit 101 comprises one, two, or more polymeric materials 20 configured to reduce thrombus accumulation. Such polymeric materials may include the water-soluble polymers described elsewhere herein as suitable for inclusion in the conduit. An exemplary method for determining thrombus accumulation (e.g., non-thrombogenicity) is described in Example 1.

Applicant has conducted studies to evaluate the thromboresistance of one suitable type of conduit 101 (a HydroPICC catheter) within an in vitro blood flow loop system, whereby the applicant assessed the thrombus formation and platelet adhesion to conduit 101 in the presence of blood. The blood flow loop system is capable of assessing inherent device thrombosis characteristics. The haematological parameters (e.g., hemodynamics, anticoagulation) in this in vitro model are believed to be more controlled than in in vivo models and to allow for direct semi-quantitative evaluation of thrombogenicity. Extraneous dynamic parameters (e.g., vessel geometry, animal physiology, activity, variable haemostasis, and homeostasis, and infection) that can confound in vivo assessments can be eliminated in the in vitro blood loop model. This is believed to allow the thromboresistance evaluation to be focused on the surface properties and chemistry of conduit 101, with other parameters remaining relatively constant. The in vitro blood loop model is believed to allow for the isolated quantification of platelet adhesion. As platelet adhesion is believed to be a fundamental and critical step in thrombus formation, its quantification is believed to be a conservative measure of the thrombus accumulation.

For the studies performed by Applicant, the blood flow loop comprised ¼ inner diameter polyvinyl chloride tubing. Conduit 101 comprising lumen 106 was hydrated in sterile saline for approximately 24 hours prior to insertion into the blood flow loop. Subsequently, conduit 101 was cut into samples comprising a length of approximately 15 cm. The proximal opening of lumen 106 was occluded with epoxy to simulate a "locked" catheter. Fresh bovine blood was collected by cardiac puncture and heparin was added to achieve a 0.75 U/mL concentration. Autologous platelets were purified, labelled with 111-Indium, and added back into the bovine blood. Conduits 101 were inserted into the blood flow loop and remained within the loop for approximately 120 minutes. The bovine blood was maintained at a temperature of 37° C. and was pumped through the blood flow loop via a peristaltic pump at a rate of 200 mL/min, thereby simulating a physiological blood flow across conduit 101. Conduits 101 were assessed for thrombus accumulation after 45 minutes and removed from the blood flow loop after between 60 minutes and 120 minutes. Once removed from the blood flow loop, conduits 101 were rinsed with saline and placed within a gamma counter for analysis.

Figure 2:
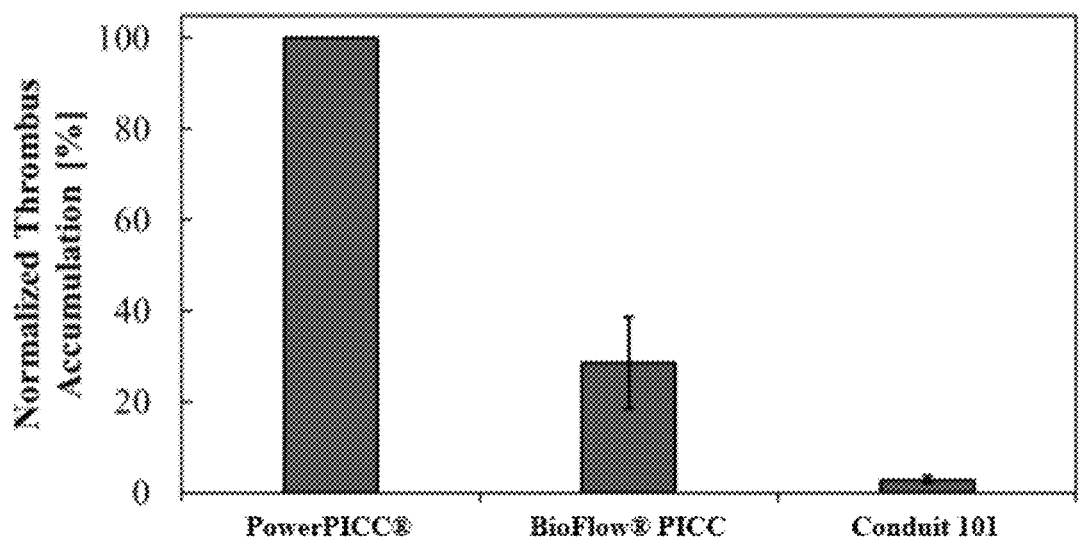
FIG. 2 shows data comparing the normalized thrombus accumulation across different conduits, consistent with some embodiments.

In addition to conduit 101, Applicant similarly evaluated two commercially available peripherally inserted central catheters (PICC): PowerPICC® by Bard Access Systems, Inc. and BioFlo® PICC by AngioDynamics, Inc. Samples of PowerPICC® and BioFlo® PICC were assessed for thrombus accumulation according to the blood flow loop system as described hereabove. Applicant observed significant thrombus accumulation on the PowerPICC® and BioFlo® PICC samples, whereas minimal thrombus accumulation was observed on conduit 101. To take into account that some haematological parameters cannot be consistently controlled between experimental groups, the radiation counts for conduit 101 and BioFlo® PICC samples were normalized to the radiation counts for PowerPICC®. A plot of the normalized thrombus accumulation for PowerPICC®, BioFlo® PICC, and conduit 101 is shown in FIG. 2.

Conduit 101 and BioFlo® PICC were observed to exhibit a statistically significant reduction of thrombus formation compared to PowerPICC® based on a paired, two-sided t-test (p-values of 0.017 and 0.035, respectively). Conduit 101 was also observed to exhibit a statistically significant decrease in thrombus accumulation when compared to BioFlo® PICC (p-value of 0.033). When compared to PowerPICC®, BioFlo® PICC exhibited a 71±30% reduction in thrombus accumulation, whereas conduit 101 exhibited a 97±2% reduction in thrombus accumulation.

Conduit 101 can comprise one, two, or more polymeric materials 20 that are configured to restrict dimensional changes to device 100 (e.g. restrict dimensional changes to conduit 101). In some embodiments, the included polymeric materials are configured to restrict dimensional changes (e.g., length, outer diameter, inner diameter) to conduit 101 to less than 15%, such as less than 10%, such as less than 5%, when exposed to water, a solvent, a non-solvent, aqueous solutions, or mixtures thereof. Polymeric materials 20 can be configured to restrict the dimensional change of conduit 101 to a minimal change in length (e.g. near 0%) and/or no more than 10% in outer diameter, such that conduit 101 demonstrates anisotropic swelling.

For example, in some embodiments, the ratio of the swelling of the inner diameter to the swelling of the outer diameter is greater than or equal to 0.1, greater than or equal to 0.2, greater than or equal to 0.5, greater than or equal to 0.8, greater than or equal to 0.9, greater than or equal to 1, greater than or equal to 1.1, greater than or equal to 1.2, greater than or equal to 1.5, greater than or equal to 2, greater than or equal to 5, or greater than or equal to 8. In some embodiments, the ratio of the swelling of the inner diameter to the swelling of the outer diameter is less than or equal to 10, less than or equal to 8, less than or equal to 5, less than or equal to 2, less than or equal to 1.5, less than or equal to 1.2, less than or equal to 1.1, less than or equal to 1, less than or equal to 0.9, less than or equal to 0.8, less than or equal to 0.5, or less than or equal to 0.2. Combinations of the above-referenced ranges are also possible (e.g., greater than or equal to 0.1 and less than or equal to 10). Other ranges are also possible.

In some embodiments, conduit 101 is configured to decrease in length when exposed to water, a solvent, a non-solvent, aqueous solutions, or mixtures thereof. The outer diameter of conduit 101 can be configured to increase as the length decreases. Such an embodiment can be employed in anatomical features (e.g. blood vessel) that may require a widening for support and/or further manipulation.

Conduit 101 and/or another portion of device 100 can be configured to swell and/or deswell according to its water content. Additionally or alternatively, conduit 101 and/or another portion of device 100 is, in some embodiments, further configured to swell and/or deswell according to its sodium chloride content. In some embodiments, device 100 can comprise a sodium chloride content comprising 10 wt % configured to reduce or otherwise limit its swelling capacity. The conduit may swell upon exposure to a variety of suitable fluids, including water, bodily fluids, an isotonic salt solution (e.g., 1× phosphate buffered saline, normal saline), lactated Ringer's solution (LRS), dextrose (D5W), phosphate buffered saline (PBS), and/or Hanks' Balanced Salt Solution (HBSS), normal saline, and/or physiological body fluids.

It is also possible for a conduit 100 and/or another portion of device 100 to dissolve and/or to be configured to dissolve upon exposure to the fluids described in the preceding paragraph.

In some embodiments, when hydrated (e.g. with a high-water content), a mandrel of system 10, (e.g. mandrel 614 described herebelow), is slidingly inserted into lumen 106 of conduit 101. The inserted mandrel 614 can comprise a diameter that is greater than the diameter of lumen 106 when device 100 is dehydrated (e.g. at a low-water content), such as to provide a radial expansion force on conduit 101. In some embodiments the diameter of the mandrel is smaller than or equal to the inner diameter of the hydrated conduit 101, but larger than or equal to the inner diameter of the dehydrated conduit 101.

Conduit 101 and/or another portion of device 100 can be dehydrated and annealed (either or both of which may be performed under vacuum or in the presence of one or more gases), such as when maintained at a temperature between 90° C. and 180° C., such as a temperature between 130° C. and 160° C., such as 150° C. (e.g. when maintained within a particular temperature range by a component of system 10).

In some embodiments, and prior to annealing, one, two, or more shaping elements (not shown) can be inserted into at least a portion of lumen 106 of conduit 101. In some embodiments, and prior to annealing, one, two, or more shaping elements can slidingly receive and surround at least a portion of conduit 101. Shaping elements can be configured to encourage conduit 101 to adopt a desired shape (e.g. curvature). Annealing conduit 101 with shaping element therein can be configured to "lock in" the desired shape. Shaping element can comprise a material selected from the group consisting of: steel; polypropylene; nylon; polysulfide; polysulfone; nickel-titanium alloy; and combinations of these.

A conduit 101 that is being dehydrated and annealed can be configured to compress around an inserted mandrel 614, such as to increase hydrogen bonding and/or polymer chain orientation within conduit 101. Upon dehydration and diameter change, compression may occur around a mandrel. This compression may induce chain orientation via hydrogen bonding in a radial fashion, much like an extrusion can be drawn linearly out of a die. An increase in hydrogen bonding and/or polymer chain orientation can be performed (e.g. via the dehydration of conduit 101 over mandrel 614) to increase the overall strength of device 100 and/or reduce subsequent swelling of device 100 (e.g. reduce the expansion of device 100) when subsequently hydrated. In some embodiments, the annealing process can be repeated multiple times with hydration and drying steps occurring between cycles to increase the degree of hydrogen bonding and/or polymer chain orientation. These mechanical properties (e.g. Young's modulus, peak tensile strength, yield stress, strain at break, tensile energy to break, elongation, etc.) can be altered when solvated in water above the glass transition temperature of the base polymer.

In some embodiments, the dimensions of conduit 101 (e.g. the outer diameter and inner diameter) do not change more than 5% when conduit 101 is hydrated in water after being annealed at a temperature of between 120° C. and 180° C. for one or more cycles. For example, a dehydrated conduit 101 can comprise an inner diameter of approximately 1.0 mm and an outer diameter of approximately 1.33 mm, whereas the same conduit 101 when hydrated can comprise an inner diameter of approximately 1.2 mm and an outer diameter of approximately 1.5 mm. In this example, the inner diameter increases by approximately 0.83% and the outer diameter increases by approximately 0.88%. Additionally or alternatively, the overall length of conduit 101 does not change more than 5% in some embodiments.

Polymeric material 20 can comprise a water-soluble polymer, polymer 21. In some embodiments, water-soluble polymer 21 comprises one, two, or more polymers selected from the group consisting of: poly(vinyl alcohol); poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly(2-hydroxymethylmethacrylate); and combinations of these. In some embodiments, the polymeric material comprises a co-polymer of the water-soluble polymers listed above.

Polymeric material 20 can comprise one, two, or more radiopaque materials, agent 22. In some embodiments, radiopaque agent 22 comprises one, two, or more agents selected from the group consisting of: bismuth subcarbonate; barium sulfate; bismuth trioxide; bismuth oxychloride; tungsten; platinum; gold; titanium dioxide; tantalum; palladium; silver; and combinations of these.

Polymeric material 20 can comprise one, two, or more phosphate salt solutions, solution 23. In some embodiments, phosphate salt solution 23 comprises one, two, or more solutions selected from the group consisting of: monobasic sodium phosphate; dibasic sodium phosphate; tribasic sodium phosphate; and combinations of these.

Polymeric material 20 can comprise one, two, or more plasticizers, plasticizer 29. In some embodiments, plasticizer 29 comprises a material selected from the group consisting of: polyols, such as glycerol; propylene glycol; water; ethylene glycol; butylene glycol; erythritol; threitol; arabitol; xylitol; ribitol; mannitol; sorbitol; galactitol; fucitol; iditol; inositol; volemitol; malitol; lactitol; maltotriitol; maltotetraitol; polyglycitol; and combinations of these. In some embodiments, a polyol is included in material 20 to plasticize, as well as to serve as a humectant to improve hydration efficiency of conduit 101. A polyol can be added to material 20 prior to annealing and/or after annealing in a secondary rehydration step. A plasticizer 29 can be included to prevent cracking and/or fracturing during storage of conduit 101 when in a dry (e.g. unhydrated) state. Addition of plasticizer 29 can be performed in addition to a humectant to improve hydration performance.

In some embodiments, conduit 101 is submerged in a soaking solution (aqueous or solvent-based) comprising the plasticizer and/or humectant at a specified temperature (e.g. below the $T_g$ of the base polymeric material). The soaking solution can be stagnant or configured to flow across at least a portion of conduit 101. After soaking, conduit 101 can be dried (such as via ambient, convection, vacuum, or dry gas purge) and annealed. Additionally, conduit 101 can be soaked after the drying and annealing process.

As used herein, a mixture comprising water-soluble polymer 21, radiopaque agent 22, sodium phosphate solution 23, and/or plasticizer 29, is referred to generally as polymeric material 20.

Proximal portion 104 and/or distal portion 108 of conduit 101 can comprise a blunt end, radiused end, beveled end, tapered shape, and/or otherwise modified end portion (e.g. modified proximal portion 104 and/or modified distal portion 108). In some embodiments, radiofrequency (RF) energy is applied to portions 104 and/or 108 (e.g. to ends 103 and/or 109, respectively) to achieve a modified end portion. In some embodiments, a tipping process (e.g. a melt tipping process) is applied to portions 104 and/or 108 to achieve a modified end portion. In some embodiments, a solvent and/or solvent mixture is applied to portions 104 and/or 108 to achieve a modified end portion.

In some embodiments, conduit 101 comprises one, two, or more markings, markings 112 shown, along one or more portions of conduit 101. It is also possible for one or more portions of the conduit 101 to lack markings (e.g., in addition to other portions that comprise markings). Markings 112 can be positioned relative to a single point of conduit 101. The markings may comprise multiple separate segments. For instance, some markings may be graduated (e.g., to show one or more distances). In some embodiments, markings 112 are configured to provide a "ruler" to aid in depth of insertion of device 100 into the patient. It is also possible for markings to comprise text and/or words. For instance, in some embodiments, a markings comprises a number and/or phrase that indicates a distance (e.g., "5 cm"). When a marking comprises text and/or words, the text and/or words may indicate distances from the distal end of the catheter and/or may have increasing numerical values from the distal end of the catheter to the proximal end of the catheter. Some conduits may comprise some markings that take the form of segments and some markings that take the form of text and/or words. As one example, a conduit may comprise markings that are more-closely spaced (e.g., every 1 cm) that take the form of segments and some markings that are less-closely spaced (e.g., every 5 cm) that comprise text and/or words. Markings comprising text and/or words may further comprise a segment. The markings taking the form of segments may be positioned between markings comprising text and/or words.

In some embodiments, markings 112 are configured to provide identifying features of device 100, such as a model number, date of manufacture, etc. In some embodiments, the markings are positioned on at least a portion of a surface of the conduit. By way of example, when the conduit is a catheter, the marking may be positioned along at least a portion of a surface of the catheter.

Markings may be formed from a variety of suitable materials. In some embodiments, markings comprise a polymer, such as a water-soluble polymer. Non-limiting examples of suitable water-soluble polymers include poly (vinyl alcohol), poly(acrylic acid), polyethylene glycol, poly (vinyl pyrrolidone), poly(methacrylic sulfobetaine), poly (acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), and/or poly(2-hydroxymethylmethacrylate). When both the conduit on which the markings are positioned and the markings comprise one or more water-soluble polymers, the conduit and the markings may have identical chemical compositions or may have chemical compositions that differ in one or more ways. For instance, a conduit and markings thereon may comprise exclusively the same type(s) of water-soluble polymers, may comprise some water-soluble polymers in common and some water-soluble polymers that differ between the two, or may each comprise water-soluble polymer(s) not present in the other. It is also possible for a marking to comprise a polymer that is not soluble in water. In an exemplary set of embodiments, the marking is formed from a material selected from the group consisting of poly(vinyl alcohol) and poly(vinyl acetate). In some embodiments, the marking material comprises greater than or equal to 75 wt % (solid content, e.g., greater than or equal to 80 wt %, greater than or equal to 85 wt %, greater than or equal to 90 wt %, greater than or equal to 95 wt %, or greater than or equal to 98 wt %) of poly(vinyl alcohol). In some embodiments, the marking material comprises less than or equal 100 wt % (solid content, e.g., less than or equal to 99 wt %, less than or equal to 98 wt %, less than or equal to 95 wt %, less than or equal to 90 wt %, less than or equal to 85 wt %, or) less than or equal to 80 wt % of poly(vinyl alcohol) versus the total weight of the marking material. Combinations of the above referenced ranges are also possible (e.g., greater than or equal to 75 wt % and less than or equal to 100 wt %). Other ranges are also possible.

Markings may also further comprise one or more further species. For instance, in some embodiments, markings comprise a dye, such as a reactive dye. Non-limiting examples of suitable reactive dyes include tetrasodium; 4-amino-5-hydroxy-3,6-bis[[4-(2-sulfonatooxyethylsulfonyl)phenyl]diazenyl]naphthalene-2,7-disulfonate (Reactive Black 5), copper; 33-[[4-(2-hydroxyethylsulfonyl)phenyl]sulfamoyl]-2,11,20,29,39,40-hexaza-37,38-diazanidanonacyclo [28.6.1.13,10.112,19.121,28.04,9.013,18.022,27.031,36]tetraconta-1,3(40),4(9),5,7,10,12(39),13(18),14,16,19,21,23, 25,27,29,31(36),32,34-nonadecaene-6,15,24-trisulfonic acid (Reactive Blue 21), 2-Naphthalenesulfonicacid,7-(acetylamino)-4-hydroxy-3-[[4-[[2-(sulfooxy)ethyl]sulfonyl]phenyl]azo]-,disodium salt (9CI) (Reactive Orange 78), Reactive Yellow 15, Disodium 1-amino-9,10-dioxo-4-[(3-{[2-(sulfonatooxy)ethyl]sulfonyl}phenyl)amino]-9,10-dihydro-2-anthracenesulfonate (Reactive Blue 19), 1-Amino-4-[3-(4,6-dichlorotriazin-2-ylamino)-4-sulfophenylamino] anthraquinone-2-sulfonic acid (Reactive Blue 4), C.I. Reactive Red 11, 4-[2-(5-carbamoyl-1-ethyl-4-methyl-2,6-dioxopyridin-3-ylidene)hydrazinyl]-6-[(4,6-dichloro-1,3,5-triazin-2-yl)amino]benzene-1,3-disulfonate (C.I. Reactive Yellow 86), Tetrasodium 6,13-dichloro-3,10-bis [[4-[(4,6-dichloro-1,3,5-triazin-2-yl) amino] sulphonatophenyl] amino] triphenodioxazinedisulphonate (C.I. Reactive Blue 163), and/or 5-(benzoylamino)-4-hydroxy-3-[[1-sulfo-6-[[2-(sulfooxy)ethyl]sulfonyl]-2-naphthalenyl]azo]-, tetrasodium salt (C.I. Reactive Red 180).

In some embodiments, a marking comprises a non-reactive dye, pigment, and/or radiopacifier. The non-reactive dye, pigment, and/or radiopacifier may enhance the contrast between the markings and other portions of the catheter (e.g., when the catheter is observed by eye and/or by microscopy, such as fluoroscopy). Non-limiting examples of suitable non-reactive dyes include: phthalocyanine blue, phthalocyanine green, carbazole violet, C.I. Vat Orange 1, 2-[[2,5-Diethoxy-4-[(4-methylphenyl)thiol]phenyl]azo]-1, 3,5-benzenetriol, 16,23-Dihydrodinaphtho[2,3-a:2',3'-i] naphth [2',3':6,7] indolo [2,3-c] carbazole-5,10,15,17,22,24-hexone, N,N'-(9,10-Dihydro-9,10-dioxo-1,5-anthracenediyl) bisbenzamide, 7,16-Dichloro-6,15-dihydro-5,9, 14,18-anthrazinetetrone, 16,17-Dimethoxydinaphtho [1,2,3-cd:3',2',1'-lm] perylene-5,10-dione, 4-[(2,4-dimethylphenyl) azo]-2,4-dihydro-5-methyl-2-phenyl-3H-pyrazol-3-one, 6-Ethoxy-2-(6-ethoxy-3-oxobenzo[b]thien-2(3H)-ylidene) benzo[b]thiophen-3 (2H)-one, Disodium 1-amino-4-[[4-[(2-bromo-1-oxoallyl)amino]-2-sulfonatophenyl]amino]-9,10-dihydro-9,10-dioxoanthracene-2-sulfonate, and combinations hereof. Non-limiting examples of suitable non-reactive pigments include: carbon black, modified carbon black, titanium dioxide, chromium-cobalt-aluminum oxide, chromium oxide greens, iron oxides, mica-based pearlescent pigments, and combination thereof. Non-limiting examples of radiopaque dyes include platinum, palladium, bismuth oxychloride, bismuth subcarbonate, tantalum, barium sulfate, silver, gold, silver sulfadiazine, titanium dioxide, and iodine based compounds such as Omnipaque. In some embodiments, the marking comprises a fluorescent dye (e.g., Fluorescein isothiocyanate (FIT-C), fluorescein-N-hydroxysuccinimide, eosin Y, and the like)

In some embodiments, the markings comprise a salt. Non-limiting examples of suitable salts include phosphates (e.g., MSP, DSP, TSP), borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments, the markings comprise a TPU pad printing ink, such as Tampa® Pur 980 Black TPU and/or Tampa® Star 980 Black TPR, Marabu GmbH & Co.

Regardless of whether the markings have a similar (or identical) composition to the conduit or a different composition therefrom, the markings and portions of the conduit lacking the markings (if present) may exhibit similar thrombus accumulation when the conduit is positioned in one or more environments (e.g., a bodily fluid, a patient). In some embodiments, in one or more such environments, a level of thrombus accumulation for the markings is within 50%, within 40%, within 30%, within 20%, within 10%, within 5%, within 2%, or within 1% of the level of thrombus accumulation of portions of the conduit lacking the markings. In some embodiments, the markings are configured such that they exhibit substantially no thrombus accumulation when the conduit is positioned in a patient.

As described elsewhere herein, some embodiments comprise swelling a conduit from an unswollen state (e.g., a first configuration) to a swollen state (e.g., a second configuration). In some embodiments, swelling of the conduit may cause the markings to undergo a change in morphology. For instance, in some embodiments, the distance between markings taking the form of multiple segments spaced along a conduit may change if the conduit swells (e.g., in the presence of a fluid, such as any of the fluids described elsewhere herein as possibly causing swelling of the conduit). The markings may have a first average shortest distance (e.g., a "first distance") between nearest neighbors prior to conduit swelling and a second, different average shortest distance (e.g., a "second distance") after conduit swelling. The second average shortest distance may be larger than the first average shortest distance. In some embodiments, a ratio of the second average shortest distance to the first average shortest distance is greater than or equal to 1.02:1, greater than or equal to 1.05:1, greater than or equal to 1.075:1, greater than or equal to 1.1:1, greater than or equal to 1.2:1, greater than or equal to 1.5:1, or greater than or equal to 1.75:1. In some embodiments, a ratio of the second average shortest distance to the first average shortest distance is less than or equal to 2:1, less than or equal to 1.75:1, less than or equal to 1.5:1, less than or equal to 1.2:1, less than or equal to 1.1:1, less than or equal to 1.075:1, or less than or equal to 1.05:1. Combinations of the above-referenced ranges are also possible (e.g., greater than or equal to 1.02:1 and less than or equal to 2:1, or greater than or equal to 1.05:1 and less than or equal to 1.1:1).

The shortest distance between two markings may be determined by identifying the shortest line segment that connects the two markings. Each marking may be considered to have a nearest neighbor marking, which is the marking to which it has the smallest shortest distance. The average shortest distance between nearest neighbors for a plurality of markings may be determined by determining the shortest distance between each marking and its nearest neighbor and then averaging these values.

In some embodiments, a swollen article (e.g., a conduit) may comprise markings having an average shortest distance between nearest neighbors that is particularly advantageous. The average shortest distance between nearest neighbor markings in a swollen conduit (e.g., a conduit in a second configuration) may be greater than or equal to 1 mm, greater than or equal to 5 mm greater than or equal to 10 mm greater than or equal to 50 mm greater than or equal to 0.1 cm, greater than or equal to 0.2 cm, greater than or equal to 0.5 cm, greater than or equal to 0.75 cm, greater than or equal to 1 cm, greater than or equal to 1.25 cm, greater than or equal to 1.5 cm, greater than or equal to 2 cm, greater than or equal to 2.5 cm, greater than or equal to 3 cm, greater than or equal to 4 cm, greater than or equal to 5 cm, greater than or equal to 7.5 cm, or greater than or equal to 10 cm. The average shortest distance between nearest neighbor markings in a swollen conduit may be less than or equal to 20 cm, less than or equal to 10 cm, less than or equal to 7.5 cm, less than or equal to 5 cm, less than or equal to 4 cm, less than or equal to 3 cm, less than or equal to 2.5 cm, less than or equal to 2 cm, less than or equal to 1.5 cm, less than or equal to 1.25 cm, less than or equal to 1 cm, less than or equal to 0.75 cm, less than or equal to 0.5 cm, less than or equal to 0.2 cm, less than or equal to 0.1 cm, less than or equal to 50 mm, less than or equal to 10 mm, or less than or equal to 5 mm. Combinations of the above-referenced ranges are also possible (e.g., greater than or equal to 1 mm and less than or equal to 10 mm, greater than or equal to 0.1 cm and less than or equal to 10 cm, or greater than or equal to 0.5 cm and less than or equal to 5 cm). Other ranges are also possible.

In some embodiments, the article has an average shortest distance between nearest neighbors in an unswollen state in one or more of the ranges described above (e.g., greater than or equal to 1 mm and less than or equal to 10 mm, greater than or equal to 0.1 cm and less than or equal to 10 cm, or greater than or equal to 0.5 cm and less than or equal to 5 cm). For example, the average shortest distance between nearest neighbor markings in an unswollen conduit (e.g., a conduit in a second configuration) may be greater than or equal to 1 mm, greater than or equal to 5 mm greater than or equal to 10 mm greater than or equal to 50 mm greater than or equal to 0.1 cm, greater than or equal to 0.2 cm, greater than or equal to 0.5 cm, greater than or equal to 0.75 cm, greater than or equal to 1 cm, greater than or equal to 1.25 cm, greater than or equal to 1.5 cm, greater than or equal to 2 cm, greater than or equal to 2.5 cm, greater than or equal to 3 cm, greater than or equal to 4 cm, greater than or equal to 5 cm, greater than or equal to 7.5 cm, or greater than or equal to 10 cm. The average shortest distance between nearest neighbor markings in an unswollen conduit may be less than or equal to 20 cm, less than or equal to 10 cm, less than or equal to 7.5 cm, less than or equal to 5 cm, less than or equal to 4 cm, less than or equal to 3 cm, less than or equal to 2.5 cm, less than or equal to 2 cm, less than or equal to 1.5 cm, less than or equal to 1.25 cm, less than or equal to 1 cm, less than or equal to 0.75 cm, less than or equal to 0.5 cm, less than or equal to 0.2 cm, less than or equal to 0.1 cm, less than or equal to 50 mm, less than or equal to 10 mm, or less than or equal to 5 mm. Other ranges are also possible.

In some embodiments, the ranges described above may include catheter gauges (e.g., the French scale). For example, the average shortest distance between nearest neighbor markings may be greater than or equal to 3 Fr, greater than or equal to 5 Fr, greater than or equal to 10 Fr, greater than or equal to 15 Fr, greater than or equal to 20 Fr, or greater than or equal to 30 Fr. In some embodiments, the average shortest distance between nearest neighbor markings is less than or equal to 34 Fr, less than or equal to 30 Fr, less than or equal to 20 Fr, less than or equal to 15 Fr, less than or equal to 10 Fr, or less than or equal to 5 Fr. Combinations of the above-referenced ranges are also possible (e.g., greater than or equal to 3 Fr and less than or equal to 34 Fr). Other ranges are also possible.

The values in the preceding paragraphs may refer to features of conduits including a variety of amounts of water. Typically, the amount of water in the conduit in the swollen and/or second configuration is greater than the amount of water in the conduit in the unswollen and/or first configuration. In some embodiments, a conduit in an unswollen or first configuration has a water content of greater than or equal to 2 w/w %, greater than or equal to 5 w/w %, greater than or equal to 7.5 w/w %, greater than or equal to 10 w/w %, greater than or equal to 15 w/w %, greater than or equal to 20 w/w %, greater than or equal to 25 w/w %, greater than or equal to 30 w/w %, or greater than or equal to 35 w/w %. In some embodiments, a conduit in an unswollen or first configuration has a water content of less than or equal to 40 w/w %, less than or equal to 35 w/w %, less than or equal to 30 w/w %, less than or equal to 25 w/w %, less than or equal to 20 w/w %, less than or equal to 15 w/w %, less than or equal to 10 w/w %, less than or equal to 7.5 w/w %, or less than or equal to 5 w/w %. Combinations of the above-referenced ranges are also possible (e.g., greater than or equal to 2 w/w % and less than or equal to 40 w/w %, or greater than or equal to 20 w/w % and less than or equal to 40 w/w %). Other ranges are also possible.

In some embodiments, a conduit in a swollen or second configuration has a water content of greater than or equal to 3 w/w %, greater than or equal to 5 w/w %, greater than or equal to 7.5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, greater than or equal to 90 w/w %, greater than or equal to 95 w/w, greater than or equal to 98 w/w %, or greater than or equal to 99 w/w %. In some embodiments, a conduit in a swollen or second configuration has a water content of less than or equal to 99.9 w/w %, less than or equal to 99 w/w %, less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, less than or equal to 10 w/w %, less than or equal to 7.5 w/w %, or less than or equal to 5 w/w %. Combinations of the above-referenced ranges are also possible (e.g., greater than or equal to 3 w/w % and less than or equal to 99.5 w/w %, greater than or equal to 3 w/w % and less than or equal to 80 w/w %, greater than or equal to 40 w/w % and less than or equal to 80 w/w %). Other ranges are also possible. In some embodiments, the second or swollen state comprises an amount of water that is equivalent to the equilibrium water content of the conduit.

In some embodiments, a method comprises, with a marked catheter comprising markings that comprise multiple separate segments spaced along at least a portion of the catheter, wherein an average shortest distance between each segment and its nearest neighbor segment is a first distance in a first configuration of the marked catheter, performing the steps of: introducing a fluid to the marked catheter; and swelling at least a portion of the marked catheter from the first configuration to a second configuration, wherein the average shortest distance between each segment and its nearest neighbor segment in the second configuration becomes a second distance, and wherein a ratio of the second distance to the first distance is greater than or equal to 1.02:1 and less than or equal to 2:1.

In some embodiments, a method comprises, with a marked catheter comprising markings that comprise multiple separate segments spaced along at least a portion of the catheter, wherein an average shortest distance between each segment and its nearest neighbor segment is a first distance in a first configuration of the marked catheter, performing the steps of: introducing a fluid to the marked catheter; and swelling at least a portion of the marked catheter from the first configuration to a second configuration, wherein the average shortest distance between each segment and its nearest neighbor segment in the second configuration becomes a second distance, and wherein the second distance is equal to about 1 mm, about 10 mm, about 100 mm, about 1 cm, or about 10 cm.

In some embodiments, the method comprises swelling the polymeric material (and/or the catheter) to the equilibrium water content state. In some embodiments, the method comprises swelling the polymeric material (and/or the catheter) to the equilibrium water content state over a duration of time. In some embodiments the duration of time is less than or equal to 60 minutes (e.g., less than or equal to 10 minutes, less than or equal to 5 minutes, less than or equal to 1 minute, less than or equal to 30 seconds, or less than or equal to 10 seconds).

In some embodiments, the method comprises swelling the polymeric material (and/or the catheter) at a given temperature. In some embodiments, the temperature is greater than or equal to 4° C., greater than or equal to 10° C., greater than or equal to 16° C., greater than or equal to 20° C., greater than or equal to 25° C., or greater than or equal to 30° C. In some embodiments, the temperature is less than or equal to 40° C. less than or equal to 30° C., less than or equal to 25° C., less than or equal to 20° C., less than or equal to 16° C., or less than or equal to 10° C. Combinations of these ranges are also possible (e.g., 20° C.-40° C.).

In some embodiments, the method comprises swelling the polymeric material (and/or the catheter) such that the inner diameter and/or outer diameter increase by a larger percentage than the percentage increase in length (as described herein). For example, in some embodiments, the method comprises swelling the polymeric material such that the inner diameter and/or outer diameter increases by 1-20% while the length increases by 0.1-19%.

In some embodiments, the swelling occurs after administration. In some embodiments, the swelling of the polymeric material after administration into an orifice of a subject closes an opening of that orifice. For example, in some embodiments, the swelling of the polymeric material results in an increase in size to a dimension greater than or equal to the size of the orifice to which it is inserted. In some embodiments, the orifice is a wound. In some embodiments, the swelling of the polymeric material causes hemostasis. For example, in some embodiments, a subject (e.g., a human) may have an orifice (e.g., a wound) that has a maximum cross-sectional diameter of A and that is bleeding, and a device described herein with a maximum outer cross-sectional diameter smaller than A may be administered into the orifice. In some embodiments, the maximum outer cross-sectional diameter of the device may then swell to a dimension greater than or equal to A, such that the orifice is closed. In some embodiments, this may result in hemostasis.

In some embodiments, the swelling occurs before administration. In some embodiments, the swelling comprises rehydrating the device for a duration of time. In some embodiments, the duration of time is less than or equal to 60 minutes (e.g., less than or equal to 10 minutes, less than or equal to 5 minutes, less than or equal to 1 minute, or less than or equal to 10 seconds). In some embodiments, rehydrating the device comprises use of rehydration media. In some embodiments, the rehydration media comprises water, lactated Ringer's solution (LRS), dextrose (D5W), phosphate buffered saline (PBS), Hanks' Balanced Salt Solution (HBSS), and/or isotonic salt solutions.

In some embodiments, any markings present on a conduit may not undergo cracking or delamination when the conduit swells from the first configuration to the second configuration. The presence of cracking or delamination may be assessed by visual inspection of the swollen conduit by optical microscopy. For example, no delamination may be observed when exposed to alcohol/water sanitizing solutions like ethanol, isopropanol alcohol (70%/30% water), povvidone, chloraprep. (TD-082 reference).

Markings positioned on a conduit may penetrate to a variety of suitable depths from the surface thereof. In some embodiments, the markings penetrate into the conduit to a depth of greater than or equal to 0.1 microns, greater than or equal to 0.2 microns, greater than or equal to 0.5 microns, greater than or equal to 0.75 microns, greater than or equal to 1 micron, greater than or equal to 2 microns, greater than or equal to 5 microns, greater than or equal to 7.5 microns, greater than or equal to 10 microns, greater than or equal to 20 microns, greater than or equal to 30 microns, greater than or equal to 40 microns, greater than or equal to 50 microns, greater than or equal to 60 microns, greater than or equal to 70 microns, greater than or equal to 80 microns, greater than or equal to 100 microns, greater than or equal to 125 microns, greater than or equal to 150 microns, greater than or equal to 175 microns, greater than or equal to 200 microns, greater than or equal to 250 microns, greater than or equal to 300 microns, greater than or equal to 400 microns, greater than or equal to 500 microns, greater than or equal to 750 microns, greater than or equal to 1 mm, greater than or equal to 2 mm, greater than or equal to 5 mm, or greater than or equal to 7.5 mm. In some embodiments, the markings penetrate into the conduit to a depth of less than or equal to 10 mm, less than or equal to 7.5 mm, less than or equal to 5 mm, less than or equal to 2 mm, less than or equal to 1 mm, less than or equal to 750 microns, less than or equal to 500 microns, less than or equal to 400 microns, less than or equal to 300 microns, less than or equal to 250 microns, less than or equal to 200 microns, less than or equal to 175 microns, less than or equal to 150 microns, less than or equal to 125 microns, less than or equal to 100 microns, less than or equal to 80 microns, less than or equal to 70 microns, less than or equal to 60 microns, less than or equal to 50 microns, less than or equal to 40 microns, less than or equal to 30 microns, less than or equal to 20 microns, less than or equal to 10 microns, less than or equal to 7.5 microns, less than or equal to 5 microns, less than or equal to 2 microns, less than or equal to 1 micron, less than or equal to 0.75 microns, less than or equal to 0.5 microns, or less than or equal to 0.2 microns. Combinations of the above-referenced ranges are also possible (e.g., greater than or equal to 0.1 micron and less than or equal to 10 mm, greater than or equal to 10 microns and less than or equal to 200 microns, or greater than or equal to 50 microns and less than or equal to 60 microns). Other ranges are also possible.

Markings 112 can be applied to at least a portion of conduit 101 in a variety of suitable manners. In some embodiments, markings are formed by disposing a markings composition on at least a portion of the surface of the conduit. Suitable markings compositions are described elsewhere herein. One suitable manner of disposing markings on at least a portion of a conduit surface is ink-jet printing, described elsewhere herein. The markings may also be deposited by liquid deposition, pad printing, screen printing, electrostatic spraying, hot stamping, laser etching, and/or dip coating.

The markings described herein may comprise any suitable size and shape. In some embodiments, the markings comprise a shape, a letter, a number, a combination of letters and/or numbers, logos, and images. Non-limiting examples of suitable shapes include lines, zig-zag, squares, rectangles, circles, ovals, polygons (e.g., pentagons, hexagons, heptagons, octagons, nonagons, dodecagons, or the like), tubes, rings, star or star-like/stellate (e.g, 3-armed stars, 4-armed stars, 5-armed stars, 6-armed stars, 7-armed stars, 8-armed stars), and the like. In an exemplary set of embodiments, the markings comprise a combination of lines and numbers (e.g., delineating a length along the article). In another exemplary set of embodiments, the markings comprise a logo and/or image (e.g., for identifying the article and/or the manufacturer of the article). Other markings are also possible.

Figure 3:
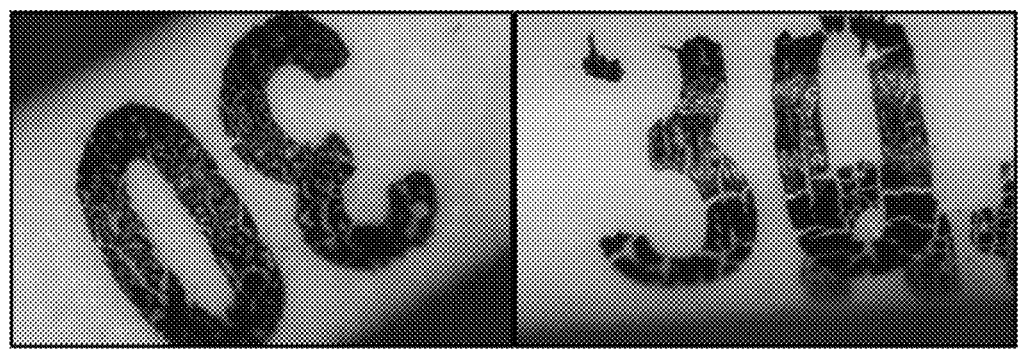
FIGS. 3-7 shows photographs of dry catheters and catheters after hydration in phosphate buffered saline, consistent with some embodiments.

Another example of a suitable method for applying markings to a conduit is doing so via pad printing. Applicant conducted studies to evaluate the durability of two 1-part pad printing ink resins: Tampa® Pur 980 Black TPU and Tampa® Star 980 Black TPR, both by Marabu GmbH & Co. Applicant applied each ink to extruded to extruded segments (e.g. conduit 101) comprising polymeric material 20 comprising at least poly(vinyl alcohol) (PVA) and after soaking in a non-solvent bath, as described herebelow in reference to STEP 1270 of FIG. 14, but prior to soaking in a hydrophilic bath, as described herebelow in reference to STEP 1350 of FIG. 15. Applicant observed each ink adhered well to the extruded segment in a dry state. However, after approximately 15 minutes of hydration in 1× phosphate-buffered saline (PBS) at a temperature between 20° C. and 25° C. (e.g. room temperature), the extruded segment swelled and the inks cracked as shown in FIG. 3.

Figure 4:
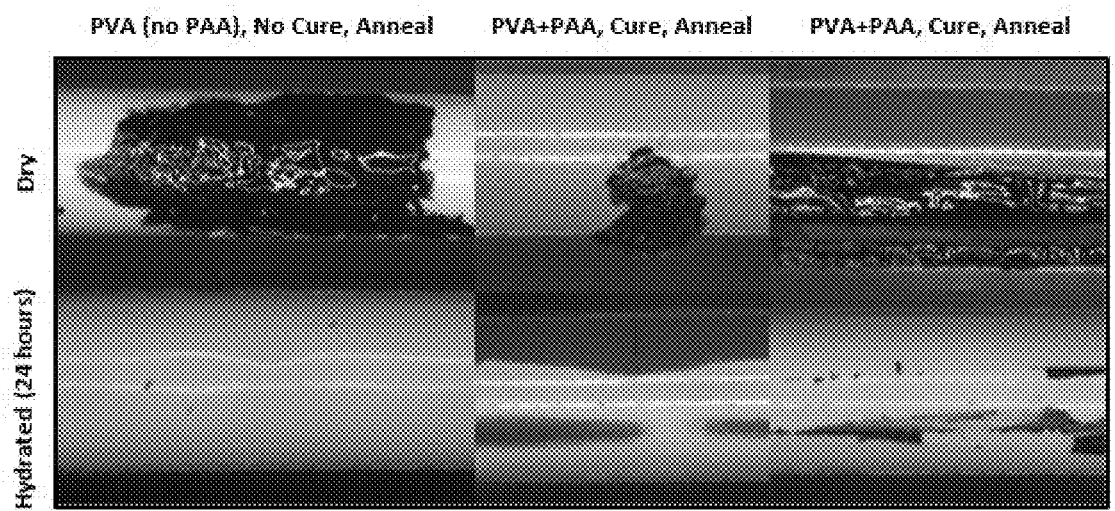

Markings 112 can be applied to at least a portion of conduit 101 via UV-curable pad printing. Applicant conducted studies to evaluate the durability of a UV-curable pad printing ink: Series 747 PC Lot #747-8005 by Deco Technology Group, Inc. Applicant applied each ink to extruded segments (e.g. conduit 101) comprising polymeric material 20 comprising at least poly(vinyl alcohol) (PVA). Specifically, applicant evaluated the durability of the UV-curable inks as applied to: extruded segments comprising PVA; and extruded segments comprising PVA and after soaking in a hydrophilic bath comprising a poly(acrylic acid) solution (PAA), as described herebelow in reference to STEP 1350 of FIG. 15. Applicant allowed the ink to dry at a temperature between 20° C. and 25° C. (e.g. room temperature) for approximately two hours. Subsequently, the extruded segments were transferred to a UV-sterilizer to cure for approximately four hours. In some embodiments, the extruded segments were further annealed as described herebelow in reference to Method 1400 of FIG. 9. In other embodiments, the extruded segments were not annealed. Applicant inspected each extruded segment in a dry state and a hydrated state, as shown in FIG. 4. Applicant observed the ink delaminated from the surface of each extruded segment after hydration in 1×PBS. Additionally, applicant observed the extruded segments comprising PAA also exhibited a significant discoloration after exposure to the UV-sterilizer.

Figure 5:
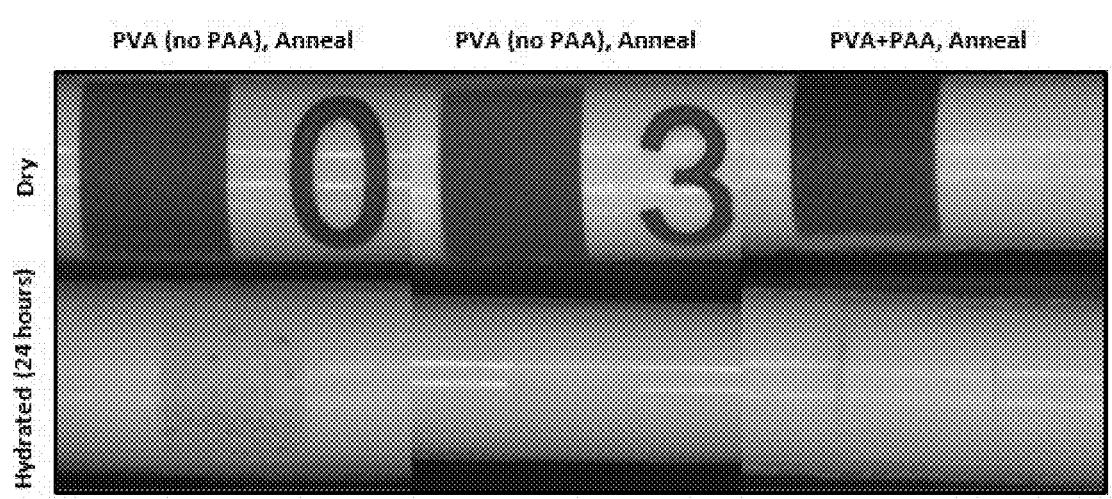

Markings 112 can be applied to at least a portion of conduit 101 via laser etching. Applicant conducted studies to evaluate the durability of a one-axis 355 nm diode pumped solid state laser etching. Applicant etched black bands and numbers onto the surface of extruded segments (e.g. conduit 101) comprising polymeric material 20 comprising at least poly(vinyl alcohol) (PVA). Specifically, applicant evaluated the durability of the laser etching as applied to: extruded segments comprising PVA; and extruded segments comprising PVA and after soaking in a hydrophilic bath comprising a poly(acrylic acid) solution (PAA), as described herebelow in reference to STEP 1350 of FIG. 8. Applicant allowed the ink to dry for approximately two hours at a temperature between 20° C. and 25° C. (e.g. room temperature). In some embodiments, the extruded segments were further annealed as described herebelow in reference to Method 1400 of FIG. 16. In other embodiments, the extruded segments were not annealed. Applicant inspected each extruded segment in a dry state and a hydrated state, as shown in FIG. 5. Applicant observed the laser etching sloughed off from the surface of each extruded segment after hydration in 1×PBS for 24 hours at 37° C.

Figure 6:
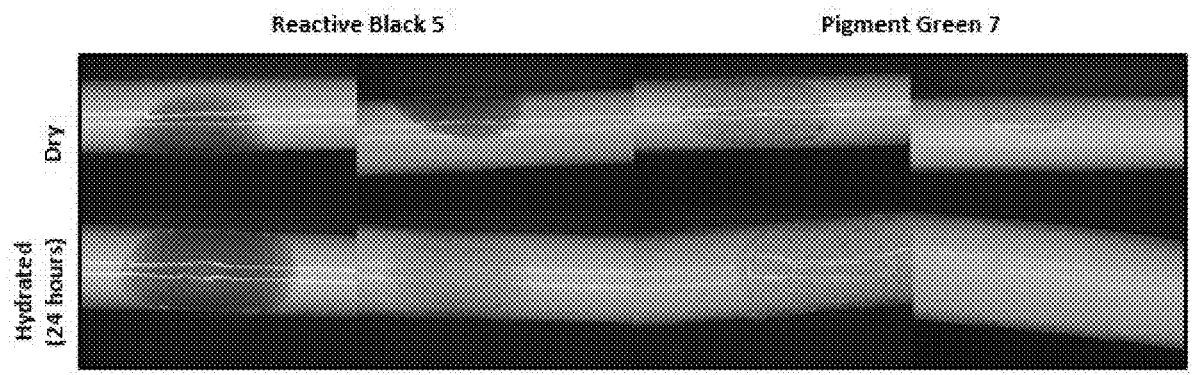

Markings 112 can be applied to at least a portion of conduit 101 via a poly(vinyl alcohol)-based ink. Applicant conducted studies to evaluate the durability of two custom PVA-based inks: an ink comprising 0.01 w/w % Reactive Black 5 (CAS #17095-24-8) in a 15 w/w % mixture of 28-99 PVA in 1×PBS and an ink comprising 0.01 w/w % Pigment Green 7 (CAS #14832-14-5) in a 10 w/w % mixture of 28-99 PVA in 1×PBS. Applicant applied each ink to extruded segments (e.g. conduit 101) comprising polymeric material 20 comprising at least poly(vinyl alcohol) (PVA). Specifically, applicant evaluated the durability of the PVA-based inks as applied to: extruded segments comprising PVA; and extruded segments comprising PVA and after soaking in a hydrophilic bath comprising a poly(acrylic acid) solution (PAA), as described herebelow in reference to STEP 1350 of FIG. 15. Applicant allowed the inks to dry under ambient conditions for approximately one hour. In some embodiments, the extruded segments were further annealed as described herebelow in reference to Method 1400 of FIG. 16. In other embodiments, the extruded segments were not annealed. Applicant inspected each extruded segment in a dry state and a hydrated state, as shown in FIG. 6. Applicant observed the inks adhered well to the extruded segments that did not comprise PAA, whereas the inks did not adhere well and delaminated from the extruded segments comprising PAA. Additionally, applicant observed an ingress of the Reactive Black 5 ink into the body of the extruded segments. Each extruded segment exhibited delamination after approximately 24 hours of hydration in 1×PBS.

Figure 7:
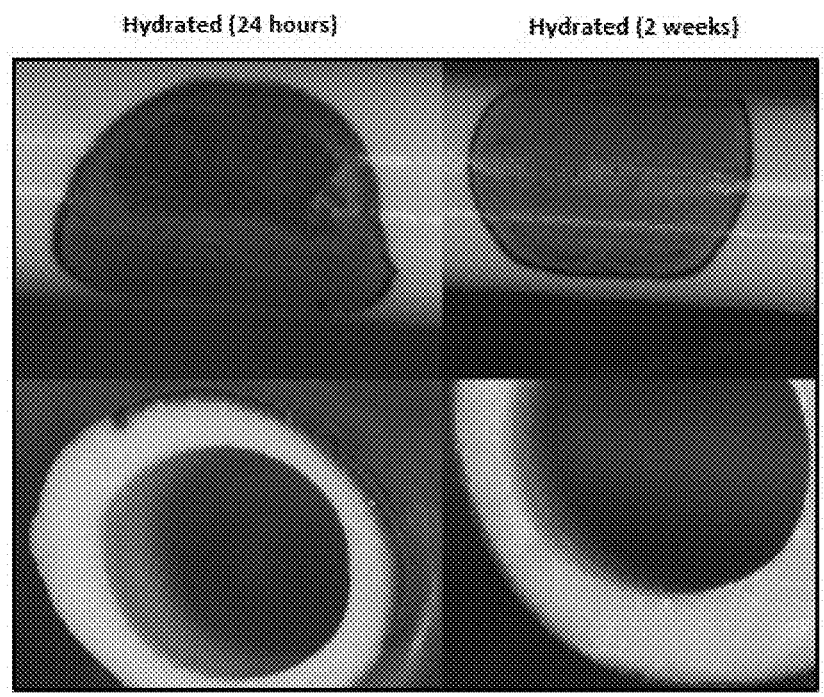

Markings 112 can be applied to at least a portion of conduit 101 via dye impregnation with an aqueous solution. Applicant conducted studies to evaluate the durability of a custom dye solution comprising 0.01 w/w % Reactive Black 5 (CAS #17095-24-8) in distilled water. Applicant applied each ink to extruded segments (e.g. conduit 101) comprising polymeric material 20 comprising at least poly(vinyl alcohol) (PVA). Specifically, applicant evaluated the durability of the dye as applied to extruded segments comprising PVA and after soaking in a hydrophilic bath comprising a poly (acrylic acid) (PAA) solution, as described herebelow in reference to STEP 1350 of FIG. 15. Applicant allowed the dye to dry under ambient conditions. Applicant then transferred the extruded segments to a convection oven for a three hour drying and a 90 minute annealing at 150° C. Applicant inspected each extruded segment in two hydrated states, as shown in FIG. 7. The extruded segments were hydrated in 1×PBS for 24 hours at 37° C. and in 1×PBS for two weeks at 55° C. Applicant observed adhesion and ingress of the dye into the body of the extruded segments. Additionally, applicant observed the dye was retained within the extruded segments after two weeks of hydration.

Markings 112 can be applied, in some embodiments, to at least a portion of conduit 101 via dye impregnation with a solvent solution. Applicant conducted studies to evaluate the durability of a custom dye solution comprising 0.01 w/w % Reactive Black 5 (CAS #17095-24-8) in a Carbopol® (PAA) solution. Applicant applied each ink to extruded segments (e.g. conduit 101) comprising polymeric material 20 comprising at least poly(vinyl alcohol) (PVA). Specifically, applicant evaluated the durability of the dye as applied to extruded segments comprising PVA and after soaking in a hydrophilic bath comprising a poly(acrylic acid) (PAA) solution, as described herebelow in reference to STEP 1350 of FIG. 15. Applicant allowed the dye to dry under ambient conditions. Applicant then transferred the extruded segments to a convection oven for a three hour drying and a 90 minute annealing at 150° C. The extruded segments were hydrated in 1×PBS for 24 hours at 37° C. Similar to the results as shown in FIG. 7, applicant observed adhesion and ingress of the dye into the body of the extruded segments.

Markings 112 can be applied, in some embodiments, to at least a portion of conduit via hot stamping. The hot stamping process involves a die and occasionally a hot stamping foil or pre-dried ink. For example, the die is heated and pressed onto the foil or pre-dried ink transferring the ink to the conduit.

Figure 23A:
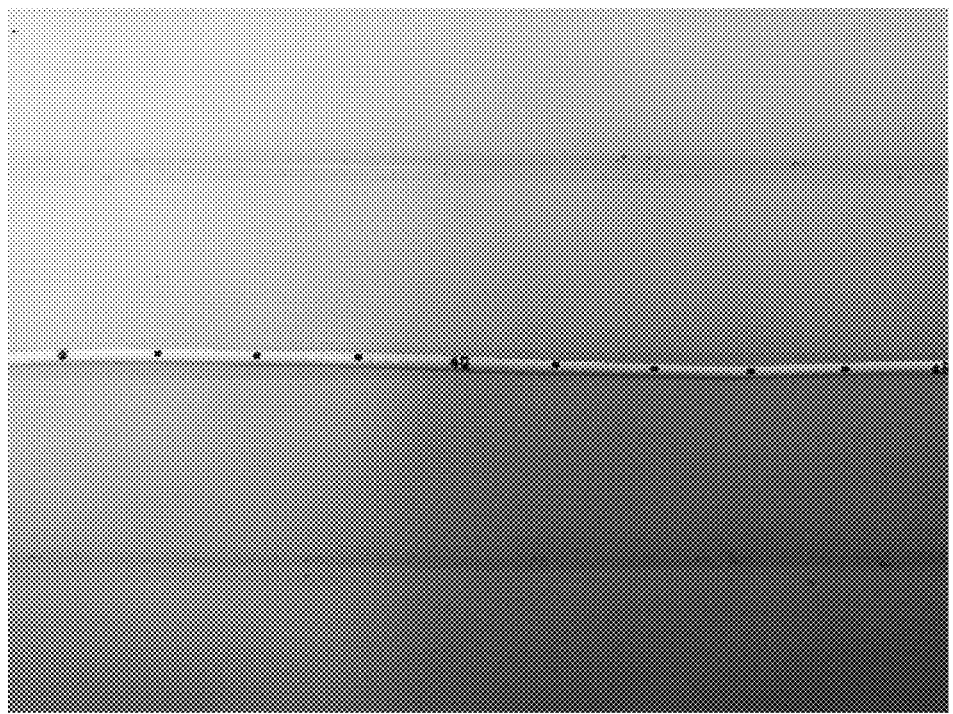
FIGS. 23A-23B show photographs of exemplary marked catheters, according to some embodiments.
Figure 23B:
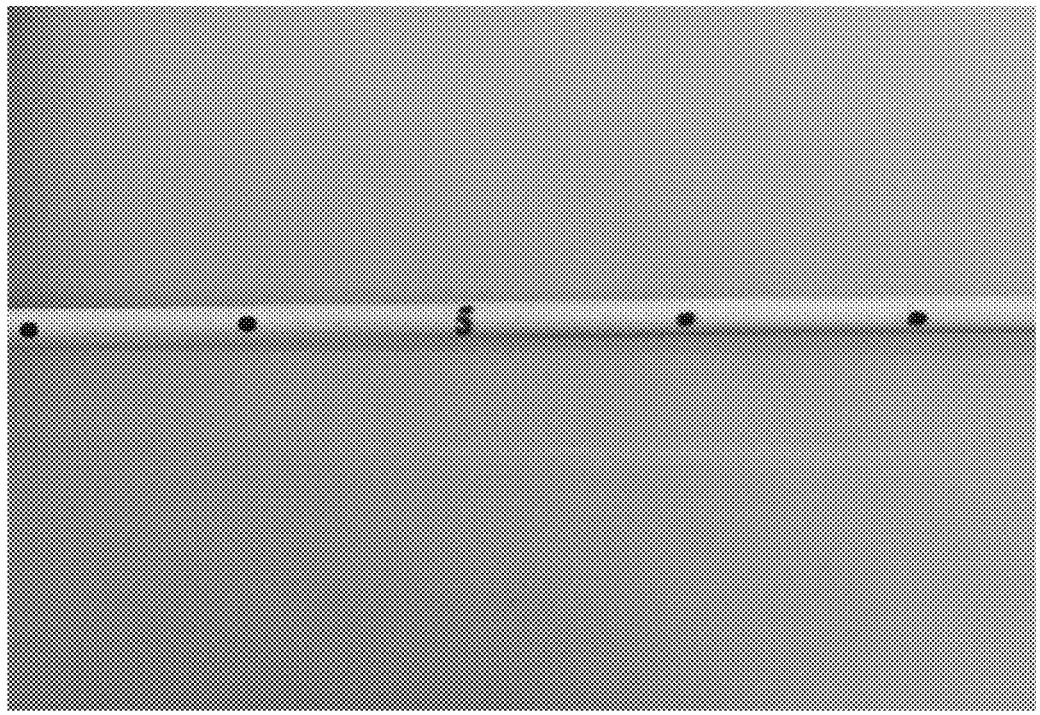

Markings 112 can be applied, in some embodiments, to at least a portion of conduit via ink-jet printing. Applicant conducted a study using a custom dye solution comprising of poly(vinyl alcohol), copper phthalocyanine, and water. Applicant applied the custom dye to the extruded segment using a system capable of projecting a jet of ink. The system dispenses the ink using an electrically operated piezo-actuated dispensing valve. The system is pressurized via compressed air, a program dictates how long to open (Pulse) and amount of time between deposits (Cycle) to the piezo-actuated dispensing valve. The system is capable of dispensing ink in a wide range of geometries. Applicant placed markings onto an extruded segment using a Pulse of 0.30 ms, Cycle from 18.0-21.0 ms and pressure 3-15 psi. The marked extruded segments were subsequently dried at 95° C. for 6 hrs. A rub test defined in TD-082 Rev A was performed on the marked section of extrusions over a period of 123 days. The results of the study concluded that the ink and method of application was sufficient for placing and adhering markings to extruded sections of extrusions. An exemplary marked catheter is shown in FIG. 23A and FIG. 23B.

Device 100 can include one, two, or more patient fixation devices, such as suture wing 160 shown. Conduit 101 and suture wing 160 can comprise a similar hardness and/or compliance. For example, suture wing 160 can comprise a 42% poly(vinyl alcohol) 28-99, deionized water slurry that was injection molded (e.g. at 96° C.) into a suture wing shape, and subsequently dried (e.g. at 55° C. for 6 hours). Suture wing 160 can be dehydrated such as to cause a volumetric change of −52% (or approximately the water content of the initial injection molded material) to match a hardness of conduit 101. As another example, suture wing 160 can comprise an 18% poly(vinyl alcohol) 28-99, 0.9% sodium chloride solution slurry that was injected molded (e.g. at 96° C.) into a suture wing shape and dried (e.g. at 55° C. for 6 hours). The dehydration of suture wing 160 can cause a volumetric change of −81% to suture wing 160, such as to match a hardness of conduit 101. Similarly, suture wing 160 can be heat treated at 150° C. for 90 minutes, and can undergo a volumetric change of −81%, such as to match a hardness of conduit 101. As another example, suture wing 160 can comprise a thermoplastic or thermosetting material configured to not exhibit a volumetric change upon exposure to an aqueous solution.

Device 100 can include one or more linear elements, linear element 123 shown. Linear element 123 can comprise a needle, guidewire, stylet, or other elongate filament that is inserted into lumen 106 of conduit 101, such as to straighten a conduit 101 that is resiliently biased in a non-linear geometry, such as is described herebelow in reference to FIG. 8.

Device 100 can include one or more accessories, accessory 170 shown. In some embodiments, accessory 170 comprises a tubing clamp, such as clamp 170a described herebelow in reference to FIGS. 4A-B.

Device 100 can include packaging, packaging 180, into which the other components of device 100 (e.g. at least conduit 101) are packaged, sterilized, and shipped to a clinical site for insertion into a patient. Packaging 180 can include a flexible container that includes flashspun high-density polyethylene fibers. In some embodiments, packaging 180 further includes a tray into which device 100 is positioned for shipment.

Device 100 can include one or more sensors, transducers, and/or other functional elements, such as functional element 199 described herebelow. Functional element 199 can comprise one or more functional elements positioned on and/or within conduit 101 (as shown), connector 120, band 122, suture wing 160, and/or another component of device 100. Functional element 199 can be connected to one or more wires, optical fibers, tubes (e.g. fluid delivery, hydraulic, and/or pneumatic tubes), wave guides, and/or other conduits (not shown) that transport signals (e.g. information), energy, fluid, light, and/or sound to and/or from functional element 199 from and/or to another component (e.g. another component of system 10). In some embodiments, system 10 includes functional device 999 which is configured to interface with functional element 199, as described herebelow.

Extruder 500 can be constructed and arranged to produce conduit 101 comprising polymeric material 20, as described herebelow. Extruder 500 can comprise a die-head 502, an auger 504, and a screw 506. Extruder 500 can be configured to produce conduit 101 comprising a fixed cross-sectional profile, such that polymeric material 20 is pushed through die-head 502 comprising the desired cross-section. Die-head 502 can comprise a disk with an opening constructed and arranged with the size and shape of the intended cross-section of conduit 101. Auger 504 can be configured to rotate adjacent to extruder 500, such as to move polymeric material 20 into extruder 500 and towards screw 506. Screw 506 can be configured to rotate within extruder 500, such as to move polymeric material 20 towards die-head 502 for extrusion.

In some embodiments, extruder 500 comprises a single screw extruder, such as an extruder comprising a ¾ inch diameter, a 25:1 L/D, and a 1:1 compression ratio.

System 10 can further comprise one or more mixing devices, device 602 shown, configured to combine two or more substances to form an acceptable mixture of material (e.g. a sufficiently mixed combination of materials, such as to form polymeric material 20). In some embodiments, mixing device 602 comprises a high speed dual asymmetric centrifuge. In some embodiments, the mixture is heated in a sealed or vented jar to a temperature below the boiling point of a soaking solution and mixed in a dual asymmetric centrifuge at speeds up to 3500 rpm until homogenously mixed. In some embodiments, the mixture is heated to a temperature below the boiling point of a soaking solution and mixed with an agitator, ribbon blender, paddle mixer, static mixer, emulsifier, homogenizer, and/or drum mixer until homogenously mixed.

System 10 can further comprise one or more tube pullers, puller 604 shown, configured to aid in the advancement of a material (e.g. polymeric material 20) through an extrusion device (e.g. extruder 500). In some embodiments, tube puller 604 comprises One or more conveying belts can be positioned downstream of the die-head 502 and can be configured to move conduit 101 in a controlled manner away from extruder 500. In some embodiments, tube puller 604 is configured to operate in a controlled manner to maintain a uniform outer diameter of conduit 101 as it is conveyed. In some embodiments, tube puller 604 is configured to selectively increase or decrease the outer diameter of one, two, or more segments of conduit 101. In some embodiments, tube puller 604 is configured to pull conduit 101 at a speed configured to impart a polymer chain orientation.

System 10 can further comprise one or more vessels, trough 606 shown, comprising an open topped elongate vessel within which an object (e.g. polymeric material 20) can be at least partially immersed. Trough 606 can be filled or at least partially filled ("filled" herein) with one or more fluids, solution 630 (e.g. alcohol solution, hydrophilic polymer solution, hydrophobic polymer solution). In some embodiments, trough 606 comprises a closed elongate vessel containing one or more fluids (e.g. solution 630), maintained under a vacuum.

System 10 can further comprise one or more drying systems, dryer 608 shown, comprising a manifold configured to apply a gas across the surface of an object (e.g. polymeric material 20). Dryer 608 can apply a gas configured to extract a solvent from the surface of the object. Dryer 608 can apply a gas selected from the group consisting of: oxygen; nitrogen; argon; and combinations of these. Dryer 608 can be configured to apply at least one of an ambient gas, a heated gas, and a chilled gas.

System 10 can further comprise one or more vessels for soaking components, chamber 618 shown, within which an object (e.g. conduit 101) can be at least partially immersed in a fluid and/or a semi-fluid, such as solution 630 described herein. In some embodiments, a trough 606 comprises chamber 618 (e.g. a trough 606 and chamber 618 comprise the same component of system 100).

As described hereabove in reference to trough 606 and chamber 618, system 10 can further comprise one or more solutions, solution 630, shown. As used herein, one, two or more of solutions 631-635 are referred to generally as solution 630. Trough 606 and/or chamber 618 can be filled with solution 630, such as to expose one or more components of device 100 and/or system 10 to the solution 630. Solution 630 can comprise a homogenous mixture comprising two or more substances. In some embodiments, trough 606 is filled with a solution 630 comprising a solution selected from the group consisting of: water; ethanol; methanol; propanol; butanol; and combinations of these.

In some embodiments, solution 630 further comprises a poly(acrylic acid) solution, solution 631.

In some embodiments, solution 630 further comprises a buffer solution, solution 632.

In some embodiments, solution 630 further comprises a polymer solution, solution 633. Solution 630 can comprise a hydrophilic and/or hydrophobic polymer solution 633 configured to penetrate polymeric material 20 to provide enhanced hydrophilicity and/or enhanced non-thrombogenic properties. In some embodiments, trough 606 is filled with a solution 630 comprising a hydrophilic polymer solution 633 selected from the group consisting of: poly(vinyl alcohol); poly(acrylic acid); polyethylene glycol; poly(vinyl pyrrolidone); poly(methacrylic sulfobetaine); poly(acrylic sulfobetaine); poly(methacrylic carboxybetaine); poly (acrylic carboxybetaine); povidone polyacrylamide; poly(N-(2-hydroxypropyl)methacrylamide); polyoxazolines; polyphosphates; polyphosphazenes; polyvinyl acetate; polypropylene glycol; poly(N-isopropylacrylamide); poly (2-hydroxymethylmethacrylate); and combinations of these. In some embodiments, trough 606 is filled with a solution 630 comprising a hydrophobic polymer solution 633 selected from the group consisting of: polyurethanes; silicones; polybutadienes; styrene-butadiene copolymers; natural rubbers; and combinations of these.

In some embodiments, solution 630 comprises a dye, dye 634.

In some embodiments, solution 630 comprises a surfactant solution, solution 635. Solution 630 can comprise a surfactant solution 635 comprising a humectant. The humectant may comprise a non-ionic surfactant (i.e., a surfactant having an uncharged hydrophilic head and a hydrophobic tail) or a zwitterionic surfactant (i.e., a surfactant having a net uncharged hydrophilic head and a hydrophobic tail). In some embodiments, the humectant is a non-ionic surfactant selected from the group consisting of: poloxamer; triacetin; α-hydroxy acids; poly(ethylene glycol); poly(propylene glycol); glycerol; propylene glycol; ethylene glycol; butylene glycol; hexylene glycol; glycerol; erythritol, threitol; arabitol; xylitol; ribitol; mannitol; sorbitol; galactitol; fucitol; iditol; inositol; volemitol; malitol; lactitol; maltotriitol; maltotetraitol; polyglycitols; and combinations of these. In some embodiments, the humectant comprises an oil, such as vitamin E. Some humectants may comprise one or more salts (e.g., sodium chloride, potassium chloride, and/or phosphocholine)

System 10 can further comprise a non-solvent bath 612 within which an object (e.g. conduit 101) can be at least partially immersed in a non-solvent solution. Non-solvent bath 612 can comprise a non-solvent solution selected from the group consisting of: ethanol; methanol; propanol; butanol; pentanol; hexanol; heptanol; octanol; decanol; dodecanol; dimethyl sulfoxide; ethyl acetate; acetates; propionates; ethers; dimethyl formamide; dimethyl acetamide; acetone; acetonitrile; ethylene glycol; propylene glycol; glycerol, air; and combinations of these.

System 10 can further comprise one or more mandrels, mandrel 614 shown, which can be configured to be slidingly inserted into an object having a lumen therethrough (e.g. conduit 101 via lumen 106). In some embodiments, mandrel 614 comprises a non-stick surface, such as a polytetrafluoroethylene, parylene, and/or phenolic coated surface.

Mandrel 614 can be configured to impart one, two, or more geometric features to the object (e.g. conduit 101). In some embodiments, mandrel 614 comprises a taper. In some embodiments, mandrel comprises a non-linear shape, such as a curved or bent shape. In some embodiments, mandrel 614 comprises a non-cylindrical cross-section.

Mandrel 614 can comprise a textured surface. In some embodiments, mandrel 614 imparts the texture onto the object's inner diameter (e.g. surface of the lumen). The textured surface can be configured to reduce flow resistance within the object's lumen by causing turbulence around the fluid film layer. The textured surface can be configured to reduce resistance and pressure within the object's lumen from high flow environments, such as power injection comprising a flow rate between 3 mL/s and 10 mL/s.

System 10 can further comprise one or more filaments, filament 608 shown, around which a material (e.g. polymeric material 20) can be formed or otherwise deposited. In some embodiments, a mandrel 614 comprises filament 608.

System 10 can further include one or more clamps, clamp 200 shown, configured to attach one component of system 10 to another. Clamp 200 can comprise one or more clamps as described herebelow in reference to FIGS. 3A-C.

System 10 can further include hydrating equipment, hydration device 300. Hydration device 300 can include a tube or other vessel, overtube 301 shown, which can be at least partially filled ("filled" herein) with hydration media, fluid 365 shown. Fluid 365 can comprise one or more materials (e.g. one or more solutions or other fluids) used to hydrate one or more portions of device 100 (e.g. all or a portion of conduit 101) positioned in overtube 301 (prior to and/or after filling of overtube 301 with fluid 365). In some embodiments, fluid 365 comprises multiple different fluids 365, such as fluid 365a, 365b, and/or 365c shown. Hydration device 300 can further include one or more fluid reservoirs, fluid reservoir 360, used to store one, two, or more fluids 365 prior to performing the hydration process (e.g. prior to shipping hydration device 300 to a clinical site). Fluid reservoir 360 can comprise one, two, or more fluid sources selected from the group consisting of: syringe; gravity-driven fluid bag; fluid pump (e.g. with reservoir); and combinations of these. In some embodiments, two or more fluid reservoirs 360 comprise two or more different fluids 365.

Figure 11A:
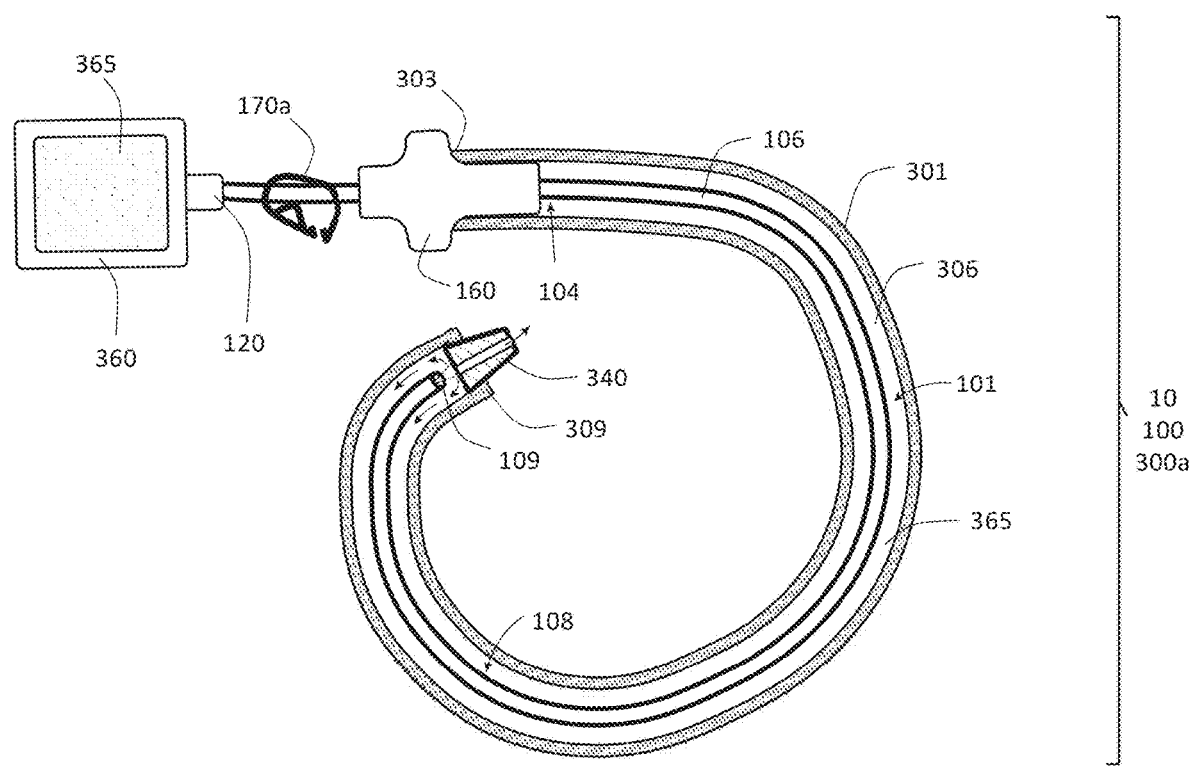
FIGS. 11A-B illustrate perspective views of hydration devices for hydrating a conduit, consistent with some embodiments.

Hydration device 300 can be configured similar to hydration device 300a and/or 300b described herebelow in reference to FIGS. 11A and 4B, respectively.

The hydration fluid 365 can comprise sterile material or material to be sterilized. Hydration fluid 365 can comprise one, two, three, or more materials selected from the group consisting of: a humectant; saline; lactated ringer's solution; dextrose; water for injection (WFI); custom isotonic salt solution; a poloxamer; glycerol; sorbitol; xylitol; polyethylene glycol; starch; heparin; and combinations of these. Fluid 365 can be provided at a specific pH, temperature, and/or volume. In some embodiments, hydration fluid 365 comprises sterile normal saline (isotonic) at body temperature (e.g. 37° C.).

Hydration device 300 can be configured to provide a water content (e.g. hydration) of device 100 that is maintained during storage and/or transportation.

In some embodiments, hydration can be performed using hydration device 300 or otherwise to increase the size of lumen 106 of conduit 101. In some embodiments, conduit 101 and hydration device 300 are configured to increase the diameter of the size of lumen 106 from 0-25% between the dehydrated and the rehydrated state.

In some embodiments, during the manufacturing process one or more portions of device 100 (e.g. all or a portion of conduit 101) are dehydrated and/or annealed in a stressed state, such that subsequent hydration performed using hydration device 300 or otherwise causes anisotropic swelling. In some embodiments, conduit 101 and hydration device 300 are configured to allow for swelling of conduit 101 only in the axial direction, such that the outer diameter and lumen 106 diameter are maintained to allow a physician to better match the size of conduit 101 to a site for insertion. In some embodiments, conduit 101 and hydration device 300 are configured to allow for swelling of conduit 101 only in the radial direction, such that the length of conduit 101 is unchanged to allow for precise placement of the proximal and/or distal end of conduit 101 and to allow for radial swelling of conduit 101 to seal the insertion site and/or decrease the pressure drop across conduit 101.

In some embodiments, during the manufacturing process one or more portions of device 100 are lyophilized while the one or more portions (e.g. conduit 101) is in a swollen state, such that dimensions of included pores, and/or other dimensions, of the lyophilized portions are not significantly changed when a subsequent hydration procedure is performed (e.g. using hydration device 300).

In some embodiments, one or more hydration devices 300 are used to perform multiple hydrations of device 100, such as one or more hydrations performed during manufacturing, and/or one or more hydrations performed at the procedure site just prior to insertion of conduit 101 into the patient. In these embodiments, two or more hydrations can be performed using a different fluid 365. In some embodiments, hydration device 300 comprises a fluid 365 configured to hyperswell conduit 101, such as a fluid 365 comprising a low pH aqueous solution, a hypotonic solution, and/or or a solution at a temperature above body temperature (e.g. 37° C.) but below the $T_g$ of the polymeric material. A second hydration device 300 can include an isotonic solution at body temperature (e.g. 37° C.) configured to neutralize conduit 101 and maintain the desired level of swell.

In some embodiments, device 100 comprises one or more hydration devices 300. In these embodiments, device 100 can be packaged with hydration device 300, such as when all or a portion of conduit 101 is positioned within overtube 301 of hydration device 300 in a shipping container, packaging 180. The arrangement may simplify a hydration process to be performed at the procedure site. In some embodiments, device 100 is shipped in a pouch or other storage container, packaging 180, and reservoir 360 including fluid 365 is also included in the storage container. In these embodiments, reservoir 360 can comprise a pouch or other vessel configured to be ruptured or otherwise opened (e.g. at the procedure site) while within packaging 180, allowing fluid 365 to surround and hydrate device 100 prior to opening packaging 180.

In some embodiments, hydration device 300 and system 10 are configured to perform a hydrophilic polymer incorporation procedure at an elevated temperature, such as at a temperature above body temperature (e.g. above 37° C.). In these embodiments, conduit 101 can be configured to "hyperhydrate" or "hyperswell", such as to incorporate additional agents relative to swelling observed at body temperature. In some embodiments, an elevated temperature hydration procedure is performed to incorporate an agent comprising one or more plasticizers, humectants, and/or hydrophilic polymers (e.g. one or more additional plasticizers, humectants, and/or hydrophilic polymers) as described hereabove Any hydration steps that are performed (e.g., an initial hydration step, a subsequent hydration step) can be performed for an amount of time that may be selected as desired. In some embodiments, a hydration step is performed relatively quickly (e.g., for a period of time of less than or equal to 10 minutes).

System 10 can further comprise an air blade 610 configured to blow off, or otherwise remove, a solution, solvent, volatile, and/or other matter from the surface of an object (e.g. conduit 101).

System 10 can further comprise one or more holding fixtures, rack 622, for maintaining one or more conduits 101 and/or one or more components of conduit 101 (generally "conduit 101") in a desired position. Rack 622 can comprise upper rack 622a (shown), lower rack 622b (also shown), and/or other racks 622, each comprising a framework, stand, or grating on which an object (e.g. conduit 101) is placed and/or attached.

System 10 can further comprise one or more temperature controlled environmental chambers, oven 620 shown. Oven 620 can comprise a thermally insulated chamber configured for heating and/or drying of an object (e.g. conduit 101). In some embodiments, oven 620 comprises a convection oven. In some embodiments, oven 620 is configured to extract or otherwise remove a material (e.g. solvent, water, etc.) from an object. In some embodiments, oven 620 comprises a chamber in which both temperature and pressure can be controlled. In some embodiments, oven 620 comprises a chamber in which humidity can also be controlled. In some embodiments, oven 620 comprises a chamber in which a gas (e.g. air, nitrogen, argon, etc.) can be purged.

Device 100 can include a circumferential (or partial circumferential) securing element, band 122 shown, which can be configured to secure connector 120 to conduit 101. For example, connector 120 can comprise a barbed or other elongate end portion which is inserted (e.g. during a manufacturing process) into lumen 106 at an end of conduit 101. Band 122 can be positioned about conduit 101 at a location surrounding or at least proximate ("surrounding" herein) the inserted end portion of connector 120, securing connector 120 to conduit 101. Band 122 can be configured to provide a fluid seal between the connector 120 and conduit 101. Band 122 can comprise a material configured to contract upon heating, such as heat shrink tubing that is positioned to surround conduit 101 and an inserted end portion of connector 120, and subsequently heated to cause a radial contraction (shrinking) to secure connector 120 to conduit 101. In some embodiments, band 122 comprises heat shrink tubing configured to contract at a temperature between 120° C. and 350° C. Band 122 can comprise a material selected from the group consisting of: polytetrafluoroethylene; fluorinated ethylene propylene; perfluoroalkoxy copolymer; ethylene tetrafluoroethylene; polyethylene terephthalate; polyetheretherketone; polyether block amide; poly(vinyl chloride); polyethylene; polyolefin; and combinations of these. In some embodiments, band 122 comprises a material configured to be elastically stretched (e.g. radially expanded via a tool to an increased diameter) and positioned about an end of conduit 101. Band 122 is then released and allowed to transition back to a smaller diameter resiliently biased condition that provides the desired attachment of band 122 to conduit 101. In some embodiments, band 122 comprises a material configured to be plastically deformed via radial compression, the resultant reduced diameter configured to create the secure connection of connector 120 to conduit 101. In some embodiments, band 122 comprises a material configured to be radially expanded by exposure to a chemical (e.g. a solvent), and subsequently positioned about a conduit 101 at a location surrounding an inserted end portion of connector 120. Removal of the chemical (e.g. via evaporation or other means) causes a radial contraction of the band 122 to provide the desired secure connection.

System 10 can further comprise one or more marking devices, device 616 shown. The marking device may be employed to dispose markings on a surface of a conduit. In some embodiments, marking device 616 comprises a laser, such as a solid-state laser. In some embodiments, marking device 616 comprises a pad printer. In some embodiments, marking device 616 comprises an ink-jet printer, such as a jetting valve printer. The ink-jet printer may be configured to perform pressurized liquid deposition to deposit an ink (e.g., a liquid ink). These devices may operate in an automated manner (e.g., in a manner such that the marking device autonomously executes a set of instructions previously provided by an operator). In some embodiments, marking device 616 comprises a markings composition, such as an ink 617, that is deposited into conduit 101 in a dehydrated state (e.g. full or partial dehydration) to allow for absorption of markings composition (e.g., ink 617) into the bulk of conduit 101.

Subsequently, the marked conduit 101 can be dried and/or annealed. Drying and/or annealing the conduit may lock the marking to the conduit, such as by physically binding and/or chemically cross-linking the markings composition (e.g., ink 617) to a portion of the conduit (e.g., to a portion of the base polymeric material 20). Marking device 616 can be configured to deposit a markings composition (e.g., ink 617) as a liquid droplet onto polymeric material 20 in the dehydrated state. Marking device 616 can be configured to apply a markings composition (e.g., ink 617) by spraying or jetting in a liquid state. Marking device 161 can be configured to deposit a markings composition (e.g., ink 617) by a pad printing, screen printing, or other ink transfer method in the liquid state. Marking device 616 can be configured to inject a markings composition (e.g., ink 617) into polymeric material 20 in a dehydrated or partially hydrated state.

Marking device 616 can further include a post-processing element configured to bind (e.g. physically, chemically, ionically) ink 617 to polymeric material 20, such as an element selected from the group consisting of: thermal treatment element; chemical treatment element; ultraviolet treatment element; radiation treatment element; and combinations of these.

When a markings composition is disposed on a surface of a conduit, it may be allowed to penetrate into the conduit to a variety of suitable depths prior to being locked thereinto. In some embodiments, the markings composition penetrate is allowed to penetrate into the conduit to a depth of greater than or equal to 10 microns, greater than or equal to 20 microns, greater than or equal to 30 microns, greater than or equal to 40 microns, greater than or equal to 50 microns, greater than or equal to 60 microns, greater than or equal to 70 microns, greater than or equal to 80 microns, greater than or equal to 100 microns, greater than or equal to 125 microns, greater than or equal to 150 microns, or greater than or equal to 175 microns. In some embodiments, the markings composition is allowed to penetrate into the conduit to a depth of less than or equal to 200 microns, less than or equal to 175 microns, less than or equal to 150 microns, less than or equal to 125 microns, less than or equal to 100 microns, less than or equal to 80 microns, less than or equal to 70 microns, less than or equal to 60 microns, less than or equal to 50 microns, less than or equal to 40 microns, or less than or equal to 30 microns. Combinations of the above-referenced ranges are also possible (e.g., greater than or equal to 10 microns and less than or equal to 200 microns, or greater than or equal to 50 microns and less than or equal to 60 microns). Other ranges are also possible.

System 10 can further comprise one or more markings composition (such as printing inks and/or compositions comprising printing inks), ink 617 shown, which can be configured to physically bind and/or chemically cross-link to polymeric material 20. A markings composition (e.g., ink 617) can comprise a dye or pigment. In some embodiments, the dye or pigment may be reactive. For instance, it may be a dye or pigment selected from the group consisting of: tetrasodium; 4-amino-5-hydroxy-3,6-bis[[4-(2-sulfonatooxyethylsulfonyl)phenyl]diazenyl]naphthalene-2,7-disulfonate (Reactive Black 5), copper; 33-[[4-(2-hydroxyethylsulfonyl)phenyl]sulfamoyl]-2,11,20,29,39,40-hexaza-37,38-diazanidanonacyclo[28.6.1.13,10.112,19.121,28.04,9.013,18.022,27.031,36]tetraconta-1,3(40),4(9),5,7,10,12(39),13(18),14,16,19,21,23,25,27,29,31(36),32,34-nonadecaene-6,15,24-trisulfonic acid (Reactive Blue 21), 2-Naphthalenesulfonicacid,7-(acetylamino)-4-hydroxy-3-[[4-[[2-(sulfooxy)ethyl]sulfonyl]phenyl]azo]-,disodium salt (9CI) (Reactive Orange 78), Reactive Yellow 15, Disodium 1-amino-9,10-dioxo-4-[(3-{[2-(sulfonatooxy)ethyl]sulfonyl}phenyl)amino]-9,10-dihydro-2-anthracene-sulfonate (Reactive Blue 19), 1-Amino-4-[3-(4,6-dichloro-triazin-2-ylamino)-4-sulfophenylamino] anthraquinone-2-sulfonic acid (Reactive Blue 4), C.I. Reactive Red 11, 4-[2-(5-carbamoyl-1-ethyl-4-methyl-2,6-dioxopyridin-3-ylidene)hydrazinyl]-6-[(4,6-dichloro-1,3,5-triazin-2-yl) amino]benzene-1,3-disulfonate (C.I. Reactive Yellow 86), Tetrasodium 6,13-dichloro-3,10-bis [[4-[(4,6-dichloro-1,3,5-triazin-2-yl) amino] sulphonatophenyl] amino] triphenodioxazinedisulphonate (C.I. Reactive Blue 163), and/or 5-(benzoylamino)-4-hydroxy-3-[[1-sulfo-6-[[2-(sulfooxy) ethyl]sulfonyl]-2-naphthalenyl]azo]-, tetrasodium salt (C.I. Reactive Red 180).

In some embodiments, the dye or pigment react with the polymeric material of the marking. In an illustrative embodiment, reaction may occur with poly(acrylic acid) with cation salt and PVA. In another illustrative embodiment, the dye or pigment may be incorporated (e.g., entrapped) within the polymeric material matrix.

In some embodiments, a markings composition comprises a non-reactive dye, pigment, and/or radiopacifier. Non-limiting examples of suitable non-reactive dyes include: phthalocyanine blue, phthalocyanine green, carbazole violet, Copper Phthalocyanine Blue with halogenated groups from 0 to 15, Pigment Blue 15, Pigment Green 7, carbon black, modified carbon black, Congo Red 17, FD&C Blue 2, (FD&C Violet 2, Carbazole Violet, FD&C Yellow 8, FD&C Yellow 10, Chromium Cobalt (See 21 CFR Part 73 Subpart D and 21CFR Part 74 Subpart D), C.I. Vat Orange 1, 2-[[2,5-Diethoxy-4-[(4-methylphenyl)thiol]phenyl]azo]-1,3,5-benzenetriol, 16,23-Dihydrodinaphtho[2,3-a:2',3'-i] naphth [2',3':6,7] indolo [2,3-c] carbazole-5,10,15,17,22,24-hexone, N,N'-(9,10-Dihydro-9,10-dioxo-1,5-anthracenediyl) bisbenzamide, 7,16-Dichloro-6,15-dihydro-5,9,14,18-anthrazinetetrone, 16,17-Dimethoxydinaphtho [1,2,3-cd:3',2',1'-lm] perylene-5,10-dione, 4-[(2,4-dimethylphenyl) azo]-2,4-dihydro-5-methyl-2-phenyl-3H-pyrazol-3-one, 6-Ethoxy-2-(6-ethoxy-3-oxobenzo[b]thien-2(3H)-ylidene) benzo[b]thiophen-3 (2H)-one, Disodium 1-amino-4-[[4-([2-bromo-1-oxoallyl)amino]-2-sulfonatophenyl]amino]-9,10-dihydro-9,10-dioxoanthracene-2-sulfonate, and combinations hereof. Non-limiting examples of suitable non-reactive pigments include: carbon black, modified carbon black, titanium dioxide, chromium-cobalt-aluminum oxide, chromium oxide greens, iron oxides, mica-based pearlescent pigments, and combination thereof.

A dye or pigment (e.g., a reactive dye or pigment, a non-reactive dye or pigment) may make up a variety of suitable amounts of the markings composition. In some embodiments, a dye makes up greater than or equal to 0.001 w/w %, greater than or equal to 0.002 w/w %, greater than or equal to 0.005 w/w %, greater than or equal to 0.0075 w/w %, greater than or equal to 0.01 w/w %, greater than or equal to 0.02 w/w %, greater than or equal to 0.05 w/w %, greater than or equal to 0.075 w/w %, greater than or equal to 0.1 w/w %, greater than or equal to 0.2 w/w %, greater than or equal to 0.5 w/w %, or greater than or equal to 0.75 w/w % of the markings composition. In some embodiments, a dye makes up less than or equal to 1 w/w %, less than or equal to 0.75 w/w %, less than or equal to 0.5 w/w %, less than or equal to 0.2 w/w %, less than or equal to 0.1 w/w %, less than or equal to 0.075 w/w %, less than or equal to 0.05 w/w %, less than or equal to 0.02 w/w %, less than or equal to 0.01 w/w %, less than or equal to 0.0075 w/w %, less than or equal to 0.005 w/w %, or less than or equal to 0.002 w/w % of the markings composition. Combinations of the above-referenced ranges are also possible (e.g., greater than or equal to 0.001 w/w % and less than or equal to 1 w/w %, great than or equal to 0.01 w/2% and less than or equal to 0.05 w/w %). Other ranges are also possible.

When a markings composition comprises two or more types of dyes and/or pigments, it should be understood that each dye or pigment may independently make up an amount of the markings composition in one or more of the ranges described above and/or all of the dyes and pigments together may make up an amount of the markings composition in one or more of the ranges described above.

A markings composition (e.g., ink 617) can comprise a dye or pigment further comprising a solvent suspension or solution including a water soluble polymer from the group consisting of: poly(vinyl alcohol); poly(acrylic acid); polyethylene glycol; or poly(vinyl pyrrolidone); poly(methacrylic sulfobetaine); poly(acrylic sulfobetaine); poly(methacrylic carboxybetaine); poly(acrylic carboxybetaine); poly (methacrylic sulfobetaine); poly(methacrylic carboxybetaine); povidone polyacrylamide; poly(N-(2-hydroxypropyl)methacrylamide); polyoxazolines; polyphosphates; polyphosphazenes; polyvinyl acetate; polypropylene glycol; poly(N-isopropylacrylamide); poly(2-hydroxymethylmethacrylate); and combinations of these.

The water soluble polymer may make up a variety of suitable amounts of the markings composition. In some embodiments, the water soluble polymer makes up greater than or equal to 10 w/w %, or greater than or equal to 12.5 w/w %. In some embodiments, the water soluble polymer makes up less than or equal to 15 w/w %, or less than or equal to 12.5 w/w %. Combinations of the above-referenced ranges are also possible (e.g., greater than or equal to 10 w/w % and less than or equal to 15 w/w %). Other ranges are also possible.

In some embodiments, the solvent suspension and/or solution further comprises water and/or a salt. Non-limiting examples of suitable salts include phosphates (e.g., MSP, DSP, TSP), borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments, ink 617 can be configured to diffuse into polymeric material 20, such as to create a colored marking within the bulk of polymeric material 20.

System 10 can further comprise one or more pressure chambers, chamber 640 shown, which can be configured to produce and/or maintain a particular pressure within the chamber (e.g. a pressure above or below room pressure). In some embodiments, pressurizing device 640 comprises a low-pressure source, such as a low-pressure oven. In some embodiments, pressurizing device 640 comprises a high-pressure source, such as a chamber with a high-pressure fan. In some embodiments, chamber 640 comprises a chamber in which both pressure and temperature can be controlled. In some embodiments, chamber 640 comprises a chamber in which humidity can also be controlled.

System 10 can further comprise one or more stretching devices, stretcher 650 shown, which can be configured to apply an axial tension to an object (e.g. conduit 101).

System 10 can further comprise one or more molding machines, molding machine 660 shown, which can be configured to form, or otherwise apply, an overmolding material (e.g. material 665 described herebelow) onto an object. (e.g. conduit 101). In some embodiments, overmolding material 665 comprises thermoplastic polyurethane (TPU) comprising a thermoplastic material selected from the group consisting of: aromatic polyether; aromatic polyester; aliphatic polyether; aliphatic polyester; polycarbonate; silicone; polypropylene; polyethylene; poly(vinyl chloride); poly(ether ether ketone); polyamide; liquid crystalline polymer; polystyrene; nylon; and combinations of these. In some embodiments, overmolding material 665 comprises silicone, such as silicone urethane copolymers. Overmolding of a first and second water soluble polymer is also possible.

In some embodiments, one or more core-pins, pin 661 shown, is configured to be slidingly inserted into the object (e.g. conduit 101) upon which molding machine 660 applies overmolding material 665.

System 10 can further comprise one or more tipping devices, tipper 670 shown, which can be configured to form a tip to conduit 101, such as a distal tip and/or a proximal tip. Tipper 670 can be configured to deliver an energy source selected from the group consisting of: heat; solvent; laser; radiofrequency; ultrasonic; and combinations of these. Tipper 670 can be configured to form a tip comprising a shape selected from the group consisting of: flat (e.g. perpendicular); beveled (e.g. oblique); blunt (e.g. radiused); tapered; flared; and combinations of these. In some embodiments, the tip is formed prior to annealing of conduit 101 (as described herebelow in reference to Method 1400 of FIG. 16). In some embodiments, the tip is formed after annealing of conduit 101 in a dehydrated state, and prior to incorporation of a humectant (as described herebelow in reference to Method 1600 of FIG. 18). In some embodiments, the tip is formed after annealing and after humectant incorporation.

System 10 can include one or more sensors, transducers, and/or other functional elements, such as functional element 99 described herebelow. Functional element 99 can comprise functional element 99a positioned on, within, and/or otherwise proximate extruder 500 (as shown), functional element 99b positioned proximate hydration device 300 (as shown), and/or another functional element 99 (e.g. positioned proximate one or more other components of system 10). Functional element 99 can be operably connected to one or more wires, optical fibers, tubes (e.g. fluid delivery, hydraulic, and/or pneumatic tubes), wave guides, and/or other conduits (not shown) that transport signals (e.g. information), energy, fluid, light, and/or sound between functional element 199 and/or another component (e.g. another component of system 10). In some embodiments, system 10 includes functional device 999 which is configured to interface with functional element 199, as described herebelow.

In some embodiments, functional elements 99 and/or 199 comprise one or more sensors, one or more transducers, and/or one or more other functional elements.

System 10 can include functional device 999 configured to operably interact with one or more of functional element 99 and/or 199.

Figure 8:
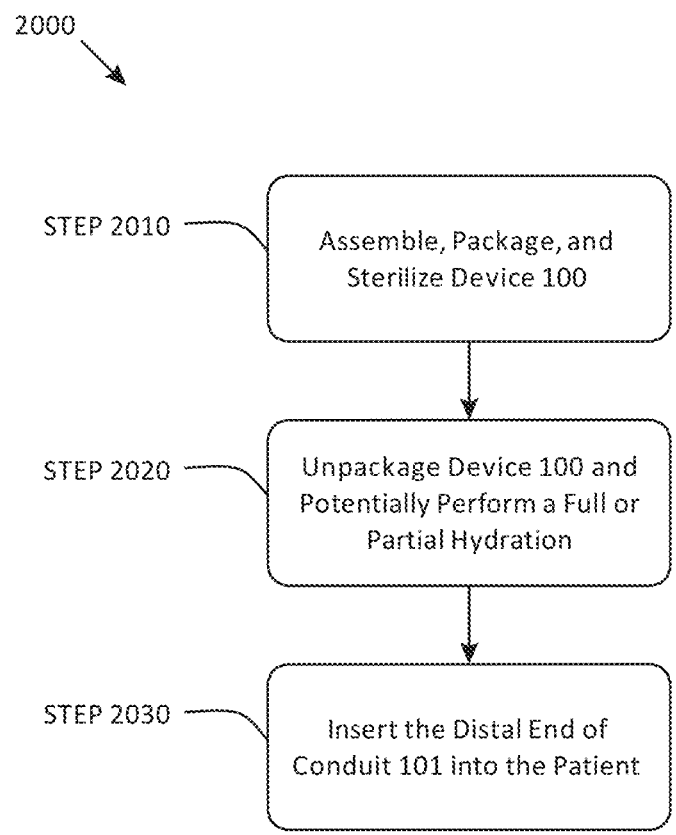
FIG. 8 illustrates a method of manufacturing, preparing, and inserting a medical device, consistent with some embodiments.

Referring now to FIG. 8, a method of inserting an article, such as a device described elsewhere herein comprising a conduit (e.g., a catheter device), into a patient is illustrated. The method 2000 of FIG. 8 will be described in reference to device 100 and other components of system 10 of FIG. 1. As described hereabove, device 100 can comprise an article that is a catheter-device, such as a nanoporous hydrophilic catheter that can be inserted into the patient's vasculature via an over-the-wire (OTW) method, with vessel dilation (e.g. vein dilation), without using a sheath introducer.

In STEP 2010 shown in FIG. 8, a device 100 is manufactured as described herein, such as when device 100 includes at least conduit 101 which has been positioned in (e.g. sealed within) packaging 180. Device 100 may be assembled, sterilized and eventually shipped to a customer for insertion into a patient (e.g. insertion of the distal portion of conduit 101 at a skin location (the "insertion location") and into the patient's vein, artery, and/or other body conduit). In some embodiments, STEP 2010 includes a full or partial hydration of at least a portion of device 100 (e.g. hydration of at least a portion of conduit 101 using hydration device 300 prior to sterilization). For example, a partial hydration procedure can be performed in which device 100 is packaged at a high equilibrium weight content (EWC). A hydration procedure can be time limited (e.g. limited to a time of less than 10 minutes), such as to achieve a desired level of hydration. In some embodiments, multiple hydration procedures are performed (e.g. with similar or dissimilar solutions 365). In some embodiments, device 100 is packaged and shipped without performing a specific hydration procedure (e.g. in a dehydrated state).

As used herein, dehydrated can be defined as having a total water content of <5 w/w %. As used herein, partially hydrated can be defined as having a water content between 5 w/w % and 90% of equilibrium water content (EWC), such as between 30-40 w/w %. As used herein, fully hydrated can be defined as having a water content within 10% of EWC, such as between 90-100% of EWC.

In STEP 2020 shown in FIG. 8, device 100, still including packaging 180, is shipped to a clinical site at which conduit 101 is to be inserted in the patient. At the location in which the insertion procedure is to be performed (the "procedure site"), and using standard sterile techniques, packaging 180 may be opened, and the remaining components of device 100 (referred to as device 100 hereinafter), are removed from the packaging 180. STEP 2020 can comprise a full or partial hydration procedure being performed on one or more portions of device 100, as detailed herebelow. The hydration procedure can be time limited, as described herein.

In STEP 2030 shown in FIG. 8, conduit 101 of device 100 is inserted into the patient, such as an insertion through the skin and into a vein or artery of the patient using the modified Seldinger technique. The distal end of conduit 101 can be advanced (e.g. over a guidewire) to one or more locations within the patient, such as to one or more locations within the patient's cardiovascular system, such as to a location within or at least proximate the patient's heart.

In some embodiments in which device 100 is shipped in a fully hydrated state, the patient insertion of STEP 2030 is performed as soon as packaging 180 is opened in STEP 2020.

In some embodiments in which device 100 is shipped in a partially hydrated state, device 100 can be further hydrated in STEP 2020, and then inserted into the patient. Alternatively, device 100 can be inserted into the patient with device 100 in a partially hydrated state (e.g. the hydration state of the shipped device 101 which is configured to be of sufficient hydration to allow for safe and easy insertion of conduit 101 into a patient), such as to provide additional column stiffness in conduit 101 while still exhibiting substantial lubricity.

In embodiments in which device 100 is shipped in a dehydrated state, device 100 can be partially or fully hydrated at the procedure site prior to insertion into the patient. As described hereabove, a partial hydration of device 100 can be performed that achieves sufficient hydration to allow safe insertion, while providing increased column stiffness (versus full hydration).

Devices 100 that are inserted into a patient in a partially hydrated state (e.g. from a partial hydration procedure performed prior to sterilization and/or at the procedure site) can be configured to continue to hydrate (e.g. continue to swell) after insertion into the patient. Post-insertion swelling (e.g. of conduit 101) can be configured to create hemostasis at the insertion location.

Hydration of one or more portions of device 100 can be performed using a hydration device 300 described herein. Hydration at the procedure site is performed using sterile technique.

Figure 9:
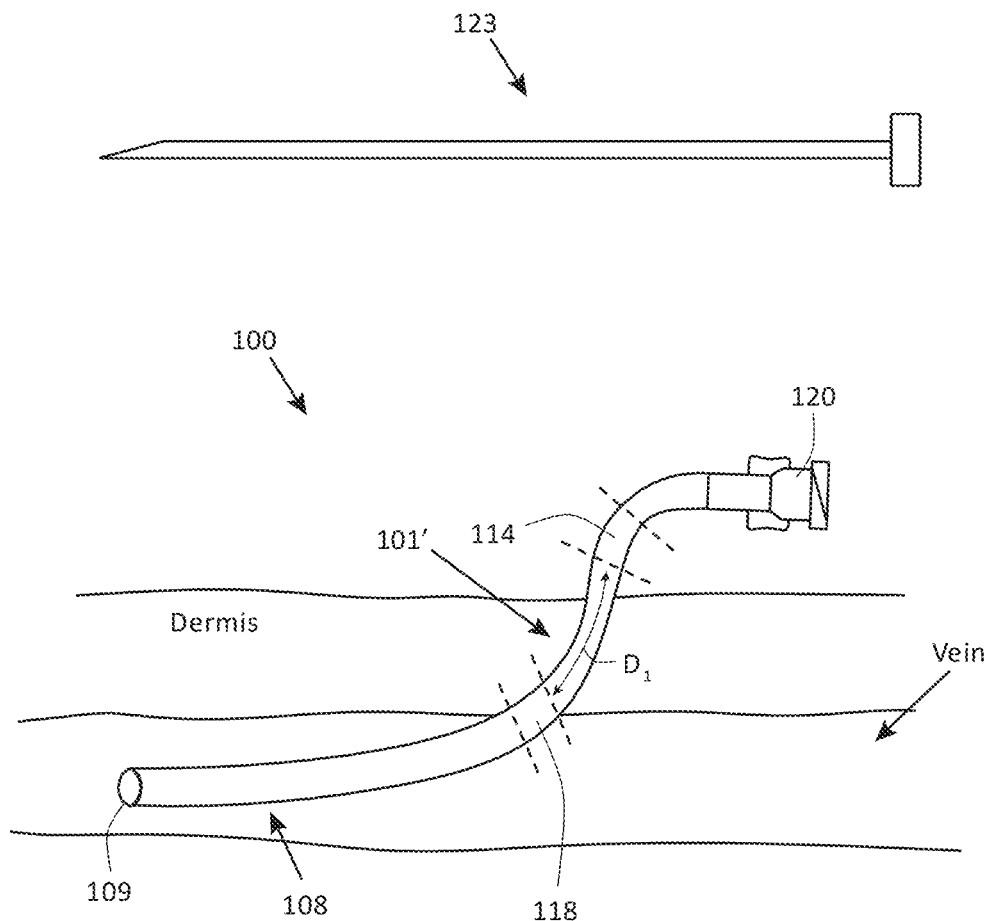
FIG. 9 illustrates a perspective view of a medical device including an S-shaped conduit, consistent with some embodiments.

Referring now to FIG. 9, a perspective view of an article that is a medical device including an S-shaped conduit is illustrated. Like the other articles and/or medical devices described herein, the article shown in FIG. 9 may be and/or comprise a catheter. Device 100 can comprise an S-shape conduit 101' configured to provide ease of implantation in a patient, achieve lower infiltration rates, and reduce the likelihood of dislodgement within the patient. Conduit 101' can comprise a first curved portion 114 and a second curved portion 118. Portions 114,118 can comprise similar or dissimilar radii of curvature. In some embodiments, first portion 114 comprises a relatively small radius (e.g. a sharp curvature) and second portion 118 comprises a relatively large radius (e.g. a broad curvature). The distance between portions 114, 118, distance Di, can comprise a distance between 1 mm and 200 mm, such as 2 mm and 20 mm, such as 10 mm. The radius of curvature for portions 114 and/or 118 can comprise a radius larger than 1 mm, such as between 2 mm and 50 mm, such as 10 mm.

In some embodiments, when device 100 is implanted in a patient, first portion 114 can be configured to remain above the dermis while second portion 118 can be configured to remain within the dermis and/or within a blood vessel (e.g. vein).

Figure 16:
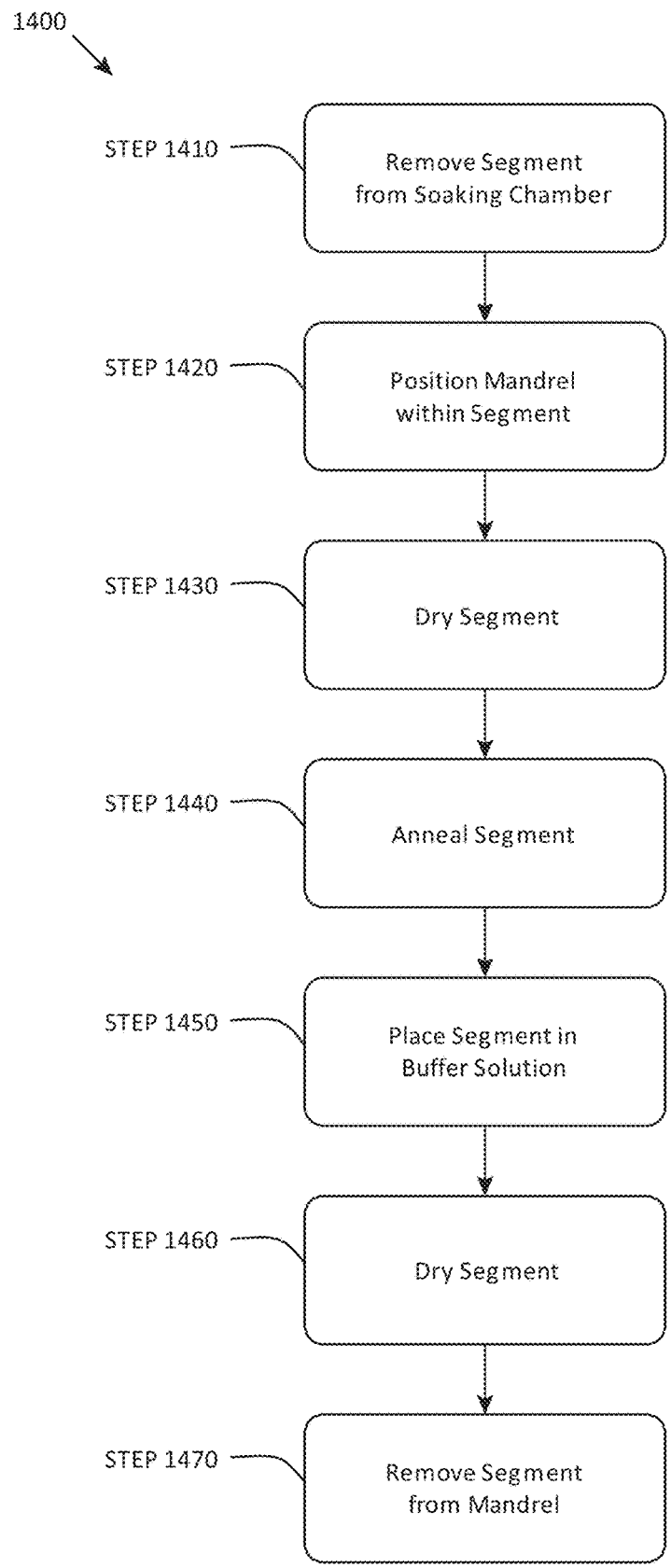
FIG. 16 illustrates a method of annealing material, consistent with some embodiments.

In some embodiments, and as described herebelow in reference to FIG. 16, a conduit 101 can be annealed or otherwise processed on an S-shaped mandrel, mandrel 614, to form an S-shaped conduit 101'. Upon removal of the S-shaped mandrel 614, conduit 101' can retain the S-shape (e.g. the material of conduit 101' can be resiliently biased or otherwise comprise shape-memory characteristics). In some embodiments, device 100 slidingly receives a linear element 123 (e.g. needle) to cause conduit 101' to be in a relatively straight geometry, such as a straight geometry that may be desired during storage, transportation, and/or patient-insertion of device 100. Upon removal of the linear element 123, device 100 (e.g. conduit 101') can assume the S-shape created by the annealing or other manufacturing process.

Figures 10A, 10B:
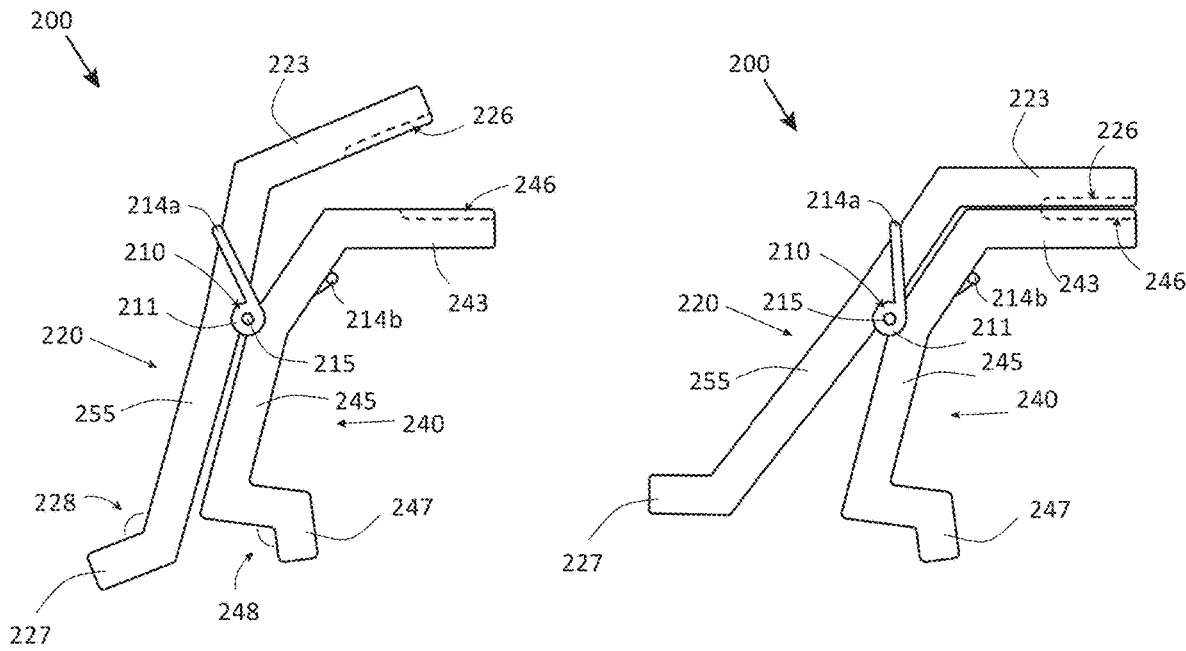
FIGS. 10A-C illustrate perspective views and an end view of a clamp for fastening or securing a conduit, consistent with some embodiments.
Figure 10C:
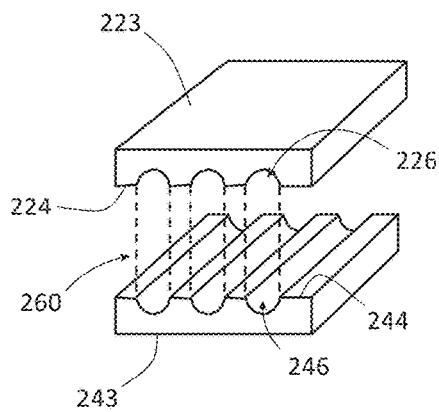

Referring now to FIGS. 10A-C, perspective views and an end view of a clamp for fastening or securing a conduit is illustrated. Clamp 200 may comprise a pair of elongate members 220,240, that are hinged, or otherwise pivoted, together via a biasing assembly 210 (e.g. similar to the construction and arrangement of a clothespin). Clamp 200 can be used to secure conduit 101 and/or another component of system 10 to a device or other separate component of system 10, such as is described herebelow in reference to FIGS. 15 and 16. In some embodiments, one or more clamps 200 are included and used to secure conduit 101 and/or another component of system 10. Biasing assembly 210 can comprise a biasing element 211 configured to rotate about an axle 215. Biasing element 211 can comprise a spring comprising two arms 214a,b, such that arm 214a engages elongate member 220 and arm 214b engages elongate member 240. Clamp 200 can be configured to transition between an open position (as shown in FIG. 10A) and a closed position (as shown in FIG. 10B). In some embodiments, biasing assembly 210 is configured to bias clamp 200 in the closed position. Clamp 200 and biasing assembly 210 can comprise a high-heat resistant material selected from the group consisting of: metals; stainless steel; nitinol; polyetheretherketone; liquid crystal polymers; polyoxymethylene; polyamide; polysulfone; polyethersulfone; polyphenylenesulfone; polyamideimide; polyetherimide; polyimide; and combinations of these.

Elongate member 220 may comprise a first portion 223 and a second portion 227, with a middle portion 225 therebetween. In some embodiments, first portion 223 and/or second portion 227 are linearly offset from middle portion 225 (e.g. first portion 223, second portion 227, and middle portion 225 are not linearly arranged). First portion 223 can comprise an inner surface 224 comprising one, two, or more longitudinal recesses 226. A recess 226 can slidingly receive at least a portion of a conduit, such as conduit 101 of device 100 (e.g. a conduit 101 comprising proximal portion 104 and distal portion 108). Second portion 227 can be constructed and arranged to comprise a cavity 228 that can receive, or otherwise engage, a bar of a rack (e.g. drying rack, oven rack, and the like).

Elongate member 240 comprises a first portion 243 and a second portion 247 with a middle portion 245 therebetween. In some embodiments, first portion 243 and/or second portion 247 are linearly offset from middle portion 245 (e.g. first portion 243, second portion 247, and middle portion 245 are not linearly arranged). First portion 243 can comprise an inner surface 244 comprising one, two, or more longitudinal recesses 246. A recess 246 can slidingly receive at least a portion of a conduit, such as conduit 101 of device 100 (e.g. conduit 101 comprising proximal portion 104 and distal portion 108). Second portion 247 can comprise a cavity 248 that can receive, or otherwise engage, a bar of a rack (e.g. drying rack, oven rack, and the like).

Inner surface 224 of first portion 223 can be configured to frictionally engage inner surface 244 of first portion 243, such that recesses 226,246 align to define one, two, or more lumens 260 (three as shown in FIG. 10C). Lumen 260 can comprise a diameter Di configured to surround and secure at least a portion of a conduit, such as conduit 101 of device 100. In some embodiments, lumen 260 surrounds and secures a portion of conduit 101 (e.g. proximal portion 104 or distal portion 108). Lumen 260 can comprise a cross-section with a geometry selected from the group consisting of: circular; elliptical; polygonal, triangular; hexagonal; pentagonal, rectangular, square, and/or trapezoidal. In some embodiments, lumen 260 comprises a cross-section equivalent to a cross-section of proximal portion 104 and/or distal portion 108 of conduit 101 of device 100.

Referring now to FIG. 11A, a perspective view of a hydration device for hydrating a conduit is illustrated, consistent with the present inventive concepts. As shown, system 10 includes device 100 and hydration device 300a. Hydration device 300a of FIG. 11A can include similar components (e.g. overtube 301, fluid reservoir 360, and/or fluid 365) and/or be of similar construction and arrangement to hydration device 300 described hereabove in reference to FIG. 1. Hydration device 300a may comprise overtube 301 which is configured to surround at least a portion of a medical device to be hydrated, such as to surround conduit 101 of device 100 as shown. Overtube 301 can comprise a length greater than or equal to the length of conduit 101 and/or device 100, such as to hydrate a majority of the length of conduit 101 and/or device 100.

Overtube 301 may comprise a proximal end 303 and a distal end 309, with lumen 306 therebetween. Proximal end 303 and lumen 306 may be sized and constructed to slidingly receive a portion of a medical device (e.g. all the portions of a medical device to be hydrated), such as to slidingly receive conduit 101 (e.g. until approximately the entire portion of device 100 to be hydrated is contained within lumen 306 of overtube 301). Proximal end 303 is further sized and constructed such that, when inserted, the proximal end or at least a proximal portion of device 100 forms a seal with proximal end 303 of overtube 301, such as to prevent or at least limit ("prevent" herein) fluid from exiting between the proximal portion of device 100 and proximal end 303. In some embodiments, device 100 includes suture wing 160, and the distal portion of suture wing 160 forms the seal with proximal end 303, such as is shown in FIG. 11A.

Once device 100 is positioned within overtube 301, an operator (e.g. a clinician, nurse, an employee of the manufacturer, and/or other qualified operator), may cause fluid 365 to fill lumen 306 of overtube 301 (e.g. after passing through lumen 106 of conduit 101). Device 100 and/or hydration device 300a are configured such that the portions of device 100 to be hydrated reach a desired hydration level (e.g. a desired water content for storage, transportation, and/or insertion into a patient).

Hydration device 300a can comprise a syringe or other fluid reservoir, fluid reservoir 360 shown, which can contain fluid 365. Fluid 365 can comprise one or more solutions or other fluids such as are described hereabove in reference to FIG. 1. Fluid reservoir 360 is configured to fluidly attach to a device inserted into overtube 301, such as when fluid reservoir 360 is fluidly attachable to connector 120 of device 100 as shown (e.g. when connector 120 comprises a luer or other connector configured to fluidly attach to a mating connector of fluid reservoir 360).

Hydration device 300a can include a flow restrictor, restrictor 340, positioned on the distal end of overtube 301, such as to limit fluid from exiting overtube 301 (e.g. to provide back pressure to restrict exiting of fluid 365 as introduced by fluid reservoir 360). In a hydration procedure, fluid 365 may be introduced into conduit 101 (via fluid reservoir 360 and connector 120) and lumen 106 may fill such that fluid 365 is in contact with the inner surface of conduit 101, after which fluid 365 may exit the distal end 109 of conduit 101. Restrictor 340 may be sized and constructed such that a portion of the fluid 365 exiting conduit 101 travels proximally, within overtube 301, toward proximal end 303 (e.g. toward suture wing 160), such that the fluid 365 contacts the outer surface of conduit 101. In some embodiments, clamp 170a is activated (e.g. clamped) after flushing fluid 365 through conduit 101 to prevent backflow.

Figure 11B:
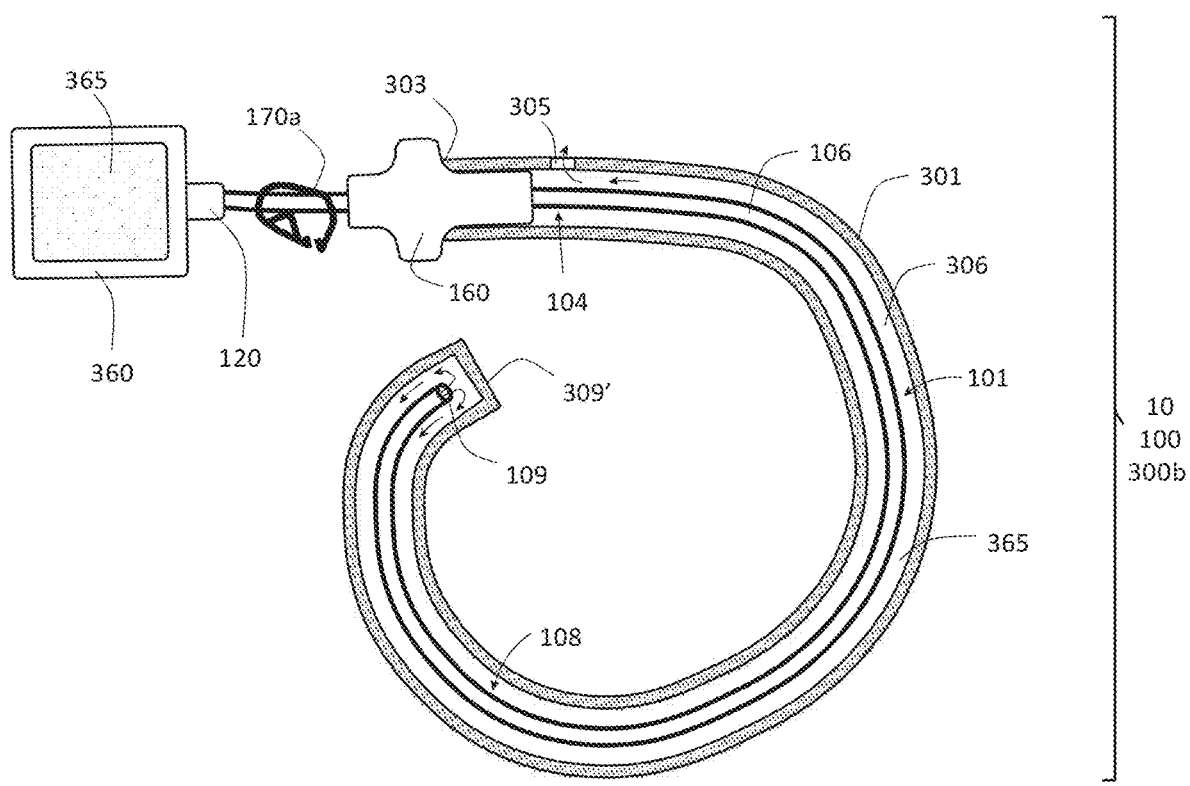
Figure 12:
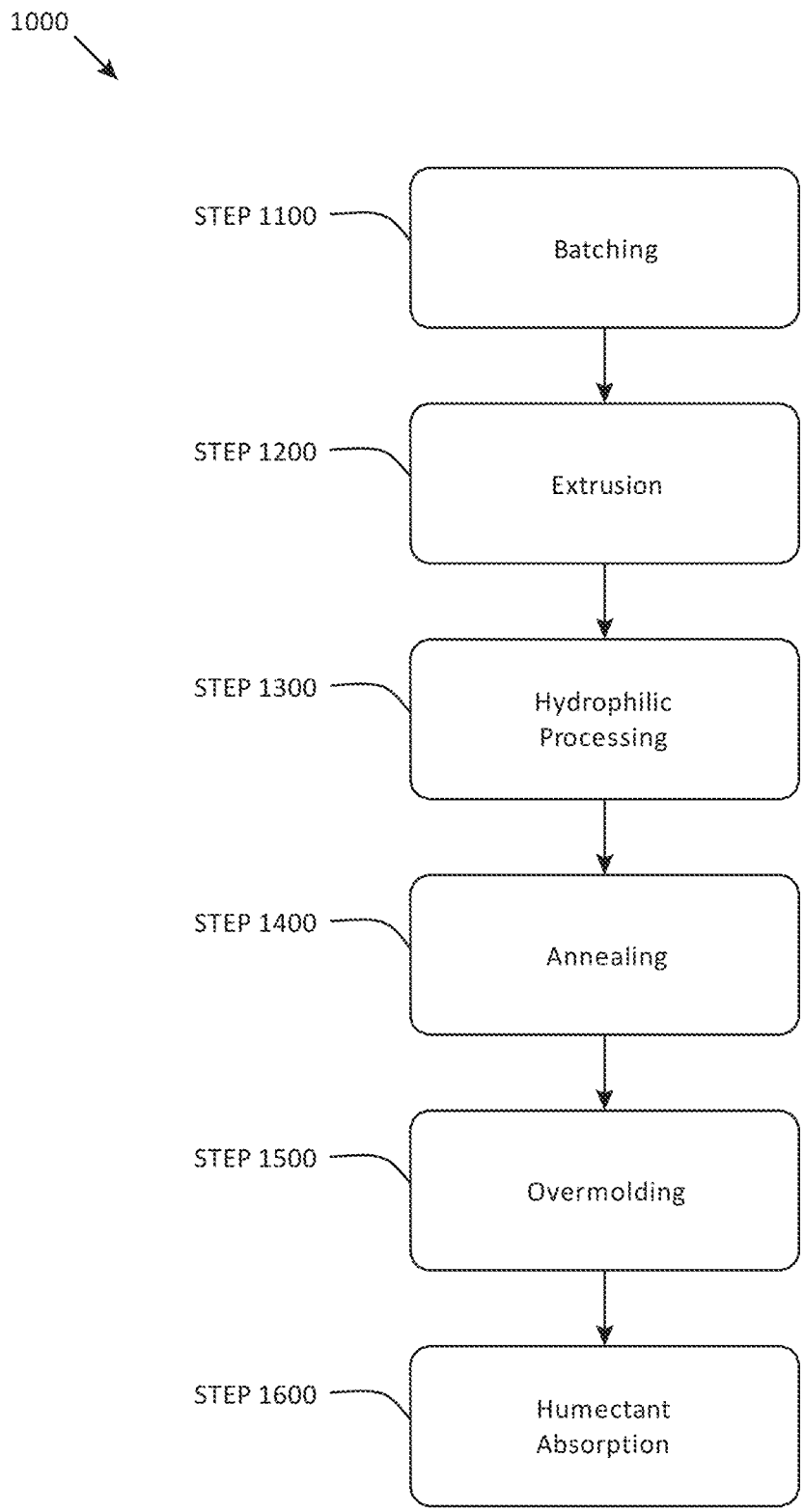
FIG. 12 illustrates a flow chart of a method for producing a conduit, consistent with some embodiments.

Referring now to FIG. 4B, a perspective view of a hydration device for hydrating a conduit and including a closed end is illustrated, consistent with the present inventive concepts. Hydration device 300b shown in FIG. 11B can include similar components and/or be of similar construction and arrangement to hydration device 300 described hereabove in reference to FIG. 1B, and/or hydration device 300a described hereabove in reference to FIG. 11A. In the embodiment of FIG. 11A, the distal end 309' of overtube 301 is closed (e.g. sealed) such as to prevent fluid from exiting closed distal end 309'. In some embodiments, a hydration procedure using hydration device 300b, fluid 365 is introduced into conduit 101 (via fluid reservoir 360 and connector 120) and lumen 106 fills such that fluid 365 is in contact with the inner surface of conduit 101, after which fluid 365 exits the distal end 109 of conduit 101. Closed distal end 309' may cause the fluid 365 exiting conduit 101 to travel proximally, within overtube 301, toward proximal end 303 (e.g. toward suture wing 160), such that the fluid 365 contacts the outer surface of conduit 101. Overtube 301 can comprise an opening, port 305 shown, positioned near proximal end 303, such that continuous flow of fluid 365 can exit port 305. In some embodiments, port 305 comprises a valve, such as a pressure-thresholded valve and/or a one-way valve. In some embodiments, clamp 170a is activated (e.g. clamped) after flushing fluid 365 through conduit 101 to prevent backflow.

Referring now to FIG. 5, a flow chart of a method for producing a conduit is illustrated, consistent with the present inventive concepts. Method 1000 shown in FIG. 5 comprises a sequence of sub-methods, methods 1100, 1200, 1300, 1400, 1500 and 1600, as described herebelow in reference to FIGS. 13-18, respectively. Method 1100 may comprise a method for batching a polymeric material. Method 1200 may comprise a method for extruding the polymeric material produced in method 1100. Method 1300 may comprise a method for hydrophilic processing of the material produced in method 1200. Method 1400 may comprise a method for annealing the material produced in method 1300. Method 1500 may comprise a method for overmolding the material produced in method 1400. Method 1600 may comprise a method for humectifying the material produced in method 1500. Methods 1100-1600, as described herebelow in references to FIGS. 13-18, may be employed to produce a single device 100, which includes a single conduit 101 from a batch of polymeric material. However, it will be understood that these methods 1100-1600 can be similarly performed to produce two, three, or more conduits 101 to be included in one, two, three, or more devices 100. The multiple conduits 101 and/or devices 100 can be produced concurrently (e.g. in a batch mode), such that the methods are modified to make use of multiple tools and/or devices (e.g. mandrels 614, filaments 608, clamps 200, etc.) of system 10 to produce multiple conduits 101 and/or devices 100 from one or more batches of polymeric material.

Figure 13:
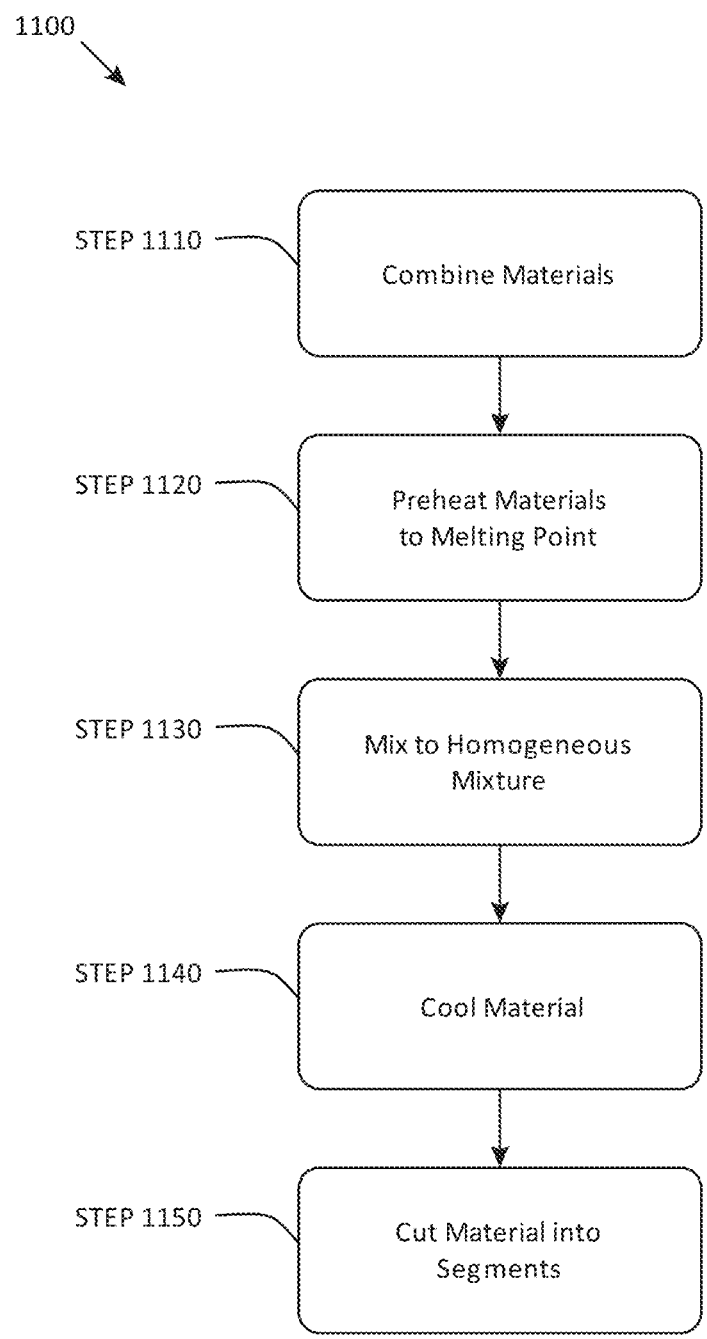
FIG. 13 illustrates a method for batching a polymeric material, consistent with some embodiments.

Referring now to FIG. 13, a method 1100 for batching a polymeric material is illustrated, consistent with the present inventive concepts.

In STEP 1110 shown in FIG. 13, a water-soluble polymer 21, a radiopaque agent 22, and/or a sodium phosphate solution 23 are combined in a container (this combination of materials referred to as "polymeric material 20" herein). Polymeric material 20 can comprise a water-soluble polymer 21 concentration of at least 10 w/w %, such as at least 20 w/w %, such as at least 30 w/w %. For example, water-soluble polymer 21 can comprise a total mass between 10 g and 150 g, such as between 25 g and 120 g, such as a mass of approximately 78 g. Polymeric material 20 can comprise a radiopaque agent 22 concentration of at least 1 w/w %, such as at least 10 w/w %, such as at least 20 w/w %. For example, radiopaque agent 22 can comprise a total mass between 0.15 g and 100 g, such as between 30 g and 60 g, such as a mass of approximately 43 g. Polymeric material 20 can comprise a sodium phosphate solution concentration of at least 20 w/w %, such as at least 40 w/w %, such as at least 50 w/w %. For example, sodium phosphate solution 23 can comprise a total mass between 100 g and 300 g, such as between 150 g and 200 g, such as a mass of approximately 179 g.

In STEP 1120 shown in FIG. 13, a cover is placed over the container and polymeric material 20 is preheated to a temperature above the polymeric material's softening point. In some embodiments, polymeric material 20 is preheated to a temperature of between 50° C. and 120° C., such as between 60° C. and 95° C., such as a temperature of approximately 65° C.

In STEP 1130 shown in FIG. 13, polymeric material 20 is mixed into a homogeneous mixture. Polymeric material 20 can be mixed using a mixing device (e.g. mixing device 602 described hereabove), such as a high speed dual asymmetric centrifuge. In some embodiments, polymeric material 20 is centrifuged at 2000 rpm for 10 minutes. During centrifugation, polymeric material 20 can be heated, such as when it is heated to a temperature between 50° C. and 120° C., such as between 80° C. and 100° C., such as a temperature of approximately 95° C. In STEP 1140 shown in FIG. 13, polymeric material 20 is cooled, such as to a temperature between 16° C. and 24° C. (e.g. cooled to room temperature).

In STEP 1150 shown in FIG. 13, polymeric material 20 is cut, or otherwise divided, into two or more segments ("segments" herein). The two or more segments can comprise similar or dissimilar sizes and/or shapes. In some embodiments, the segments comprise approximately 1 cm cubes.

Figure 14:
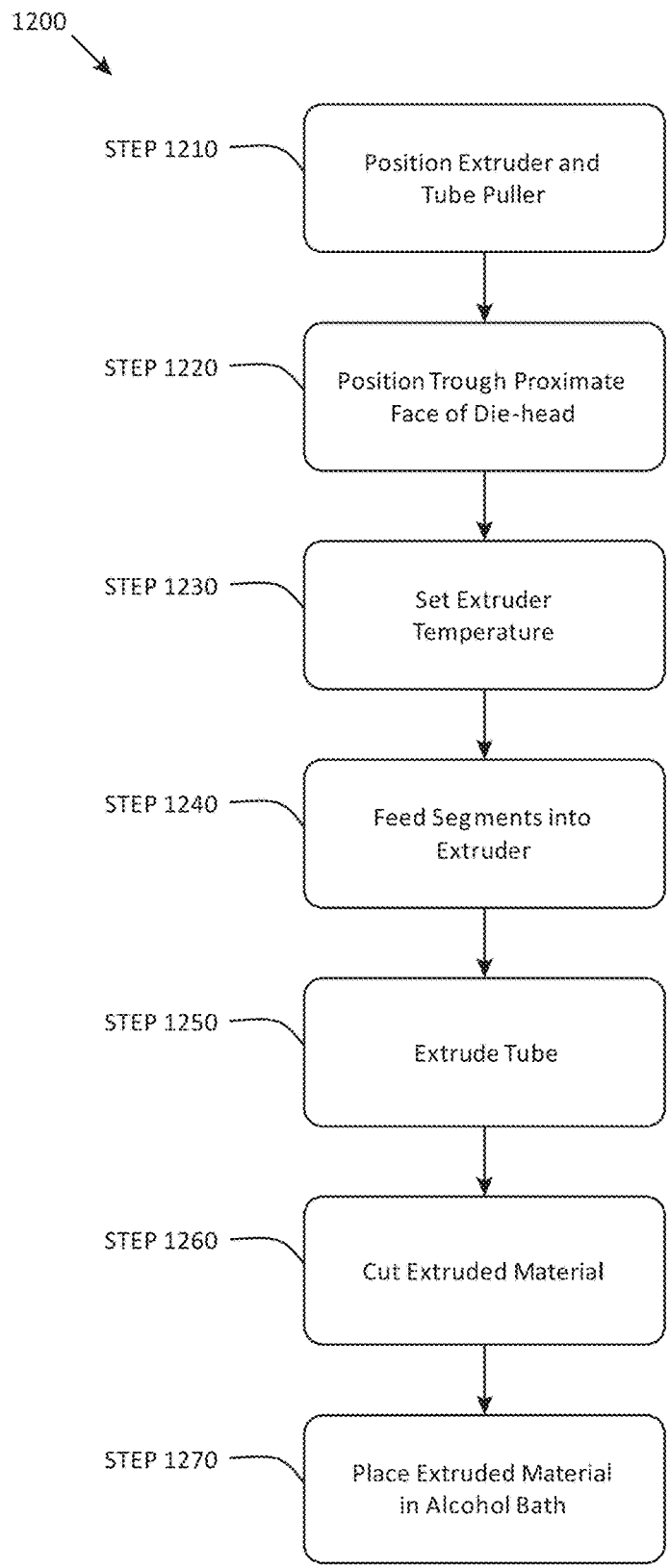
FIG. 14 illustrates a method for extruding polymeric material, consistent with the present inventive concepts.

Referring now to FIG. 14, a method 1200 for extruding polymeric material is illustrated, consistent with the present inventive concepts. Method 1200 can be configured to extrude the polymeric material produced in method 1100 described hereabove in reference to FIG. 13.

In STEP 1210 shown in FIG. 14, an extruder (e.g. extruder 500 described hereabove) is positioned perpendicular to a tube puller (e.g. tube puller 604 described hereabove).

In STEP 1220 shown in FIG. 14, a trough of fluid (e.g. trough 606 described hereabove) is positioned proximate the face of the extruder die-head 502. In some embodiments, the trough 606 is positioned approximately 15 cm away from the extruder die-head 502. The trough 606 can comprise (e.g. be at least partially filled with) an alcohol solution for incorporation into polymeric material 20. The alcohol soliton can be chilled to a temperature between −20° C. and 20° C., such as 0° C. and 15° C., such as 10° C. In some embodiments, the alcohol solution is configured to solidify polymeric material 20.

Trough 606 can further comprise a hydrophilic and/or hydrophobic polymer solution for incorporation into polymeric material 20. In some embodiments, the hydrophilic polymer solution can be configured to cause polymeric material 20 to swell, or otherwise expand, to enable polymeric material 20 to incorporate an additional polymer solution (e.g. hydrophilic, hydrophobic polymer solutions).

In some embodiments, a second trough 606 is positioned proximate the first trough 606 described hereabove. The second trough 606 can comprise a hydrophilic and/or hydrophobic polymer solution for incorporation into polymeric material 20. In some embodiments, a third trough 606 is positioned proximate the second trough 606 described hereabove. The third trough 606 can comprise an alcohol solution for incorporation into polymeric material 20. The alcohol solution can be chilled to a temperature between −20° C. and 20° C., such as 0° C. and 15° C., such as when chilled to a temperature of approximately 10° C. In some embodiments, the alcohol solution is configured to deswell polymeric material, such as to "lock in" the hydrophilic and/or hydrophobic polymer solutions.

In STEP 1230 shown in FIG. 14, one, two, or more zones of the extruder 500 are set to one, two, or more temperature profiles. For example, the extruder 500 can comprise four zones: the first zone can provide a temperature of approximately 80° C.; the second zone can provide a temperature of approximately 95° C.; the third zone can provide a temperature of approximately 95° C.; and the fourth zone can provide a temperature of approximately 40° C. In some embodiments, at least one zone comprises the die-head 502 of the extruder 500.

In STEP 1240 shown in FIG. 14, the segments from STEP 1114 are fed into the extruder 500. The extruder 500 (e.g. auger 504 of extruder 500) can be configured to operate at a rotation speed of between 1 rpm and 100 rpm, such as between 2 rpm and 40 rpm, such as a rotation speed of approximately 10 rpm. The extruder 500 (e.g. screw 506 of extruder 500) can be configured to operate at a rotation speed of between 5 rpm and 120 rpm, such as between 20 rpm and 80 rpm, such as a rotation speed of approximately 60 rpm. The extruder 500 can be configured to maintain a pressure at the tip of the screw 506 of between 20 psi and 2000 psi, such as between 100 psi and 200 psi. The extruder 500 can be configured to comprise a melt temperature at the tip of the extruder screw 506 of between 70° C. and 110° C., such as between 80° C. and 85° C.

In STEP 1250 shown in FIG. 14, polymeric material 20 is pulled through the extruder die-head 502 and trough 606, forming an extruded tube, such as a hollow extruded tube (e.g. a tube with walls surrounding one, two, or more lumens) or a solid extruded tube (e.g. a tube without a lumen). The extruded material can be pulled through the extruder die-head 502 and trough 606 at a speed between 0.25 m/min and 10 m/min, such as between 1 m/min and 4 m/min, such as a speed of approximately 2 m/min.

As used herebelow, and unless indicated otherwise, "extruded tube", "extruded material", and "extruded segment" refer to a hollow tube comprising a single lumen. It will be understood method 1200 can be modified to produce a solid extruded tube (e.g. avoiding the insertion of mandrels 614, filament 608, and the like). It will further be understood method 1200 can be modified to produce a hollow extruded tube comprising multiple lumens (e.g. with the insertion of multiple mandrels 614, filaments 608, and the like).

In some embodiments, polymeric material 20 is pulled through the extruder die-head 502 forming a hollow tube positioned around a solid filament (e.g. filament 608 described hereabove). The solid filament 608 can comprise a material selected from the group consisting of: acetal; silicone; polytetrafluoroethylene; fluorinated ethylene propylene copolymer; polyetheretherketone; polyamide; stainless steel; nitinol; silver; copper; and combinations of these.

In some embodiments, the extruded material is further pulled past an air blade (e.g. air blade 610 described hereabove) configured to remove an alcohol solution from the surface of the extruded material (e.g. an alcohol solution within the trough 606, as described herein). In some embodiments, the extruded material is further pulled through the tube puller 604, as described herein. For example, the extruded material can be pulled through the extruder die-head 502, through the trough 606, past the air blade 610, and then through the tube puller 604.

In some embodiments, various drawing and forming techniques are applied to the extruded material during the extrusion process. The drawing and forming techniques can be configured to provide an anisotropic mechanical compliance to the extruded material.

In STEP 1260 shown in FIG. 14, the extruded material is cut, or otherwise divided ("extruded segment" herein). In some embodiments, the extruded segment comprises a length of approximately 90 cm.

In STEP 1270 shown in FIG. 14, the extruded segment is placed in an alcohol bath (e.g. alcohol bath 612 described hereabove) for a duration between 10 minutes and 48 hours, such as between 3 hours and 24 hours, such as a duration of approximately 16 hours. The alcohol bath 612 can comprise a room temperature bath.

Figure 15:
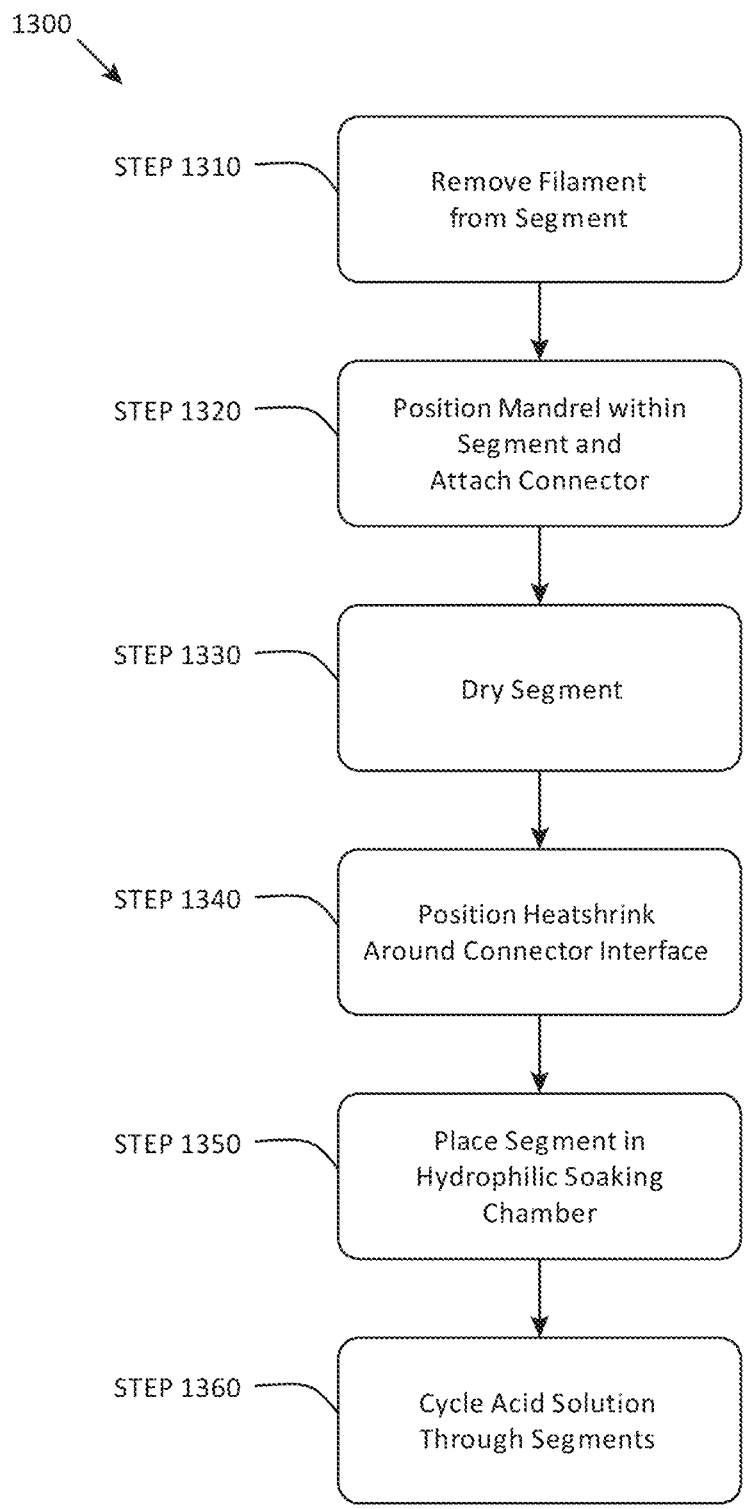
FIG. 15 illustrates a method for hydrophilic processing of material, consistent with some embodiments.

Referring now to FIG. 15, a method 1300 for hydrophilic processing of a polymeric material is illustrated, consistent with the present inventive concepts. Method 1300 can be configured to perform hydrophilic processing of the extruded material produced in method 1200 described hereabove in reference to FIG. 14.

In STEP 1310 of FIG. 15, the filament 608 (if present within the extruded segment) is removed from the extruded segment, such that the associated extruded segment comprises a lumen therethrough.

In STEP 1320 of FIG. 15, a mandrel (e.g. mandrel 614 described hereabove) is slidingly positioned within the extruded segment. A mechanical interlock connector (e.g. connector 120 described hereabove) can be inserted into one end of the extruded segment (e.g. positioned on a proximal end of conduit 101, and configured to fluidly attach to a syringe, infusion line, or other fluid delivery device or conduit).

In STEP 1330 of FIG. 15, the extruded segment is dried in a convection oven (e.g. oven 620 described hereabove). In some embodiments, the extruded segment is dried in a convection oven 620 for a duration between 1 hour and 24 hours and at a temperature between 20° C. and 100° C., such as for 3 hours at 55° C.

In some embodiments, a first clamp 200 secures the first end of the extruded segment and a second clamp 200 secures the second end of the extruded segment, as described hereabove in reference to FIGS. 10A-C. First clamp 200 (e.g. cavities 228, 248) can engage inner bars of an upper drying rack (e.g. top rack 622a described hereabove) and second clamp 200 (cavities 228, 248) can engage inner bars of a lower drying rack (e.g. bottom rack 622b described hereabove), such that the extruded segment extends from the upper drying rack 622a to the lower drying rack 622b. In this embodiment, clamps 200 are used in conjunction to prevent a twisting, or other axial deformation, of the extruded segment during this step (e.g. clamps 200 are used in conjunction to straighten the extruded segment during this step).

In STEP 1340 of FIG. 15, an external heat shrink (e.g. band 122 described hereabove) is positioned over, or otherwise around, the interface between the mechanical interlock connector 120 and the extruded segment. In some embodiments, and prior to proceeding to STEP 1350, mandrel 614 is slidingly removed from the extruded segment.

In some embodiments, one, two, or more markings (e.g. markings 112 described hereabove) are made along the length of the extruded segment. The markings 112 can be configured to expand and contract as the extruded segment expands and contracts (e.g. swells and deswells). The markings 112 can be positioned relative to a single point of the extruded segment. For example, a solid-state laser (e.g. laser 616 described hereabove) can be configured to apply one, two, or more dashes, dots, or other markings 112 along the length of the extruded segment (e.g. markings 112 positioned at fixed intervals such as to provide a "ruler" to aid in depth of insertion of the device into the patient).

In STEP 1350 of FIG. 15, the extruded segment is placed in a hydrophilic soaking chamber (e.g. soaking chamber 618 described hereabove). The hydrophilic soaking chamber can be configured to promote the incorporation of a hydrophilic polymer into at least a portion of the extruded segment. In some embodiments, the hydrophilic soaking chamber 618 comprises a poly(acrylic acid) solution (e.g. solution 631 described hereabove), such that the acrylic acid solution is incorporated into the extruded segment. For example, the hydrophilic soaking chamber 618 can comprise a 1 w/w % solution of poly(acrylic acid) in 5× phosphate buffered saline. In some embodiments, and prior to proceeding to STEP 1360, the extruded segment slidingly receives mandrel 614.

In STEP 1360 of FIG. 15, the poly(acrylic acid) solution is cycled through, and around, the extruded segment. In some embodiments, the poly(acrylic acid) solution is cycled at a temperature of approximately 37° C. for a duration of 16-20 hours.

In some embodiments, one, two, or more agents are incorporated into the extruded segment. The agents can be configured to provide a dual, or plural, functionality to the extruded segment. The agents can be configured to at least one of act, function, and interact with patient tissue, such as to promote at least one of adherence, ingrowth and clotting of the tissue. In some embodiments, the agents are configured to bind at least one of collagen and albumin. In some embodiments, the agents are configured as precursors configured to bind specific proteins. Additionally or alternatively, the agents can be configured to reduce thrombogenicity along at least a portion of the extruded segment. Each of the agents can be incorporated along a specific length, portion, and/or area of the extruded segment.

A first method for incorporating the agents can comprise processing the hydrophilic polymer as described hereabove in reference to STEPs 1350 and 1360 and subsequently stripping the first hydrophilic polymer from at least a portion of the extruded segment. In some embodiments, STEPs 1350 and 1360 are repeated with an agent, such that the agent is incorporated into the portions from which the first hydrophilic polymer was stripped. Additional agents can be similarly incorporated (e.g. the first agent is stripped from at least a portion of the extruded segment). In other embodiments, the agent is particularly applied to at least a portion of the extruded segment from which the hydrophilic polymer was stripped. Additional agents can be similarly incorporated (e.g. particularly applied to at least a portion of the extruded segment that does not comprise the hydrophilic polymer and/or first agent).

A second method for incorporating the agents can comprise processing the hydrophilic polymer as described hereabove in reference to STEPs 1350 and 1360 with one or more portions of the extruded segments excluded or otherwise shielded from the processing, such that the hydrophilic polymer is not incorporated into the excluded portions. In some embodiments, STEPs 1350 and 1360 are repeated with an agent, such that the agent is incorporated into the excluded portions. Additional agents can be similarly incorporated (e.g. one or more portions of the extruded segments are excluded or otherwise shielded from the first agent). In other embodiments, the agent is particularly applied to the excluded portions. Additional agents can be similarly incorporated (e.g. particularly applied to excluded portions that do not comprise the hydrophilic polymer and/or first agent).

As non-limiting example, the first hydrophilic polymer can be incorporated along at least a portion of the interior (e.g. lumen) of the exterior segment and can be configured to reduce thrombogenicity. A second hydrophilic polymer can be incorporated along at least a portion of the exterior of the extruded segment and can be configured to promote the adherence and/or ingrowth of tissue. In this example, the interior of the extruded segment is configured as non-thrombogenic and the exterior is configured to interact with surrounding tissue.

Referring now to FIG. 16, a method 1400 for annealing material is illustrated, consistent with the present inventive concepts. Method 1400 can be configured to anneal the material produced in method 1300 as described hereabove in reference to FIG. 15.

In STEP 1410 of FIG. 16, the extruded segment is removed from the hydrophilic soaking chamber 618.

In some embodiments, one, two, or more plasticizers (e.g. plasticizers 29 described hereabove) are incorporated into the extruded segment. The plasticizers 29 can be configured to prevent, or otherwise reduce, cracking and/or fracturing of the extruded segment.

In STEP 1420 of FIG. 16, a mandrel (e.g. mandrel 614 described hereabove) is slidingly positioned within the extruded segment. In some embodiments, the mandrel comprises a non-stick surface, such as a PTFE coating. In some embodiments, the mandrel comprises a nickel-titanium alloy. The mandrel can comprise any specified geometry to yield a conformal shape-memory geometry to the extruded segments. In some embodiments, the mandrel comprises a non-cylindrical shape and/or a non-circular cross-section, such that the associated extruded segment's lumen is configured to assume the mandrel's non-cylindrical and/or non-circular shape. In some embodiments, the mandrel comprises a diameter that varies along the length of the mandrel. In some embodiments, the mandrel comprises a non-linear shape (e.g. curved, bent, or other compound shape), such that the associated extruded segments are configured to assume the mandrel's non-linear shape. For example, the mandrel can comprise a relative "S" shape as described hereabove in reference to FIG. 9. In some embodiments, the mandrel comprises an over-sized mandrel (e.g. a mandrel with an outer diameter greater than the lumen diameter of the segment) configured to stretch, or otherwise expand the diameter of, the associated extruded segment's walls. This stretching of the extruded segment's walls can be configured to provide an anisotropic mechanical compliance to the extruded segment, and/or other effect as described herebelow in reference to applying a pressure differential across the walls of the extruded segment.

Alternatively or additionally, a pressure differential can be applied across the wall (a pressure difference between the inner surface of the wall and the outer surface of the wall) of the extruded segment (e.g. an elevated pressure applied within the lumen, and/or a reduced pressure applied outside the extruded segment), such as to cause the wall of the extruded segment to radially expand (e.g. similar to the expansion caused by the insertion of the mandrel 614 described hereabove, such that insertion of a mandrel is not required to cause the desired effect). The pressure differential can be configured to allow an increase in crystallinity that prominently forms during a compression of polymeric material 20 as bound water is removed. Increased crystallinity can correlate with an increase in strength and/or decrease in equilibrium water content. The pressure differential can be applied via a pressurizing device (e.g. pressurizing device 640 described hereabove). In some embodiments, a high pressure is applied to the extruded segment's lumen and a low pressure is applied to the extruded segment's exterior surface. Alternatively or additionally, the pressure differential can be increased by locking one, two, or more fluids within the extruded segment's lumen. Each end of the extruded segment can be sealed, or otherwise closed, to lock the fluid within the lumen. The locking fluid can be configured to expand in response to an increase in temperature. The locking fluid can comprise a fluid selected from the group consisting of: dimethylacetamide; dimethyl sulfoxide; silicone oil; mineral oil; air; nitrogen; argon; and combinations of these. The locking fluid can comprise a non-solvent comprising a phase transition temperature of less than 0° C. The locking fluid can comprise a non-solvent comprising a phase transition temperature greater of greater than 180° C.

In STEP 1430 of FIG. 16, the extruded segment is dried and/or annealed. The drying and/or annealing may be performed thermally, such as in a convection oven 620. The drying time may generally be selected as desired. For instance, it may be 30 minutes or greater. In some embodiments, the extruded segment is dried in a convection oven 620 for a duration between 1 hour and 24 hours at temperatures between 30° C. and 100° C., such as for 3 hours at 55° C. It is also possible for annealing to be formed at higher temperatures (e.g., in excess of 100° C. The annealing may be performed at atmospheric pressure.

In some embodiments, a first clamp 200 secures the first end of the extruded segment and a second clamp 200 secures the second end of the extruded segment, as described hereabove in reference to FIGS. 10A-C. First clamp 200 (e.g. cavities 228, 248) can engage inner bars of an upper drying rack (e.g. top rack 622*a* described hereabove) and second clamp 200 (cavities 228, 248) can engage inner bars of a lower drying rack (e.g. bottom rack 622*b* described hereabove), such that the extruded segment extends from the upper drying rack 622*a* to the lower drying rack 622*b*. In this embodiment, clamps 200 are used in conjunction to prevent a twisting, or other axial deformation, of the extruded segment during this step (e.g. clamps 200 are used in conjunction to straighten the extruded segment during this step).

In some embodiments, one, two, or more markings (e.g. markings 112 described hereabove) are made along the length of the extruded segment. The markings 112 can be configured to expand and contract as the extruded segment expands and contracts (e.g. swells and deswells). For example, one, two, or more droplets of a dye solution (e.g. solution 634 described hereabove) can be deposited along the length of the extruded segment. The dye solution can be configured to penetrate the extruded segment to a depth between 10 μm and 200 μm, such as between 50 μm and 60 μm. The dye solution can comprise between 0.01 w/w % to 5.0 w/w % Reactive Black 5 in USP water, such as 0.2 w/w % Reactive Black 5 in USP water and can be deposited via a blunt-tipped needle, such as a 24-gauge needle. In some embodiments, the dye solution is configured to dry at ambient conditions for at least 10 minutes, such as approximately 2 hours prior to proceeding to STEP 1440. In some embodiments the dye solution can comprise between 0.01 w/w % to 5.0 w/w % Reactive Black 5 in the poly(acrylic acid) solution from Step 1350 or 1360.

In STEP 1440 of FIG. 16, the extruded segment is annealed in a convection oven (e.g. oven 620 described hereabove). In some embodiments, the extruded segment is annealed in a convection oven 620 for between 30 minutes and 24 hours and at a temperature between 120° C. and 200° C., such as approximately 90 minutes at a temperature of approximately 150° C. In some embodiments, a first clamp 200 secures the first end of the extruded segment and a second clamp 200 secures the second end of the extruded segment, as described hereabove in reference to FIGS. 10A-C. First clamp 200 (e.g. cavities 228, 248) can engage inner bars of an upper drying rack (e.g. top rack 622*a* described hereabove) and second clamp 200 (cavities 228, 248) can engage inner bars of a lower drying rack (e.g. bottom rack 622*b* described hereabove), such that the extruded segment extends from the upper drying rack 622*a* to the lower drying rack 622*b*. In this embodiment, clamps 200 are used in conjunction to prevent a twisting, or other axial deformation, of the extruded segment during this step (e.g. clamps 200 are used to tension the extruded segment during this step).

In some embodiments, the extruded segment is annealed using selective or gradient temperatures. The gradient temperatures can be configured to provide differential mechanical properties (e.g. compliance) along the length of the extruded segment. In some embodiments, the gradient can be generated by convective heating elements directed at a portion of the extruded segment. In some embodiments, the extruded segment can be placed in oven 620 such that a portion of the extruded segment falls outside of oven 620. In some embodiments, the extruded segment is annealed using selective or gradient solvent exposure and/or extraction of solvent components (e.g. salts, additives, secondary hydrophilic polymer, and the like). The selective or gradient exposure and/or extraction can be configured to provide differential mechanical properties (e.g. compliance) along the length of the extruded segment.

In some embodiments, the extruded segment is subsequently exposed to a hydrophilic polymer solution (e.g. solution 633 described hereabove). The hydrophilic polymer solution can comprise an aqueous solution selected from the group consisting of: polyvinyl alcohol; polyvinylpyrrolidone; polyethylene glycol; polyacrylic acid; polyacrylamide; hydroxypropyl methacrylamide; polyoxazolines; polyphosphates; polyphosphazenes; poly(vinyl acetate); polypropylene glycol; poly(n-isopropylacrylamide); polysaccharides; sulfonated hydrophilic polymers, such as sulfonated polyphenylene oxide, sulfonated tetrafluoroethylene, sulfobetaine methacrylate; and combinations of these. In some embodiments, the aqueous solution further comprises iodine. The hydrophilic polymer solution can comprise a temperature of at least 45° C., such as a temperature of approximately 70° C. In some embodiments, the extruded segment is dried in a convection oven (e.g. oven 620 described hereabove) for a second time. The extruded segment can be dried in a convection oven for approximately 3 hours at a temperature of approximately 55° C. In some embodiments, the extruded segment is annealed in a convection oven 620 for a second time. This second annealing can be configured to increase the overall strength of the extruded segment (versus a single annealing). The extruded segment can be annealed a second time in a convection oven 620 for approximately 90 minutes at a temperature of at least 120° C. The second annealing temperature can be at a temperature of at least 30° C. greater than the temperature of the first annealing performed in STEP 1440.

In some embodiments, an axial stretching device (e.g. stretching device 650 described hereabove) is configured to apply axial tension on the extruded segment during the annealing. Applying axial tension to an extruded segment can be configured to provide an anisotropic mechanical compliance to the extruded segment.

In STEP 1450 of FIG. 16, the extruded segment is placed in a buffer solution (e.g. solution 632 described hereabove). The buffer solution can comprise a solution at room temperature. In some embodiments, the extruded segment remains in the buffer solution for approximately 60 minutes. The buffer solution can comprise a solution selected from the group consisting of: PBS; normal saline; monosodium phosphate; disodium phosphate; trisodium phosphate; lactated ringer's injection; and combinations of these.

In STEP 1460 of FIG. 16, the extruded segment is dried in a convection oven (e.g. oven 620 described hereabove). In some embodiments, the extruded segment is dried in a convection oven 620 for approximately 3 hours at approximately 55° C.

In some embodiments, a first clamp 200 secures the first end of the extruded segment and a second clamp 200 secures the second end of the extruded segment, as described hereabove in reference to FIGS. 10A-C. First clamp 200 (e.g. cavities 228, 248) can engage inner bars of an upper drying rack (e.g. top rack 622*a* described hereabove) and second clamp 200 (cavities 228, 248) can engage inner bars of a lower drying rack (e.g. bottom rack 622*b* described hereabove), such that the extruded segment extends from the upper drying rack 622*a* to the lower drying rack 622*b*. In this embodiment, clamps 200 are used in conjunction to prevent a twisting, or other axial deformation, of the extruded segment during this step (e.g. clamps 200 are used in conjunction to straighten the extruded segment during this step).

In STEP 1470 of FIG. 16, the extruded segment is removed from the mandrel 614.

Figure 17:
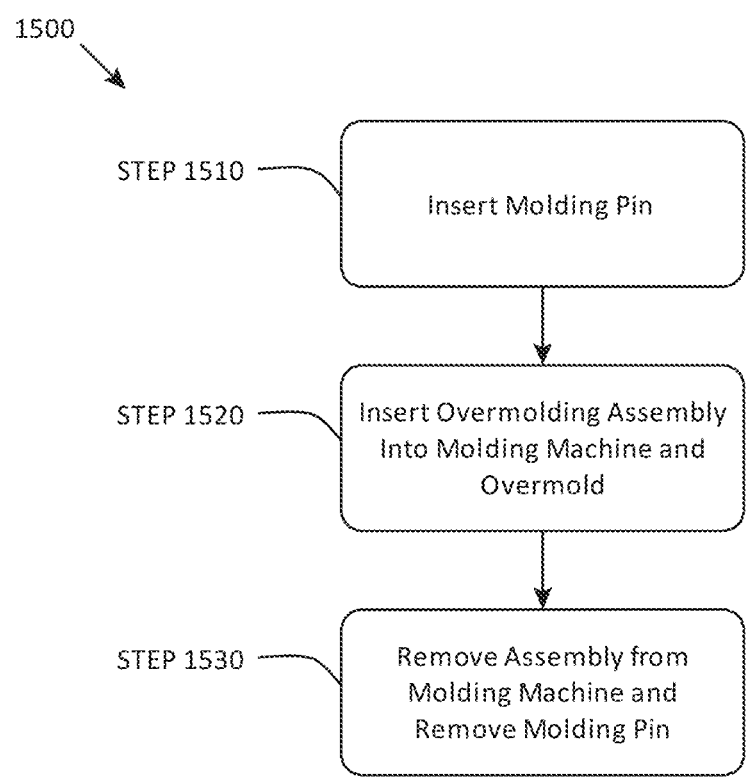
FIG. 17 illustrates a method of overmolding material, consistent with the present inventive concepts.

Referring now to FIG. 17, a method 1500 for overmolding material is illustrated, consistent with the present inventive concepts. Method 1500 can be configured to overmold the material produced in method 1400 described hereabove in reference to FIG. 16.

In STEP 1510 of FIG. 17, a molding core-pin (e.g. pin 661 described hereabove) is slidingly positioned within the extruded segment (combined pin 661 and extruded segment referred to as "overmolding assembly" herein). In some embodiments, the molding core-pin 661 comprises an extension tube and luer connector.

In STEP 1520 of FIG. 17, the overmolding assembly is placed into a molding machine (e.g. molding machine 660 described hereabove). In some embodiments, the molding machine 660 comprises a reciprocating screw injecting molding machine. The molding machine 660 can be configured to apply overmolding material 665 onto the overmolding assembly.

In STEP 1530 of FIG. 17, the overmolding assembly is removed from the molding machine 660. Additionally, the core-pin 661 is removed from the extruded segment.

In some embodiments, one, two, or more markings (e.g. markings 112 described hereabove) are made along the length of the extruded segment. The markings 112 can be configured to expand and contract as the extruded segment expands and contracts (e.g. swell and deswell). The markings 112 can be positioned relative to a single point of the extruded segment. For example, a solid-state laser (e.g. laser 616 described hereabove) can be configured to apply one, two, or more dashes, dots, and/or other markings 112 along the length of the extruded segment (e.g. markings 112 positioned at fixed intervals such as to provide a "ruler" to aid in depth of insertion of the device into the patient).

FIGS. 23A-23B show photographs of exemplary marked catheters, according to one set of embodiments.

Figure 18:
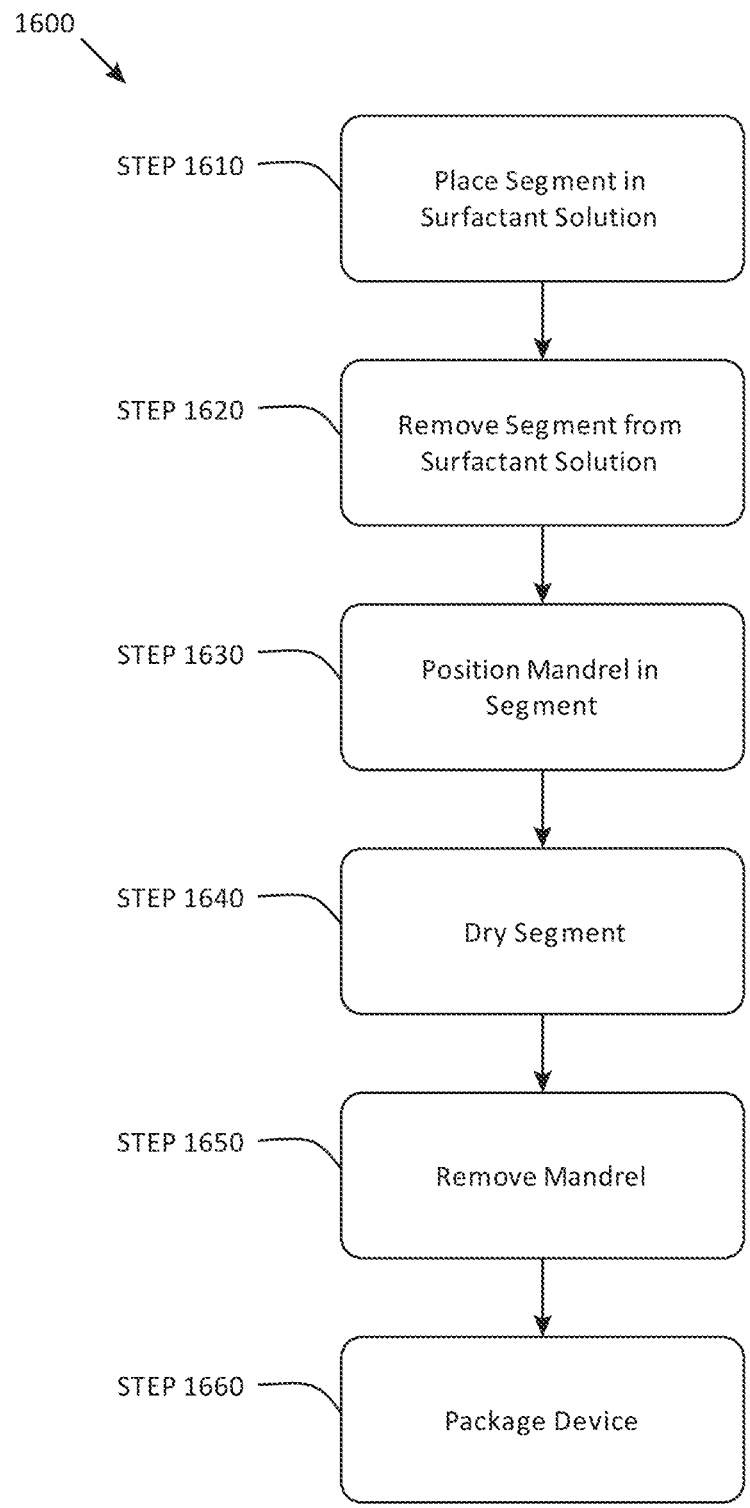
FIG. 18 illustrates a method of humectifying material, consistent with some embodiments.

Referring now to FIG. 18, a method 1600 for humectifying material is illustrated, consistent with the present inventive concepts. Method 1600 can be configured to humectify the material produced in method 1500 described hereabove in reference to FIG. 17.

In STEP 1610 of FIG. 18, the extruded segment is placed into a surfactant solution (e.g. surfactant solution 635 described hereabove). In some embodiments, the extruded segment remains in the surfactant solution for approximately 3 hours. Surfactant solution 635 can comprise a solution comprising 10 w/w % poloxamer 407 in 1×PBS or a solution comprising 30 w/w % glycerol in 1×PBS. In some embodiments, surfactant solution 635 is maintained at a temperature between 20° C. and 70° C., such as between 37° C. and 55° C., such as approximately 45° C.

In STEP 1620 of FIG. 18, the extruded segment is removed from the surfactant solution. In STEP 1630 of FIG. 18, a mandrel (e.g. mandrel 614 described hereabove) is slidingly positioned within the extruded segment. In some embodiments, the mandrel 614 comprises a non-stick surface, such as a PTFE coating.

In STEP 1640 of FIG. 18, the extruded segment is dried in a convection oven (e.g. oven 620 described hereabove). In some embodiments, the extruded segment is dried in a convection oven 620 for approximately 3 hours at approximately 30° C.

In some embodiments, a first clamp 200 secures the first end of the extruded segment and a second clamp 200 secures the second end of the extruded segment, as described hereabove in reference to FIGS. 10A-C. First clamp 200 (e.g. cavities 228, 248) can engage inner bars of an upper drying rack (e.g. top rack 622a described hereabove) and second clamp 200 (cavities 228, 248) can engage inner bars of a lower drying rack (e.g. bottom rack 622b described hereabove), such that the extruded segment extends from the upper drying rack 622a to the lower drying rack 622b. In this embodiment, clamps 200 are used in conjunction to prevent a twisting, or other axial deformation, of the extruded segment during this step (e.g. clamps 200 are used in conjunction to straighten the extruded segment during this step).

In STEP 1650 of FIG. 18, the extruded segment is removed from the mandrel 614. In some embodiments, the extruded segment is lyophilized. The lyophilization can be configured to prevent, or otherwise reduce, a swelling of the extruded segment during subsequent re-hydration (e.g. when a fluid contacts the extruded segment). In some embodiments, the extruded segment from STEP 1650 is frozen at a temperature below 0° C., then a vacuum is drawn below 5 torr, such as below 500 mtorr, and the extruded segment is heated to a temperature above 0° C., such as approximately 25° C., to allow for sublimation of the ice from the extruded segment.

In STEP 1660 of FIG. 18, the extruded segment (e.g. conduits 101) is placed into protective sleeves for packaging. The extruded segment can be sterilized prior to placement into the protective sleeves. In some embodiments, the extruded segment is sterilized by ethylene oxide exposure, peroxide exposure, peracetic acid exposure, gamma radiation, x-ray radiation, or electron beam radiation. Alternatively or additionally, the extruded segment can be hydrated prior to placement into the protective sleeves. In some embodiments, the extruded segment is hydrated via hydration device 300, as described hereabove in reference to FIGS. 1, 4A and/or 4B.

Although conduit 101 has been primarily described in the context of a device 100 comprising a catheter device (e.g. an elongate tube with a lumen), it is further appreciated that conduit 101, using the manufacturing, hydration, and other processes described herein, can comprise various tubular (e.g. hollow or solid) and non-tubular shapes.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In some embodiments, the compositions and articles (e.g., article 1710 of FIG. 19, article 1712 of FIG. 20) described herein comprise a polymeric material comprising a first water soluble polymer having a plurality of pores and a second water soluble polymer, same or different than the first water soluble polymer, positioned within at least a portion of the plurality of pores. Without wishing to be bound by theory, in some embodiments, the presence of a second water soluble polymer positioned within at least a portion of the plurality of the pores of the first water soluble may decrease the thrombogenicity and/or increase the lubriciousness of the article (e.g., article 1710 of FIG. 19, article 1712 of FIG. 20) as compared to articles (e.g., article 1710 of FIG. 19, article 1712 of FIG. 20) without the second water soluble polymer positioned within the pores (all other factors being equal). In an exemplary set of embodiments, the first water soluble polymer is polyvinyl alcohol. In another exemplary set of embodiments, the second water soluble polymer is polyacrylic acid. Other water soluble polymers are also possible, as described herein.

In some embodiments, the articles and compositions described herein are administered to a subject. In some embodiments, the article may be administered orally, rectally, vaginally, nasally, intravenously, subcutaneously, or urethrally. In some cases, the article may be administered into a cavity (e.g., in a venous system), epidural space, and/or abscess of a subject.

Figure 19:
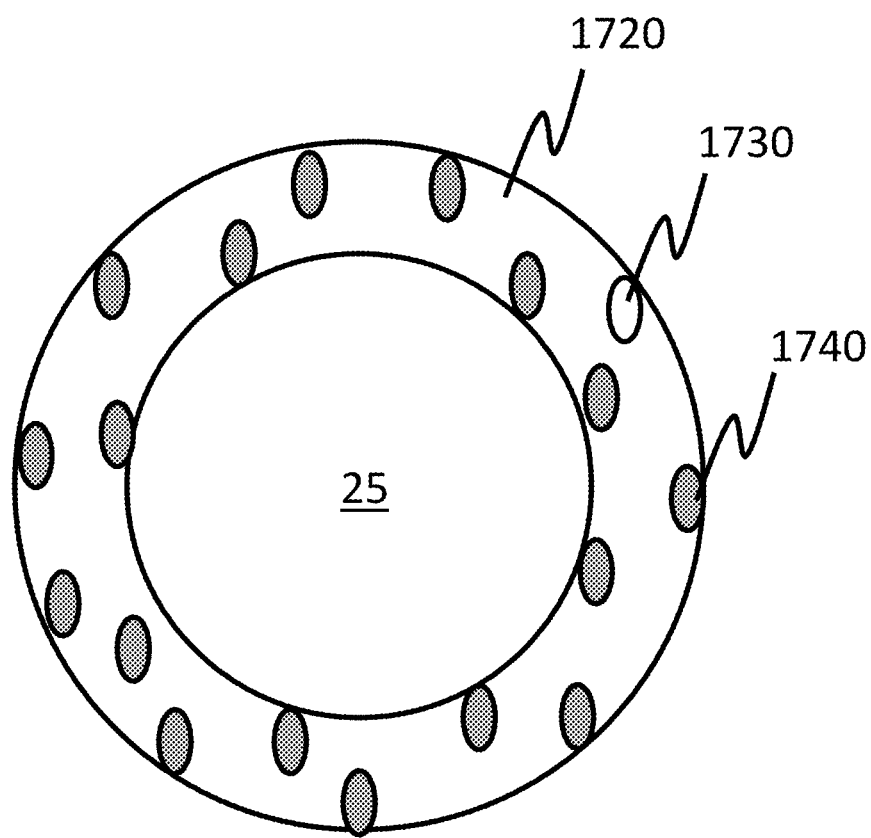
FIGS. 19-20 illustrate articles comprising pluralities of pores, consistent with some embodiments.

As described herein, in some embodiments, the compositions and articles described herein comprise a polymeric material comprising a first water soluble polymer having a plurality of pores. For example, as illustrated in FIG. 19 article 1710 comprises polymeric material comprising a first water soluble polymer 1720 and having a plurality of pores 1730. In some embodiments, second water soluble polymer 40 is positioned within at least a portion (e.g., at least 10%, at least 20%, at least 30%, at least 40%, at least 50%, at least 60%, at least 70%, at least 80%, at least 90%, at least 95%, at least 98%, at least 99%, at least 99.99%) of the plurality of pores. In some embodiments, second water soluble polymer 1740 is positioned within less than or equal to 100%, less than or equal to 90%, less than or equal to 80%, less than or equal to 70%, less than or equal to 60%, less than or equal to 50%, less than or equal to 40%, less than or equal to 30%, less than or equal to 20%, or less than or equal to 10% of the plurality of pores 30. Combinations of the above-referenced ranges are also possible.

Figure 20:
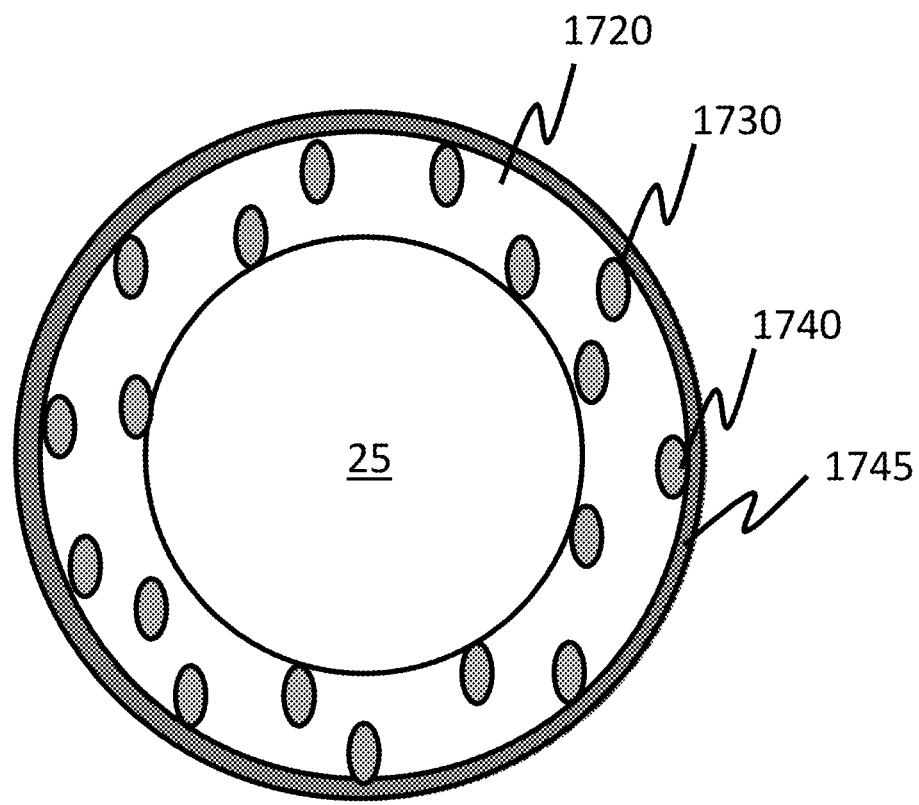

In some embodiments, the second water soluble polymer is positioned within the bulk of the first water soluble polymer (e.g., within the pores and/or interstices of the first water soluble polymer). In some embodiments, as illustrated in FIG. 20, the second water soluble polymer 1740 may be present as a coating 1745 on at least a portion of a surface of polymeric material 1720. Although FIG. 20 shows the second water soluble polymer as a coating on the first water soluble polymer and in the pores of the first water soluble polymer, it should be appreciated that in some embodiments, only a coating 1745 is present and the pores 1730 are not substantially filled with the second water soluble polymer 1740. Other configurations are also possible.

In some embodiments, article 1710 and/or article 1712 may be hollow (e.g., comprising a hollow core 1725). However, while FIGS. 19 and 20 are depicted having a hollow core, those of ordinary skill in the art would understand based upon the teachings of this specification that such a hollow core may not be present. That is to say, in some cases, the core 1725 of the article may be a bulk material without a hollow core 1725.

In some embodiments, the plurality of pores (e.g., of an article or of a first water soluble material, optionally having a second water soluble polymer positioned within at least a portion of said pores) have a particular mean pore size. In some embodiments, the mean pore size of the plurality of pores is less than or equal to 500 nm, less than or equal to 450 nm, less than or equal to 400 nm, less than or equal to 350 nm, less than or equal to 300 nm, less than or equal to 250 nm, less than or equal to 200 nm, less than or equal to 150 nm, less than or equal to 100 nm, less than or equal to 75 nm, less than or equal to 50 nm, less than or equal to 25 nm, less than or equal to 20 nm, or less than or equal to 15 nm. In some embodiments, the plurality of pores have a mean pore size of greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, or greater than or equal to 450 nm. Combinations of the above referenced ranges are also possible (e.g., less than or equal to 500 nm and greater than or equal to 10 nm). Other ranges are also possible. Mean pore size, as described herein, may be determined by mercury intrusion porosimetry of the material in a dehydrated state (i.e. having less than 5 w/w % water).

In some embodiments, at least a portion of the plurality of pores may be characterized as nanopores, e.g., pores having an average cross-sectional dimension of less than 1 micron. In some embodiments, at least a portion of the plurality of pores may be characterized as micropores, e.g., pores having an average cross-sectional dimension of less than 1 mm and greater than or equal to 1 micron. In some embodiments, at least 50% (e.g., at least 60%, at least 70%, at least 80%, at least 90%, at least 95%, at least 98%, at least 99%, at least 99.9%) of the plurality of pores have a diameter that is less than 1 micron, less than or equal to 800 nm, less than or equal to 600 nm, less than or equal to 500 nm, less than or equal to 450 nm, less than or equal to 400 nm, less than or equal to 350 nm, less than or equal to 300 nm, less than or equal to 250 nm, less than or equal to 200 nm, less than or equal to 150 nm, less than or equal to 100 nm, less than or equal to 75 nm, less than or equal to 50 nm, less than or equal to 25 nm, less than or equal to 20 nm, or less than or equal to 15 nm. In some cases, at least 50% of the plurality of pores have a diameter than is greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, greater than or equal to 450 nm, greater than or equal to 500 nm, greater than or equal to 600 nm, or greater than or equal to 800 nm. Combinations of the above referenced ranges are also possible (e.g., less than or equal to 1000 nm and greater than or equal to 10 nm). Other ranges are also possible.

The compositions and article described herein may have a particular porosity e.g., in a dehydrated state. In some embodiments, the article (or polymeric material) has a porosity of greater than or equal to 5%, greater than or equal to 10%, greater than or equal to 15%, greater than or equal to 20%, greater than or equal to 25%, greater than or equal to 30%, greater than or equal to 35%, greater than or equal to 40%, or greater than or equal to 45% in a dehydrated state. In some embodiments, the article (or polymeric material) has a porosity of less than or equal to 50%, less than or equal to 45%, less than or equal to 40%, less than or equal to 35%, less than or equal to 30%, less than or equal to 25%, less than or equal to 20%, less than or equal to 15%, or less than or equal to 10% in a dehydrated state. Combinations of the above-referenced ranges are also possible (e.g., greater than or equal to 5% and less than or equal to 50% in a dehydrated state.). Other ranges are also possible.

As described herein, in some embodiments, the article (or polymeric material) is substantially non-thrombogenic.

In some embodiments, the article (or polymeric material (e.g., polymeric material 1720 of FIGS. 19-20)) is hydrophilic. The term "hydrophilic" as used herein is given its ordinary meaning in the art and refers to a material surface having a water contact angle as determined by goniometry of less than 90 degrees. In some embodiments, a surface of the polymeric material of the article has a water contact angle of less than or equal to 45 degrees, less than or equal to 40 degrees, less than or equal to 35 degrees, less than or equal to 30 degrees, less than or equal to 25 degrees, less than or equal to 20 degrees, less than or equal to 15 degrees, less than or equal to 10 degrees, less than or equal to 5 degrees, or less than or equal to 2 degrees at an equilibrium water content state. In some embodiments, the surface of the polymeric material has a water contact angle of greater than or equal to 1 degree, greater than or equal to 2 degrees, greater than or equal to 5 degrees, greater than or equal to 10 degrees, greater than or equal to 15 degrees, greater than or equal to 20 degrees, greater than or equal to 25 degrees, greater than or equal to 30 degrees, greater than or equal to 35 degrees, or greater than or equal to 40 degrees at an equilibrium water content state. Combinations of the above-referenced ranges are also possible (e.g., greater than or equal to 1 degree and less than or equal to 45 degrees). Other ranges are also possible.

Equilibrium water content state, as used herein, refers the steady state of an article (or material) which does not gain (e.g., absorb) or lose bulk water content as determined when submerged in water at 25° C. without externally applied mechanical stresses. Those skilled in the art would understand that steady state (or equilibrium water content state) shall be understood to not require absolute conformance to a strict thermodynamic definition of such term, but, rather, shall be understood to indicate conformance to the thermodynamic definition of such term to the extent possible for the subject matter so characterized as would be understood by one skilled in the art most closely related to such subject matter (e.g., accounting for factors such as passive diffusion and/or Brownian motion).

In some embodiments, the article is substantially lubricious at an equilibrium water content state. For example, in some embodiments, the article (or polymeric material of the article) has a surface roughness of less than or equal to 1000 nm (Ra) at an equilibrium water content state. In some embodiments, the article (or polymeric material of the article) has a surface roughness (Ra) of less than or equal to 500 nm, less than or equal to 400 nm, less than or equal to 300 nm, less than or equal to 250 nm, less than or equal to 200 nm, less than or equal to 150 nm, less than or equal to 100 nm, less than or equal to 50 nm, less than or equal to 25 nm, less than or equal to 10 nm, or less than or equal to 5 nm at an equilibrium water content state. In some embodiments, the article (or polymeric material of the article) has a surface roughness (Ra) of greater than or equal to 5 nm at an equilibrium water content state, greater than or equal to 10 nm, greater than or equal to 25 nm, greater than or equal to 50 nm, greater than or equal to 100 nm, greater than or equal to 150 nm, greater than or equal to 200 nm, greater than or equal to 250 nm, greater than or equal to 300 nm, greater than or equal to 400 nm, or greater than or equal to 500 nm at an equilibrium water content state. Combinations of the above-referenced ranges are also possible (e.g., greater than or equal to 5 nm and less than or equal to 1000 nm). Other ranges are also possible.

In some embodiments, the article has a surface having a coefficient of friction of less than or equal to 0.10 at an equilibrium water content state. For example, the coefficient of friction of a surface of the article (or polymeric material of the article) is less than or equal to 0.1, less than or equal to 0.09, less than or equal to 0.08, less than or equal to 0.07, less than or equal to 0.06, less than or equal to 0.05, less than or equal to 0.04, less than or equal to 0.03, or less than or equal to 0.02. In some embodiments, the coefficient of friction of the surface of the article (or polymeric material of the article) is greater than or equal to 0.01, greater than or equal to 0.02, greater than or equal to 0.03, greater than or equal to 0.04, greater than or equal to 0.05, greater than or equal to 0.06, greater than or equal to 0.07, greater than or equal to 0.08, or greater than or equal to 0.09. Combinations of the above-referenced ranges are also possible (e.g., less than or equal to 0.1 and greater than or equal to 0.01). Other ranges are also possible. Advantageously, the compositions and articles described herein may have low sorption of substances such as therapeutic agents (and/or e.g., proteins) in the presence of a dynamic fluid comprising such substances. Such articles and compositions may be useful for use in subjects where, for example, the presence of the article should not substantially decrease the availability and/or concentration of therapeutic agents delivered to the subject (e.g., via the article). In some embodiments, administration of therapeutic agents via a fluid flowed within the articles described herein do not substantially reduce the concentration of the therapeutic agent within the fluid. In some cases, the article may not absorb and/or adsorb the therapeutic agent, e.g., during flow or use.

In some embodiments, less than or equal to 0.5 w/w % sorption of a therapeutic agent to the surface and/or bulk of the first water-soluble polymer occurs as determined at equilibrium water content after exposing the polymer to the therapeutic agent and flushing with 5 times the volume of the article with an aqueous solution, such as water or normal saline. In some embodiments, less than or equal to 0.5 w/w %, less than or equal to 0.4 w/w %, less than or equal to 0.3 w/w %, less than or equal to 0.2 w/w %, or less than or equal to 0.1 w/w % sorption of the therapeutic agent to the surface and/or bulk of the first water-soluble polymer occurs. In some embodiments, greater than or equal to 0.05 w/w %, greater than or equal to 0.1 w/w %, greater than or equal to 0.2 w/w %, greater than or equal to 0.3 w/w %, or greater than or equal to 0.4 w/w % sorption of the therapeutic agent to the surface and/or bulk of the first water-soluble polymer occurs. Combinations of the above-referenced ranges are also possible (e.g., less than or equal to 0.5 w/w % and greater than or equal to 0.05 w/w %). Other ranges are also possible.

Advantageously, the articles and compositions described herein may have desirable swelling characteristics (e.g., in water, in saline, in a fluidic environment of a subject).

In some embodiments, the articles described herein are in a dehydrated state. For example, in some embodiments, the articles (or polymeric materials) described herein have a water content of less than or equal to 5 w/w %, less than or equal to 4 w/w %, less than or equal to 3 w/w %, less than or equal to 2 w/w %, less than or equal to 1 w/w %, less than or equal to 0.8 w/w %, less than or equal to 0.6 w/w %, less than or equal to 0.4 w/w %, or less than or equal to 0.2 w/w % in the dehydrated state. In some embodiments, the articles (or polymeric materials) described herein have a water content of greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 2 w/w %, greater than or equal to 3 w/w %, or greater than or equal to 4 w/w %. Combinations of the above-referenced ranges are also possible (e.g., less than 5 w/w % and greater than or equal to 0.1 w/w %). Other ranges are also possible. The dehydrated state, as described herein, generally refers to the steady state determined under ambient conditions in which the article (or polymeric material) has no appreciable decrease in water content of less than 5 w/w % over 24 hours. In some embodiments, the articles described herein may comprise a coating or unbound porogen, such as a humectant coating, as described in more detail below.

Advantageously, the articles and compositions described herein may be configured for rapid swelling in the presence of an aqueous solution, such as water and/or saline. In some embodiments, the article (or polymeric material (e.g., polymeric material 1720 of FIGS. 19-20)) is configured to swell in an amount greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w % from a dehydrated state to an equilibrium water content state at 25° C., e.g., in a particular amount of time (e.g., less than or equal to 60 minutes), as described in more detail below. In some embodiments, the article (or polymeric material) is configured to swell in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, or less than or equal to 10 w/w % from a dehydrated state to an equilibrium water content state at 25° C., e.g., in a particular amount of time (e.g., less than or equal to 60 minutes) as described in more detail below. Combinations of the above-referenced ranges are also possible (e.g., greater than or equal to 5 w/w % and less than or equal to 50 w/w %). Other ranges are also possible.

In some embodiments, the article (or polymeric material (e.g., polymeric material 1720 of FIGS. 19-20)) is configured to swell in an amount greater than or equal to 5 w/w % from a dehydrated state to an equilibrium water content state in less than or equal to 60 minutes, less than or equal to 50 minutes, less than or equal to 40 minutes, less than or equal to 30 minutes, less than or equal to 20 minutes, less than or equal to 10 minutes, less than or equal to 5 minutes, or less than or equal to 2 minutes at 25° C. In some embodiments, the article (or polymeric material) is configured to swell in an amount greater than or equal to 5 w/w % from a dehydrated state to an equilibrium water content state in greater than or equal to 1 minute, greater than or equal to 2 minutes, greater than or equal to 5 minutes, greater than or equal to 10 minutes, greater than or equal to 20 minutes, greater than or equal to 30 minutes, greater than or equal to 40 minutes, or greater than or equal to 50 minutes at 25° C. Combinations of the above-referenced ranges are also possible (e.g., less than or equal to 60 minutes and greater than or equal to 1 minute). Other ranges are also possible.

In an exemplary embodiment, article (or polymeric material (e.g., polymeric material 20 of FIGS. 19-20)) is configured to swell to an equilibrium water content state (e.g., greater than or equal to 5 w/w %) in less than or equal to 60 minutes from a dehydrated state (e.g., less than 5 w/w %) in water. In some embodiments, the article (or polymeric material) is configured to swell to an equilibrium water content (e.g., greater than or equal to 5 w/w %) in less than or equal to 60 minutes from a dehydrated state (e.g., less than 5 w/w %) in standard normal saline. In another exemplary embodiment, the article (or polymeric material) is configured to swell to an equilibrium water content (e.g., greater than or equal to 5 w/w %) in less than or equal to 60 minutes from a dehydrated state (e.g., less than 5 w/w %) in normal saline.

In some embodiments, the article (or polymeric material (e.g., polymeric material 1720 of FIGS. 19-20)) has a particular length in the dehydrated state. In some embodiments, the article (or polymeric material) has an increase in overall length in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to its length in the dehydrated state. In some cases, the article (or polymeric material) has an increase in overall length in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to its length in the dehydrated state. Combinations of the above-referenced ranges are also possible (e.g., greater than or equal to 0.1% and less than or equal to 20%). Other ranges are also possible.

In some embodiments, the article (or polymeric material (e.g., polymeric material 1720 of FIGS. 19-20)) has a particular outer maximum cross-sectional dimension, such as an outer diameter, in the dehydrated state. In some embodiments, the article (or polymeric material) has an increase in an outer maximum cross-sectional dimension (e.g., outer diameter) in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to the maximum cross-sectional dimension (e.g., outer diameter) in the dehydrated state. In some cases, the article (or polymeric material) has an increase in the maximum cross-sectional dimension (e.g., outer diameter) in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to the maximum cross-sectional dimension (e.g., outer diameter) in the dehydrated state. Combinations of the above-referenced ranges are also possible (e.g., greater than or equal to 0.1% and less than or equal to 20%, greater than or equal to 0.1% and less than or equal to 10%). Other ranges are also possible.

In some embodiments, the article (or polymeric material) has a particular inner diameter in the dehydrated state (e.g., in an embodiment in which the article comprises a hollow core). In some embodiments, the article (or polymeric material) has an increase in the inner diameter in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to the inner diameter in the dehydrated state. In some cases, the article (or polymeric material) has an increase in the inner diameter in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to the inner diameter in the dehydrated state. Combinations of the above-referenced ranges are also possible (e.g., greater than or equal to 0.1% and less than or equal to 20%). Other ranges are also possible.

In some embodiments, the article comprises a polymeric material having desirable mechanical properties. For example, in some embodiments, the polymeric material has a Young's elastic modulus in the dehydrated state (e.g., less than 5 w/w % water content) of greater than or equal to 500 MPa, greater than or equal to 600 MPa, greater than or equal to 750 MPa, greater than or equal to 800 MPa, greater than or equal to 900 MPa, greater than or equal to 1000 MPa, greater than or equal to 1250 MPa, greater than or equal to 1500 MPa, greater than or equal to 1750 MPa, greater than or equal to 2000 MPa, greater than or equal to 2500 MPa, greater than or equal to 3000 MPa, greater than or equal to 3500 MPa, or greater than or equal to 4000 MPa. In some embodiments, the polymeric material has a Young's elastic modulus in the dehydrated state (e.g., less than 5 w/w % water content) of less than or equal to 5000 MPa, less than or equal to 4000 MPa, less than or equal to 3500 MPa, less than or equal to 3000 MPa, less than or equal to 2500 MPa, less than or equal to 2000 MPa, less than or equal to 1750 MPa, less than or equal to 1500 MPa, less than or equal to 1250 MPa, less than or equal to 1000 MPa, less than or equal to 900 MPa, less than or equal to 800 MPa, less than or equal to 750 MPa, or less than or equal to 600 MPa. Combinations of the above-referenced ranges are also possible (e.g., greater than or equal to 500 MPa and less than or equal to 5000 MPa). Other ranges are also possible.

In some embodiments, the polymeric material has a Young's elastic modulus at an equilibrium water content state of less than or equal to 300 MPa, less than or equal to 250 MPa, less than or equal to 200 MPa, less than or equal to 150 MPa, less than or equal to 100 MPa, less than or equal to 75 MPa, less than or equal to 50 MPa, less than or equal to 25 MPa, less than or equal to 20 MPa, or less than or equal to 10 MPa. In some embodiments, the polymeric material has a Young's elastic modulus at an equilibrium water content state of greater than or equal to 5 MPa, greater than or equal to 10 MPa, greater than or equal to 20 MPa, greater than or equal to 25 MPa, greater than or equal to 50 MPa, greater than or equal to 75 MPa, greater than or equal to 100 MPa, greater than or equal to 150 MPa, greater than or equal to 200 MPa, or greater than or equal to 250 MPa. Combinations of the above-referenced ranges are also possible (e.g., less than or equal to 300 MPa and greater than or equal to 5 MPa). Other ranges are also possible.

In some embodiments, the article comprises an osmotic agent. For example, in some embodiments, an osmotic agent may be added (e.g., to the pre-polymer) during formation of the article. In some embodiments, the osmotic agent is present in the polymeric material (e.g., after formation of the polymeric material) in an amount greater than or equal to 0.05 w/w %, greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 1.2 w/w %, greater than or equal to 1.4 w/w %, greater than or equal to 1.6 w/w %, or greater than or equal to 1.8 w/w %. In some cases, the osmotic agent may be present in the polymeric material (e.g., after formation of the polymeric material) in an amount of less than or equal to 2 w/w %, less than or equal to 1.8 w/w %, less than or equal to 1.6 w/w %, less than or equal to 1.4 w/w %, less than or equal to 1.2 w/w %, less than or equal to 1 w/w %, less than or equal to 0.8 w/w %, less than or equal to 0.6 w/w %, less than or equal to 0.4 w/w %, less than or equal to 0.2 w/w %, or less than or equal to 0.01 w/w %. Combinations of the above-referenced ranges are also possible (e.g., greater than or equal to 0.05 w/w % and less than or equal to 2 w/w %). Other ranges are also possible.

Non-limiting examples of suitable osmotic agents include phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments, the composition (e.g., comprising a polymeric material) does not comprise covalent crosslinking, as described in more detail below. In other embodiments, however, the composition comprises physical cross-linking (e.g., interpenetrating network, chain entanglement, and/or one or more bonds such as covalent, ionic, and/or hydrogen bonding). In a particular set of embodiments, no covalent crosslinking agents are used to form the polymeric material, the first water soluble polymer of the polymeric material, and/or the second water soluble polymer.

The first water soluble polymer may be present in the article in any suitable amount. For example, in some embodiments, the first water soluble polymer is present in the article in an amount of greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, or greater than or equal to 90 w/w % at an equilibrium water content state. In some embodiments, the first water soluble polymer is present in the article in an amount of less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, or less than or equal to 25 w/w % at an equilibrium water content state. Combinations of the above-referenced ranges are also possible (e.g., greater than or equal to 20 w/w % and less than or equal to 95 w/w %). Other ranges are also possible.

In some embodiments, the first water soluble polymer comprises or is selected from the group consisting of poly (vinyl alcohol), poly(acrylic acid), polyethylene glycol, poly (vinyl pyrrolidone), poly(methacrylic sulfobetaine), poly (acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly (2-hydroxymethylmethacrylate), and combinations thereof.

In an exemplary set of embodiments, the first water soluble polymer is poly(vinyl alcohol).

In some embodiments, the polymeric material comprises a mixture comprising the first water-soluble polymer and another (e.g., a third) water soluble polymer. In some embodiments, the third water soluble polymer comprises or is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof. The first and other (e.g., third) water soluble polymers may have different chemical compositions.

In some embodiments, the total weight of the first water soluble polymer and another (e.g., a third) water soluble polymer in the article is greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, greater than or equal to 90 w/w %, greater than or equal to 95 w/w %, greater than or equal to 98 w/w %, or greater than or equal to 99 w/w % at an equilibrium water content state. In some embodiments, the total weight of the first water soluble polymer and another (e.g., a third) water soluble polymer in the article in an amount of less than or equal to 100 w/w %, less than or equal to 90 w/w %, less than or equal to 98 w/w %, less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, or less than or equal to 25 w/w % at an equilibrium water content state. Combinations of the above-referenced ranges are also possible (e.g., greater than or equal to 20 w/w % and less than or equal to 100 w/w %). Other ranges are also possible.

In some embodiments, the ratio of the first water soluble polymer to the third water soluble polymer present in the article is less than or equal to 100:0, less than or equal to 99:1, less than or equal to 95:5, less than or equal to 90:10, less than or equal to 80:20, less than or equal to 70:30, less than or equal to 60:40, or less than or equal to 55:45. In some embodiments, the ratio of the first water soluble polymer to the third water soluble polymer present in the article is greater than or equal to 50:50, greater than or equal to 60:40, greater than or equal to 70:30, greater than or equal to 80:20, greater than or equal to 90:10, greater than or equal to 95:5, or greater than or equal to 99:1. Combinations of the above-referenced ranges are also possible (e.g., less than or equal to 100:0 and greater than or equal to 50:50). Other ranges are also possible.

As described above and herein, in some embodiments, the article comprises a second water soluble polymer (e.g., second water soluble polymer 1740) disposed within at least a portion of the plurality of pores (e.g., plurality of pores 1730) of the polymeric material (e.g., polymeric material 1720). In some embodiments, the second water soluble polymer comprises or is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof. In some embodiments, the second water soluble polymer is poly(acrylic acid). The second water soluble polymer may have a different chemical composition from that of the first (e.g., and optionally third) water soluble polymers.

The second water soluble polymer (e.g., second water soluble polymer 1740) may be present in the article in any suitable amount. For example, in some embodiments, the second water soluble polymer is present in the article in an amount of greater than or equal to 0.05 w/w %, greater than or equal to 0.1 w/w %, greater or than or equal to 0.2 w/w %, greater than or equal to 0.5 w/w %, greater than or equal to 1.0 w/w %, greater than or equal to 2.0 w/w %, greater than or equal to 3.0 w/w %, greater than or equal to 4.0 w/w %, greater than or equal to 5.0 w/w %, greater than or equal to 10 w/w %, greater than or equal to 20 w/w %, greater than or equal to 30 w/w %, greater than or equal to 40 w/w %, greater than or equal to 50 w/w %, greater than or equal to 60 w/w %, greater than or equal to 70 w/w %, greater than or equal to 80 w/w %, or greater than or equal to 90 w/w % at an equilibrium water content state. In some embodiments, the second water soluble polymer 40 is present in the article in an amount of less than or equal to 95 w/w %, less than or equal to 90 w/w %, less than or equal to 80 w/w %, less than or equal to 70 w/w %, less than or equal to 60 w/w %, less than or equal to 50 w/w %, less than or equal to 40 w/w %, less than or equal to 30 w/w %, less than or equal to 20 w/w %, less than or equal to 10 w/w %, less than or equal to 5.0 w/w %, less than or equal to 4.0 w/w %, less than or equal to 3.0 w/w %, less than or equal to 2.0 w/w %, less than or equal to 1.0 w/w %, less than 0.5 w/w %, less than 0.2 w/w %, or less than 0.1 w/w % at an equilibrium water content state. In some embodiments, 0 w/w % of the second water soluble polymer is present. Combinations of the above-referenced ranges are also possible (e.g., greater than or equal to 0.05 w/w % and less than or equal to 95 w/w %). Other ranges are also possible.

In some embodiments, the water-soluble polymer (e.g., the first water soluble polymer, the second water soluble polymer, the third water soluble polymer) has a particular molecular weight. In some embodiments, the molecular weight of the water soluble polymer (e.g., each, independently, the first water soluble polymer, the second water soluble polymer, or the third water soluble polymer) may be greater than or equal to 40 kDa, greater than or equal to 50 kDa, greater than or equal to 75 kDa, greater than or equal to 100 kDa, greater than or equal to 125 kDa, greater than or equal to 150 kDa, greater than or equal to 175 kDa, greater than or equal to 200 kDa, greater than or equal to 250 kDa, greater than or equal to 300 kDa, greater than or equal to 350 kDa, greater than or equal to 400 kDa, greater than or equal to 450 kDa, greater than or equal to 500 kDa, greater than or equal to 600 kDa, greater than or equal to 700 kDa, greater than or equal to 800 kDa, greater than or equal to 900 kDa, greater than or equal to 1000 kDa, greater than or equal to 1500 kDa, greater than or equal to 2000 kDa, greater than or equal to 3000 kDa, or greater than or equal to 4000 kDa. In some embodiments, the molecular weight of the water soluble polymer (e.g., each, independently, the first water soluble polymer, the second water soluble polymer, or the third water soluble polymer) may be less than or equal to 5000 kDa, less than or equal to 4000 kDa, less than or equal to 3000 kDa, less than or equal to 2000 kDa, less than or equal to 1500 kDa, less than or equal to 1000 kDa, less than or equal to 900 kDa, less than or equal to 800 kDa, less than or equal to 700 kDa, less than or equal to 600 kDa, less than or equal to 500 kDa, less than or equal to 450 kDa, less than or equal to 400 kDa, less than or equal to 350 kDa, less than or equal to 300 kDa, less than or equal to 250 kDa, less than or equal to 200 kDa, less than or equal to 175 kDa, less than or equal to 150 kDa, less than or equal to 125 kDa, less than or equal to 100 kDa, less than or equal to 75 kDa, or less than or equal to 50 kDa. Combinations of the above-referenced ranges are also possible (e.g., a molecular weight of greater than or equal to 40 kDa and less than or equal to 5000 kDa). Other ranges are also possible.

In some embodiments, the articles (and/or polymeric materials) described herein are, or are configured for use with, a medical device such as a catheter, a balloon, a shunt, a wound drain, an infusion port, a drug delivery device, a tube, a contraceptive device, a feminine hygiene device, an endoscope, a graft, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device. In some embodiments, the catheter is selected from the group consisting of central venous catheters, peripheral central catheters, midline catheters, peripheral catheters, peripheral port catheters, central venous port catheters, tunneled catheters, dialysis access catheters, urinary catheters, neurological catheters, epidural catheters, percutaneous transluminal angioplasty catheters and/or peritoneal catheters. Some catheters may be suitable for drainage, urinary, and/or dialysis applications. Other suitable uses are described in more detail, below.

Figure 21:
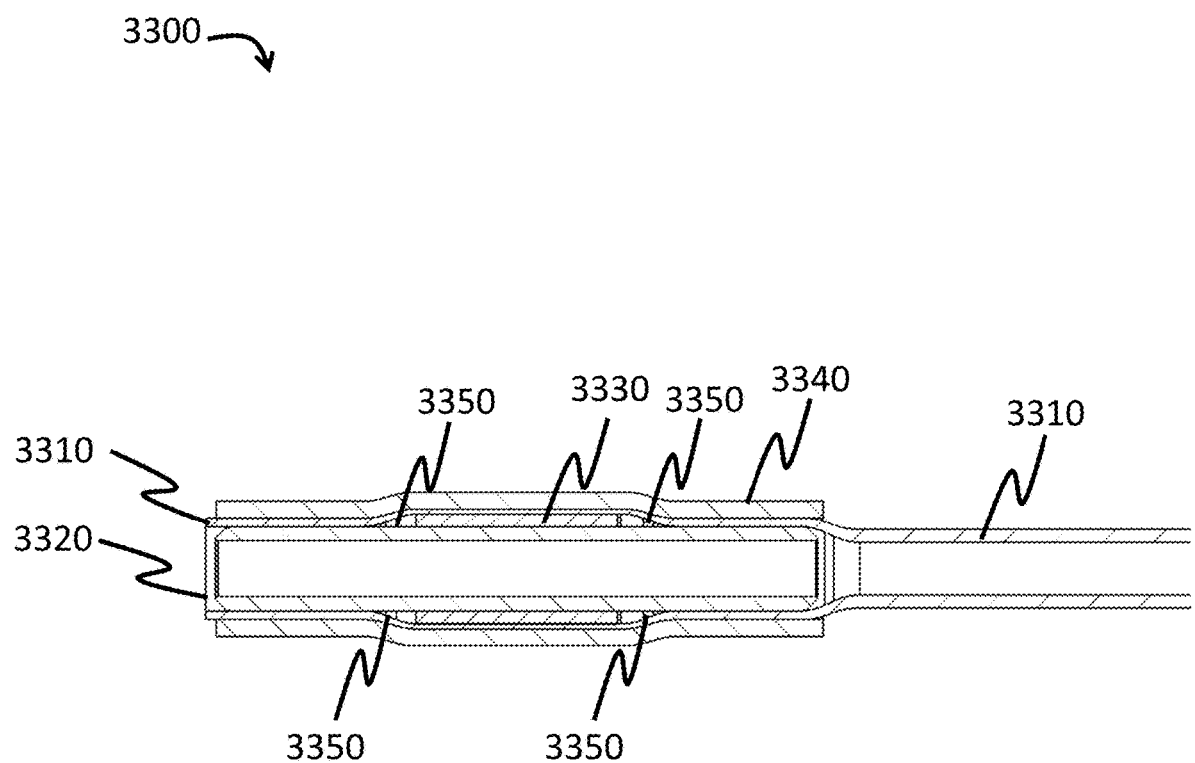
FIGS. 21-22 illustrate articles comprising two components, consistent with some embodiments.
Figure 22:
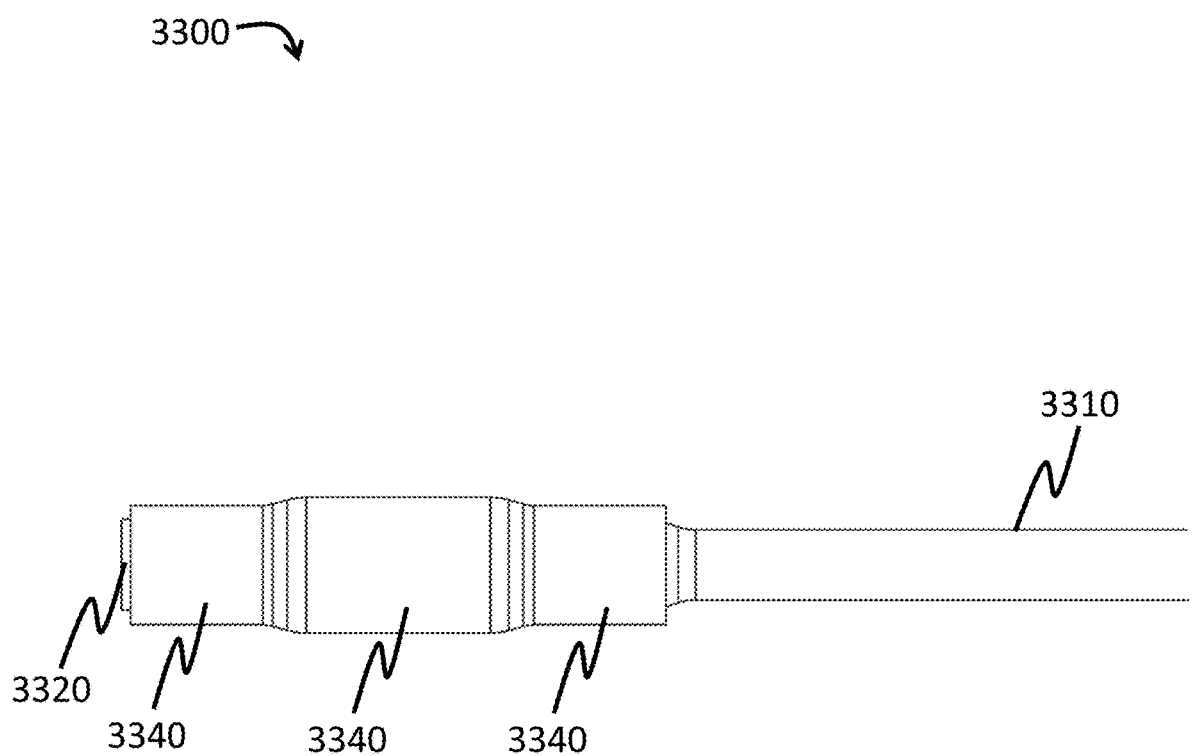

In some embodiments, the article comprises a first component comprising a polymeric material (e.g., comprises a water-soluble polymer) and a second component adjacent the first component. For example, in some cases, the second component is mechanically coupled to the first component. In some such embodiments, the second component may comprise a plurality of surface features configured to mechanically retain the second component within or on the first component. In some embodiments, as illustrated in FIGS. 21-22, article 3300 comprises first component 3310 (e.g., an article such as article 1710 of FIG. 19 or article 1712 of FIG. 20) and second component 3320 (e.g., an extension, a connector, a luer lock, a suture wing, a second article such as article 1710 of FIG. 19 or article 1712 of FIG. 20), adjacent first component 3310. In some embodiments, a first thermoplastic layer 3330 is disposed between first component 3310 and second component 3320. In some embodiments, optional second thermoplastic layer 3340 is adjacent (e.g., in contact with an external surface of) first component 3310. In some cases, second component 3320 may comprise plurality of surface features 3350 associated with first component 3310, such that the second component is mechanically retained to (e.g., within, on, adjacent) first component 3310.

In some embodiments, the second component may be a connector (e.g., to a medical component and/or a medical device). In some embodiments, the second component may be selected from the group consisting of an extender, a connector, a luer lock, and a suture wing. In some embodiments, the second component may be another article, such as the articles described herein, comprising a polymeric material.

In some embodiments, the article comprises a first thermoplastic layer disposed between the first component and the second component (e.g., to aid with mechanical retention between the first and second components). In some cases, a second thermoplastic layer may be in contact with an external surface of the first component. For instance, the second thermoplastic layer may cover both a portion of the second component and a portion of the first component. Each thermoplastic layer may comprise a suitable thermoplastic material. In some embodiments, the first thermoplastic material and/or second thermoplastic material each independently comprise or are selected from the group consisting of polyurethane elastomers, silicone elastomers, silicone-polyurethane copolymer, polyethylene, polypropylene, styrene isoprene butadiene copolymer, homopolymers and copolymers of vinyl acetate such as ethylene vinyl acetate copolymer, polyvinylchlorides, homopolymers and copolymers of acrylates and methacrylates, polyvinylpyrrolidone, 2-pyrrolidone, polyacrylonitrile butadiene, polycarbonates, polyamides, polyether block amide, fluoropolymers (including homopolymers and copolymers of polytetrafluoroethylene and polyvinyl fluoride), fluorinated ethylene propylene, polystyrenes, homopolymers and copolymers of styrene acrylonitrile, homopolymers and copolymers of styrene butadiene, cellulose acetate, homopolymers and copolymers of acrylonitrile butadiene styrene, polymethylpentene, polysulfones, polyesters, polyimides, polyisobutylene, polymethylstyrene, polyoxymethylene, and homopolymers and copolymers of poly(lactic acid), poly(glycolic acid), and poly(caprolactone). In some embodiments, the first thermoplastic material and/or the second thermoplastic material at least partially swells in water at 25° C.

In some embodiments, the second component is thermally bonded to the first component. In some embodiments, the second component is solvent-bonded to the first thermoplastic material. In some embodiments, the solvent may be selected based on the ability to solvate both the first component and/or the second component. Non-limiting examples of suitable solvents include: tetrahydrofuran, toluene, N,N-dimethylformamide, N,N-dimethylacetamide, chloroform, dichloromethane, ethyl acetate, acetone, acetonitrile, dimethyl sulfoxide, nitromethane, propylene carbonate, diethyl ether, 1,4-doxane, benzene, cyclohexane, hexane, cyclopentane, pentane, formic acid, n-butanol, isopropyl alcohol, ethanol, methanol, acetic acid, hexafluoroisopropanol, trifluoroacetic acid, water, and combinations thereof. In an exemplary embodiment, a water-swelling polyurethane is solvent bonded to a hydrophobic polyurethane using tetrahydrofuran.

In some embodiments, the second component has a Young's elastic modulus greater than a Young's elastic modulus of the first component in the dehydrated state and/or in the equilibrium water content state. In some embodiments, the second component has a Young's elastic modulus greater than a Young's elastic modulus of the first component in the equilibrium water content state, but less than a Young's elastic modulus of the first component in the dehydrated state.

In some embodiments, the second component comprises a plurality of surface features, such as protrusions or spikes. The surface features may be present at the interface between the first component and the second component so as to mechanically retain connection between the two components. In some embodiments, the plurality of surface features comprise rounded edges. In some embodiments, the plurality of surface features comprise rounded edges, sharp edges, blunt edges, flairs, bulges, and/or raised features. In some embodiments, the plurality of surface features comprise a plurality of barbs and/or bulges. Other surface features are also possible.

In some embodiments, the plurality of surface features may have a particular radius of curvature (e.g., at the surface adjacent the first component). For example, in some cases, at least a portion of the plurality of surface features have a radius of curvature of greater than or equal to 0.1, greater than or equal to 0.2, greater than or equal to 0.3, greater than or equal to 0.5 greater than or equal to 0.7 greater than or equal to 0.9, greater than or equal to 1, greater than or equal to 1.1, greater than or equal to 1.2, greater than or equal to 1.5, greater than or equal to 2, greater than or equal to 2.5, greater than or equal to 3, greater than or equal to 3.5, greater than or equal to 4, or greater than or equal to 4.5 times the radius of curvature of an inner surface of the article (e.g., the hollow portion of the article). In some embodiments, at least a portion of the plurality of surface features have a radius of curvature of less than or equal to 5, less than or equal to 4.5, less than or equal to 4, less than or equal to 3.5, less than or equal to 3, less than or equal to 2.5, less than or equal to 2, less than or equal to 1.5, less than or equal to 1.2, less than or equal to 1.1, less than or equal to 1, less than or equal to 0.9, less than or equal to 0.7, less than or equal to 0.5, less than or equal to 0.3, or less than or equal to 0.2 times the radius of curvature of an inner surface of the article (e.g., the hollow portion of the article). Combinations of the above-referenced ranges are also possible (e.g., greater than or equal to 0.1 and less than or equal to 5 times). Other ranges are also possible.

In some embodiments, the joint strength between the first component and the second component (e.g., at an interface between the first component and the second component) is greater than or equal to 10 N, greater than or equal to 15 N, greater than or equal to 20 N, greater than or equal to 25 N, greater than or equal to 30 N, greater than or equal to 40 N, greater than or equal to 50 N, greater than or equal to 60 N, greater than or equal to 70 N, or greater than or equal to 75 N. In some embodiments, the joint strength is less than or equal to 100 N, less than or equal to 75 N, less than or equal to 70 N, less than or equal to 60 N, less than or equal to 50 N, less than or equal to 40 N, less than or equal to 30 N, less than or equal to 25 N, less than or equal to 20 N, or less than or equal to 15 N. Combinations of the above-referenced ranges are also possible (e.g., greater than or equal to 10 N and less than or equal to 100 N). Other ranges are also possible. Joint strength may be determined by determining the maximum load at break using an INSTRON tensile tester (Model 3343, 500 N load cell) with pneumatic grips @40 psi and a grip strength of 1 kN. The components may be pulled at 400 mm/min starting from a 20 mm gap distance.

In some embodiments, an interface between the first component and the second component is fluidically sealed. For example, in some embodiments, the interface between the first component and the second component is configured to withstand an injection pressure (an injection of fluid through the first component and into the second component fluidically connected to the first component) of greater than or equal to 50 PSI, greater than or equal to 75 PSI, greater than or equal to 100 PSI, greater than or equal to 125 PSI, greater than or equal to 150 PSI, greater than or equal to 175 PSI, greater than or equal to 200 PSI, greater than or equal to 225 PSI, greater than or equal to 250 PSI, greater than or equal to 300 PSI, or greater than or equal to 350 PSI. In some embodiments, the interface between the first component and the second component is configured to withstand an injection pressure of less than or equal to 500 PSI, less than or equal to 400 PSI, less than or equal to 350 PSI, less than or equal to 300 PSI, less than or equal to 250 PSI, less than or equal to 225 PSI, less than or equal to 200 PSI, less than or equal to 175 PSI, less than or equal to 150 PSI, less than or equal to 125 PSI, less than or equal to 100 PSI, or less than or equal to 75 PSI. Combinations of the above-referenced ranges are also possible (e.g., greater than or equal to 50 PSI and less than or equal to 500 PSI). Other ranges are also possible.

As described herein, in some embodiments, the article comprises at least a first thermoplastic layer disposed between the first component and the second component. In some embodiments, the second component is placed on or adjacent to the first component prior to sorption of a second water-soluble polymer. In some embodiments, the second component is placed on or adjacent to the first component after sorption of a second water-soluble polymer and after a re-extraction of the second water-soluble polymer with a solvent. In some embodiments, the article comprises a first component comprising a water-soluble polymer and a plurality of pores, a second component comprising a first thermoplastic material positioned within at least a portion of the plurality of pores, and a third component comprising a second thermoplastic material associated with (e.g., adjacent, directly adjacent, or on) the second component.

These materials can be made as tough, high strength materials having lubricious and biocompatible surfaces. Nanoporous and microporous solids are described herein that have a particularly high Young's modulus and tensile strength. A nanoporous material is a solid that contains interconnected pores of up to 100 nm in diameter. Processes for making hydrogels are also described. Hydrophilic polymers may be used to make these various porous solids so that a hydrophilic solid is obtained. The water content of a nanoporous or a microporous solid can be high, e.g., 50% w/w at EWC. The water content of a hydrogel may be higher, for example, up to 90% w/w in principle. The porous solid materials can be used to make various devices, including medical catheters and implants with significant reductions in adsorption and/or adhesion of biological components to their surfaces.

These or other porous materials may be processed to include polymers that are bulk-incorporated into pores of the solid. An embodiment of the material is a porous material comprising water soluble polymers entrapped in pores of the material. Polymers entrapped by this method have been observed to be present in the pores and to remain in the pores after repeated hydration and dehydration. The entrapped polymers provide a surface that is scratch-resistant and effectively permanent, with the incorporated polymer providing desirable properties beyond the outer surface of the material. In aqueous medium, hydrophilic polymers entrapped by this method are hydrated to extend beyond the surface to enhance biocompatibility and lubricity.

Processes for making the material can include extrusion so that devices with a high aspect ratio may be created. An embodiment of a process for making the materials involves heating a mixture that comprises at least one water soluble polymer and a solvent to a temperature above the melting point of the polymer solution forming the mixture in a solvent-removing environment resulting in a crosslinked matrix and continuing to remove the solvent until the crosslinked matrix is a microporous or a nanoporous solid material. The crosslinking can take place while cooling the mixture and/or in the solvent-removing environment. Further polymers may be incorporated into pores of the material.

The articles (e.g., catheters) described herein may be made using any suitable process. Exemplary methods for making such catheters can be found in, for example U.S. Patent Publication No. 2018/0369454 entitled "HIGH STRENGTH POROUS MATERIALS INCORPORATING WATER SOLUBLE POLYMERS" and U.S. Patent Publication No. 2020/0230295 entitled "HIGH STRENGTH POROUS MATERIALS FOR CONTROLLED RELEASE", each of which is incorporated herein by reference, for all purposes.

Artisans reading this disclosure will be able to adapt its principles in light of what is known about extrusion or other forming arts to make alternative processes and devices that achieve the same end products as described herein. A scaled-up embodiment of this process may be adapted for use with, for example, a multi-zone screw extruder, with the solvent mixture provided via a suitable injector or a hopper and the zones controlled to provide a cold extrusion. Features such as the syringe pump can be replaced by a suitably metered and controlled liquid or solid polymer feed system.

In some embodiments, processes herein are free of freeze-thaw processes and/or free of a freezing process and/or free of a thawing process. Further the processes can be used to make solid porous materials that have little or no swelling, e.g., 0%-100% w/w swelling at EWC, even in an absence of covalent crosslinking agents Artisans will immediately appreciate that all ranges and values between the explicitly stated bounds are contemplated, with, e.g., any of the following being available as an upper or lower limit: 0, 5, 10, 15, 20, 25, 30, 40, 50, 60, 70, 80, 90, 95, 100% w/w, with swelling measured as % swelling=100×(Total weight at EWC-dry weight)/dry weight, with the dry weight being the weight of the material without water.

In some embodiments, the extruded samples have a horizontal chain orientation and alignment along the length of samples (in direction of extrusion). A polymeric chain orientation produced by the extrusion process. Without wishing to be bound by theory, it is believed that this horizontal chain orientation and alignment along the length of the samples contributes to the inner diameter and/or outer diameter increasing by a larger percentage than the percentage increase in length when the samples swell, in some embodiments.

In some embodiments, it is useful to have a combination of one or more of: extrusion of a hydrophilic polymer in a solvent; a cold extrusion, and extrusion into a bath that quickly removes solvent from the extrudate. Further, in some embodiments, additional solvent-removing and/or annealing processes provide further utility for making desirable porous solids.

In some embodiments, requirements for a nanoporous material include high polymer concentrations of more than about 10% w/w in the polymer-solvent mixture with high levels of crosslinking. Artisans will immediately appreciate that all ranges and values between the explicitly stated bounds are contemplated, with, e.g., any of the following being available as an upper or lower limit: 10, 12, 15, 16, 17, 18, 19, 20, 25, 30, 35, 40, 45, 50, 55, 60, 70, 80, 90, 95, 99% w/w of the polymer in the total weight of the polymer-solvent mixture. In some embodiments, the polymer is to be substantially solvated, meaning it is a true solution or at least half the polymer is dissolved and the rest is at least suspended. In some embodiments, the solvation of the polymer contributes to the alignment of the polymer chains in an extrusion and to crosslinking among the polymers. Without being bound to a particular theory, it is likely that high concentration of the starting polymer-solvent mixture can help with this. And the probable chain alignment of the material as it passes through a die, according to some embodiments, is thought to promote more intrapolymer versus interpolymer crosslinking. An extrudate or an otherwise formed mixture entering a desolvating environment, whether gas or liquid, is thought to further collapse pore structure before the densely concentrated polymer has completely crosslinked, in some embodiments, thereby improving chain proximity and promoting additional crosslink density. Depositing the extruded or otherwise formed material directly into a solvent removing environment is helpful in some embodiments. In some embodiments, further solvent-removal can be continued to collapse the material until reaching a desired end point in structure and/or properties. An annealing process can further contribute to strength in some embodiments.

Frozen methods, on the other hand, rely on increased strengthening by forcing super-concentrated microregions to also achieve chain proximity and improve crosslink density, but retain a macro porosity due to the presence of ice crystals in the total gel structure. Desolvation creates forced super-concentrated microregions but these do not create macropores. In contrast, a pre-established gel prior to a dehydration or freezing is by nature of that process formed with macropores. Further, the work of the inventors indicates that such nanoporous solids have greater strength than macroporous materials.

Hydrogels can also be made by using a lower polymer concentration in the polymer-solvent mixture, generally less than 10% w/w of polymer in the polymer-solvent mixture. Artisans will immediately appreciate that all ranges and values between the explicitly stated bounds are contemplated, with, e.g., any of the following being available as an upper or lower limit: 2, 5, 7, 8, 9, 10% w/w of the polymer in the total weight of the polymer-solvent mixture. Further, or alternatively, the polymer-solvent mixture is not extruded into a solvent removing environment.

Microporous materials may be made with process conditions intermediate to nanoporous solids and hydrogels. One embodiment is to prepare a material using conditions comparable to making a nanoporous material but to stop solvent removal before solvent removal reaches a nanoporous solid structure.

Extrusion of hydrophilic polymers in a solvent is helpful to make high strength materials. Use of a solvent in an extrusion starting material is, at the least, uncommon. Typically, an extrusion uses a solid material that has been heated to a flowable temperature and then extruded, and later cooled by a variety of methods. For instance, it is believed that thermoplastic extrusion of a pure PVA is possible. But such an extrusion would lack the polymeric structure that is needed to make porous solids and would instead exhibit properties more similar to a conventional thermoplastic material. According to a theory of operation, a pure PVA extrusion would lack the quality of hydrogen bonding that takes place in an aqueous ionic solvent state. A temperature suitable for preparing the PVA to be flowable in an extrusion would create a poorly cohesive material at the die head so that a continuous shape does not form. It was difficult to make extruded PVAs to form high aspect shapes, e.g., tubes, and to use them in an extrusion process. Viscosities of PVA and other hydrophilic polymers are high, and difficult to get into solution. It was observed that a narrow working band of temperature was particularly useful, e.g., 85-95° C. Below about 85° C., PVA failed to truly melt, and thus did not become completely amorphous for extrusion. Above about 95° C., losses to boiling and evaporation made the process ineffective. These temperature ranges could be offset by increasing pressure above atmospheric, but a pressurized system is challenging to use and to scale. The processes are usefully performed at a temperature below a boiling point of the polymer-solvent materials.

The cohesive strength of the flowing polymer-solvent mixture was weak when exiting the die. The use of a core to support the mixture at the die is useful to hold the shape at the die. This condition is in contrast to a typical core extrusion used as a coating process, e.g., for coating wires for a mobile telephone charger. A typical process that avoids use of a solvent or a significant solvent concentration has a relatively higher cohesive strength that it exits the die that is readily capable of holding a tube, and do not relying on active bonding such as the hydrogen bonding in hydrophilic polymers that form the solid material in a coherent shape as it moves out of the die.

Passing the formed polymer-solvent mixture into solvent removal environment was useful. Most extrusions do not use bath temperatures at or below room temperature. Moreover, the use of a solvent removing bath is atypical relative to conventional processes the bath or other solvent removing environment helps solidify the extruded material sufficiently that it remains stable and concentric on the core, otherwise the melt would run into a tear drop shape. It would also be destroyed in the attempt to collect it at the end of the extrusion as it would still be molten. Conventional baths containing water would cause the PVA or similar hydrophilic polymer material to lose shape due to swelling, dissolution, or both. Molding processes that involve preparation of a polymer-solvent mixture that is formed in a mold and then processed into a solvent-removing environment do not have the advantages of alignment of chains observed in an extrusion. However, a suitably controlled temperature and solvent removal can yield materials with a high strength and controlled pore structure.

The porous solids are highly lubricious and can be used in a hydrated state and can be conveniently bonded to other materials. In the case of a catheter, for instance, extensions, luer locks, suture wings, and the like are useful. In some embodiments, copolymer extrusion is useful in ranges of the second polymer from 0.1% to 10% w/w or no more than 10% w/w of the first polymer, with no more than 5% w/w also being useful. Artisans will immediately appreciate that all ranges and values between the explicitly stated bounds are contemplated, with, e.g., any of the following being available as an upper or lower limit: 0.1, 0.2, 0.4, 0.5, 0.8, 1, 2, 3, 4, 5, 6, 8, 10% w/w.

In some embodiments, salts are useful to manipulate the strength of the materials. Without being limited to a particular theory, it is likely the salts are part of the physical crosslinking, in effect acting as small molecular weight crosslinkers between the polymer chains.

Some embodiments for polymer blends include at least one first hydrophilic polymer and at least one second hydrophilic polymer in a solvent that is extruded as described herein. Examples include combinations of one or more of PVA, PAA, PEG, PVP, polyalkylene glycols, a hydrophilic polymer, and combinations thereof. Examples of concentrations include the at least one second hydrophilic polymer being present at 1 part to 10,000 parts of the first hydrophilic polymer. Artisans will immediately appreciate that all ranges and values between the explicitly stated bounds are contemplated, with, e.g., any of the following being available as an upper or lower limit: 1, 2, 10, 100, 1000, 1500, 2000, 2500, 3000, 4000, 5000, 6000, 7000, 8000, 9000, 10000 parts. Examples of concentrations of polymers in a polymer-solvent mixture include a first polymer present at a first concentration and one or more further polymers present at a second concentration, with the first polymer concentration and the further polymer concentration being independently selected from 0.1-99%, e.g., 0.1, 0.2, 0.3, 0.4, 0.5, 0.6, 1, 2, 3, 4, 5, 6, 7, 8, 9, 10, 11, 12, 13, 14, 15, 16, 17, 18, 19, 20, 25, 30, 33, 35, 40, 45, 50 55, 60, 65,70, 75,80, 85, 90, 95% w/w. Further, non-hydrophilic polymers and/or non-hydrophilic blocks in block polymers, may be present, with concentrations of such polymers and/or such blocks generally being less than about 10% w/w, e.g., 0.1, 0.2, 1, 2, 3, 4, 5, 6, 7, 8, 9, 10% w/w.

Some embodiments include porous matrices conditioned with water soluble polymers that lose no more than 20-90% w/w of the water-soluble polymer under comparable conditions; Artisans will immediately appreciate that all ranges and values between the explicitly stated bounds are contemplated, e.g., 20, 25, 30, 33, 40, 50, 60, 70, 80, 90% w/w.

In some embodiments, bulk incorporated materials may present a monolayer at the surface. The term monolayer means a layer that is a single molecule thick. The monolayer does not rely on cohesion between the molecules of the monolayer to remain stably present at the surface. At least one water soluble polymer forms the monolayer. In contrast, even a thin polymer coating that is cross-linked to itself has a thickness corresponding to the thickness of the network formed by the cross-linked polymers. For example, it may be possible to create a cross-linked PVA coating on a surface but such a coating relies on interconnections between molecules of the PVA and necessarily forms a crosslinked network. Accordingly, embodiments include a water-soluble polymer present on a surface of a porous solid without covalent bonding to the surface and without the polymer being part of a network.

In some embodiments, the bulk incorporated polymers are durably incorporated. In contrast, a layer of water soluble materials merely adsorbed to an underlying material, e.g., applied by dip coating or spraying, can be essentially removed from a hydrophilic substrate in most or all circumstances meaning at least 90% w/w of the materials can be separated from the underlying material in aqueous solution, e.g., 90° C. for 24 hours in physiological saline. Covalently bonded materials will not be removed under these conditions and some physically crosslinked networks of water-soluble polymers might not be removed but such networks are not preferable compared to a bulk incorporated polymer; for instance, they would likely be more thrombogenic or less durable. Covalent bonding involves use of chemically reactive moieties that can be avoided by bulk incorporation processes.

Processes are provided herein to create biocompatible porous solids such as microporous or nanoporous solid materials that possess low protein adsorption properties and provide a basis for non-biofouling devices. Modification of starting polymer concentration, molecular weight, solvent removal, forming processes, and hardening/annealing processes may be utilized to provide surface properties with reduced protein adsorption and other properties. Some embodiments include creation of various continuous shapes through extrusion of a polymeric mixture. The mixture may be further hardened and annealed. These processes may be used to create a tough and highly lubricious material.

Embodiments include polymeric mixtures extruded into shapes possessing single or multiple lumens, of varied diameters and wall thickness.

An embodiment of a process for making a nanoporous solid material comprises heating a mixture that comprises a polymer and a solvent (a polymeric mixture), extruding the mixture into a solvent-removing environment, and removing the solvent from the crosslinked matrix until a nanoporous solid material is formed. One or more of these actions may be combined, depending on the process. Further, cooling the mixture as it passes out of the die is useful. Without being bound to a specific theory of operation, it appears that crosslinking the polymer during passage through the die initially forms a porous matrix that is not a true nanoporous solid material because, although it has spaces between polymer strands, it does not have a pore-structure. As the solvent is removed under appropriate conditions, the crosslinked structure becomes a nanoporous solid. The crosslinking starts when the polymeric mixture is extruded through a die, and as the mixture is cooled. The crosslinking may continue while the solvent is removed. The transition to form the nanoporous material takes place as the solvent is removed and, in general, is believed to be completed or essentially completed (meaning 90% or more) at this stage. The resultant material may be further processed by annealing with or without a presence of further solvents, or plasticizers. This process, and the other extrusion or other formation processes and/or materials set forth herein, including bulk incorporation processes, may be free of one or more of: covalent crosslinking agents, agents that promote covalent crosslinks, radiation that crosslinks polymer chains, freezing, thawing, freeze-thaw cycles, more than one freeze-thaw cycle, ice-crystal formation, foaming agents, surfactants, hydrophobic polymers, hydrophobic polymer segments, reinforcing materials, wires, braids, non-porous solids, and fibers.

The porous materials may be made by an extrusion process that comprises passing a polymeric mixture through a die into a cooling environment. The cooling environment may further be a solvent-removing environment. It is a dehydrating environment when the solvent is water. The die may have a core that passes through it so that the polymeric mixture may be formed around the core. Further solvent-removal environments and/or annealing environments may be used.

The extrusion process for a polymer-solvent mixture may be performed as a cold extrusion. The term cold extrusion refers to a process that involves passing a polymer-solvent mixture through a die and does not require heating the polymer-solvent mixture above its boiling point during the entire process of preparing the polymer-solvent mixture and extruding it. Accordingly, in a cold extrusion, the die head is kept below a boiling point of the polymer-solvent mixture. Although many solvents may be used, water is often a useful solvent in which case the die head is kept at 100° C. or less, although colder temperatures may be useful, as discussed above.

The term polymeric mixture refers to a polymer that is in solution, dissolved, or suspended in a solvent. A solvent may be, e.g., water, aqueous solution, an organic solvent, or combinations thereof. Heating the polymeric mixture may comprise heating the mixture to a temperature above the melting point of the polymer. In general, the solution transitions from a cloudy to a clear state when it reaches the melt point. An aqueous solution contains water, for instance from 10-100% (w/w or v/v) of the liquid being water; Artisans will immediately appreciate that all ranges and values between the explicitly stated bounds are contemplated, e.g., 10, 20, 30, 40, 50 60, 70, 80, or 90% or at least one of the same.

Extrusion is a useful process for forming the materials. Other forming processes may be used, for example, molding, casting, or thermal forming polymer-solvent mixtures. In general, a polymer-solvent mixture is prepared without boiling and formed into a shape that is exposed to solvent-removal conditions that are controlled to make a nanoporous or microporous material using the guidance provided herein. An annealing process may be included. Hydrogels that are not microporous or nanoporous materials can also be made.

The heated polymeric mixture may be molded or otherwise formed as it is cooled or molded/formed and immediately cooled. Formed is a broad term that refers to passing the material from an amorphous melted state into an end-user product or an intermediate shape for further processing. Forming encompasses casting, layering, coating, injection molding, drawing, and extrusion. The forming can be done using an injection molding set up, where the mold consists of a material with thermal conductive properties allowing it to be heated easily to enhance the flow of the injected polymeric mixture, and to be cooled rapidly in a cooling environment. In other embodiments, the molding process can be accomplished by extrusion of the polymeric mixture through a die to form continuous material.

Cooling the polymeric mixture may comprise, e.g., cooling an extruded material, as in the case of passing the polymeric material through a die. An embodiment for cooling is a liquid bath at a temperature at least 20° C. cooler than the polymeric mixture boiling point or alternatively below the polymeric mixture Tm, e.g., 20, 30, 40, 50, 60, 70, 80, 90, 100, 110° C. below the boiling point or polymeric Tm, or alternatively the bath or other environment being at a temperature from −50 to 30° C.; Artisans will immediately appreciate that all ranges and values between the explicitly stated bounds are contemplated, with, e.g., any of the following being available as an upper or lower limit: −50, −45, −25, −20, −10, −5, −4, 0, 15, 20, 25, 30° C. The cooling may be performed in a solvent removing environment. Freezing temperatures may be avoided. Without being bound to a particular theory of operation, the polymer chains are cooled to the point of promoting intermolecular hydrogen binding and immobilizing chain movement. This may occur at temperatures as high as 30° C., or higher if time is allowed. The bath may be aqueous, and, by adjustment with salt or other osmotic agents, may be provided at an osmotic value to perform solvent removal on aqueous materials that are at a relatively lower osmotic value through osmotic pressure and diffusion. The bath may also be other solvents that freeze at temperatures lower than water, so that temperatures below 0° C. may be used without freezing the solvent or materials. In the event that hydrophilic copolymers are used in conjunction with PVA, for instance, temperatures higher than 20° C. may be used as crosslinking and chain immobilization will occur at much higher temperatures.

A solvent-removing environment refers to an environment that significantly accelerates removal of a solvent as compared to drying at ambient conditions. Such an environment may be non-heating, meaning it is not above ambient temperature, e.g., not above 20° C. Such an environment may be a vacuum, e.g., a vacuum chamber, a salt bath, or a bath that removes the solvent in the polymeric mixture. For instance, an aqueous polymeric mixture may be introduced into an ethanol bath, with the ethanol replacing the water. The ethanol may subsequently be removed. A salt bath may be, e.g., a high salt concentration bath (1M to 6M). A time of processing in a solvent-removing environment and/or a cooling process may be independently chosen to be from 1 to 240 hours; Artisans will immediately appreciate that all ranges and values between the explicitly stated bounds are contemplated, with, e.g., any of the following being available as an upper or lower limit: 1, 2, 5, 10, 24 hours, 1, 2, 5, 7, 10 days. Salts may be salts that dissociate to make single, double, or triply charged ions.

One or a plurality of solvent-removing environments may be used, or one environment may be adjusted with respect to temperature. Thus, a cooling bath may be used followed by solvent removal in an oven or vacuum oven. A washing step may be performed before or after cooling or solvent removal, e.g., by soaking in a series of solvents of varying concentrations, varying salt solutions, varying proportions of ethanol or other solvents.

An embodiment is an extruded material that has been through a solvent-removal process comprising exposure to a salt bath, the material is soaked in a series of H$_2$O baths (new baths or exchanged) for a period of time (e.g., 2-48 hours, 4-24 hours) to remove excess salt from the cast material or end-user device. The material is removed from the wash step and dehydrated to remove excess water. Dehydration can be done using, e.g., temperatures ranging from 20-95° C. Dehydration is generally performed at 37° C. for greater than 24 hours.

An embodiment is a polymeric mixture that has been extruded or otherwise formed that is then exposed to a high salt concentration bath (1M to 6M) for an inversely correlated period of time; high salt reduces the time required for soaking; for instance, it is soaked for 16-24 hours in a 6M solution of NaCl. After soaking, the material is rinsed free of salt solution. The material is now toughened and can be removed from any mold pieces carried over from the initial formation. Alternatively, after a salt or other bath, the material is soaked in water baths and dehydrated to remove excess water. Dehydration can be done using temps ranging from 20-95° C. Dehydration may be performed at 37° C. for greater than 4 hours, greater than 24 hours, or in a range from 2 to 150 hours; Artisans will immediately appreciate that all ranges and values between the explicitly stated bounds are contemplated, with, e.g., any of the following being available as an upper or lower limit: 2, 4, 6, 8, 10, 12, 16, 24, 48, 72, 96, 120, 144, 150 hours. For instance, dehydration at 40° C. for 6-24 hours has been observed to be useful.

In another embodiment, NaCl is incorporated into the starting polymeric solution at concentrations ranging from 0.1 to 3M of the final polymeric mixture volume. A polymer is dissolved in a heated solution under agitation, then brought above its melt point. To this solution, dry NaCl is added slowly under agitation until completely dissolved. The slightly hazy solution is then drawn into a feed for the purpose of creating a shape, either through injection molding, casting, extrusion and/or drawing. A quench is performed at the end of each process to rapidly reduce the temperature and form a solid material. In this embodiment, no additional salt soak is required. After material hardening, if necessary, the material is removed from any molding process parts and rinsed in water to remove salt and dehydrated.

The term annealing, as used in the context of a semi-crystalline polymer or a solid porous material refers to a heat treatment at an annealing temperature comparable to the melting temperature of the polymer or the polymers in the relevant material. This temperature is usually less than and is within about 0-15% of the melting temperature on an absolute temperature scale. Plasticizers or other additive materials may affect the melting temperature, usually by depressing it. For a pure PVA, for instance, the annealing temperature will be within about 10% of the melting point of the PVA; with other materials present, the annealing temperature will typically be lower. A theory of operation is that the annealing is a process that is a relaxation of stress combined with increase in the size of crystalline regions in the material being annealed. Unlike metals, annealing increases the strength of the annealed material. Annealing may be performed in one or more of: in air or in a gas or in an absence of oxygen or an absence of water, e.g., in nitrogen, in vacuum nitrogen, under argon, with oxygen scavengers, and so forth. For example, experiments have been made with annealing dehydrated PVA nanoporous materials. Annealing is utilized to increase crystallinity in the PVA network, further reducing pore sizes of the PVA network and to reduce adsorption properties of the final gel surface. Annealing can be done at temperatures ranging from, e.g., 100-200° C.; in a preferred embodiment, this step is performed submerging the dehydrated gel into a bath of mineral oil. Bulk incorporation of a polymer into a porous solid may also include an annealing process as already described above for a porous solid. Annealing may be performed after exposure of the desolvated porous solid to the mixture that has the polymers that are to be bulk incorporated. The Tg of the material may be raised or lowered dependent on the residual solvent content and/or presence of the bulk incorporated second hydrophilic polymer. As already described, the annealing process conditions may thus be adapted as to depend on temperature, time, ramp rate, and cooling rates of the substrate.

Annealing may be performed in a gas or a liquid at ambient, elevated, or low (vacuum) pressure. The liquid may be a low molecular weight polymer (up to 2000 Da) or other material (e.g., mineral oil). Examples of low molecular weight polymers are: silicone oils, glycerin, polyols, and polyethylene glycols of less than 500 Da. A useful embodiment is annealing in a bath of glycerin at, e.g., 140° C. for 1-3 hours; glycerin acts to further reduce fouling properties of the gel through interaction and neutralization of the free hydroxyl end groups of the PVA network. The annealed nanoporous material is allowed to cool, removed from the annealing bath and rinsed free of bath medium using a series of extended soaks. The product is then dehydrated to prepare for terminal sterilization.

Various types of dies may be used, e.g., longitudinal, angular, transverse and spiral extrusion heads, as well as single-polymer extrusion heads used for extruding a single polymer and multi layers extrusion heads used for simultaneous extrusion of a plurality of polymer layers or other layers. Continuous operation heads may be used, as well as cyclical. Various materials may be incorporated into, or as, a layer: for example, a reinforcing material, a fiber, a wire, a braided material, braided wire, braided plastic fibers, and so forth. Similarly, such materials may be excluded. Moreover, the porous solid may be made with a certain property, e.g., Young's modulus, tensile strength, solids content, polymer composition, porous structure, or solvent content that is known and thus measurable exclusive of various other materials. Accordingly, embodiments include materials disclosed herein that are described in terms of the materials' properties without regard to various other incorporated materials. For instance, a nanoporous solid has a certain Young's modulus that is known even if the material has a reinforcing wire that contributes further strength.

A core may be used with an extrusion die. The core may be air, water, a liquid, a solid, a non-solvent or a gas. Artisans reading this disclosure will appreciate that various extrusion processes using these various kinds of cores may be used. Cores made of polytetrafluoroethylene tubing (PTFE) are useful. In some embodiments, a core is a wire.

Multi lumen tubing has multiple channels running through its profile. These extrusions can be custom engineered to meet device designs. Multi Lumen tubing has a variable Outer Diameter (OD), numerous custom Inner Diameters (ID's), and various wall thicknesses. This tubing is available in a number of shapes; circular, oval, triangular, square, semi-circular, and crescent. These lumens can be used for guidewires, fluids, gases, wires, and various other needs. The number of lumens in multi lumen tubing is only limited by the size of the OD. In some embodiments, OD's are as large as 0.5 in., ID's can be as small as 0.002 in., and web and wall thicknesses can be as thin as 0.002 in. Tight tolerances can be maintained to +/−.0005 in. Artisans will immediately appreciate that all ranges and values between the explicitly stated bounds are contemplated, with, e.g., any of the following being available as an upper or lower limit for an OD and/or ID: 0.002, 0.003, 0.004, 0.007, 0.01, 0.02, 0.03, 0.04, 0.05, 0.1, 0.2, 0.3, 0.4, and 0.5 in. Tolerances may be, e.g., from 0.0005 to 0.1 in.; Artisans will immediately appreciate that all ranges and values between the explicitly stated bounds are contemplated, with, e.g., any of the following being available as an upper or lower limit: 0.0005, 0.001, 0.002, 0.003, 0.006, 0.01, 0.02, 0.03, 0.06, 0.8, 0.9, 1 in.

Braid reinforced tubing can be made in various configurations. For instance, it is possible to braid using round or flat, single or double ended wires as small as 0.001 in. Various materials can be used to make the braided reinforced tubing including stainless steel, beryllium copper, and silver, as well as monofilament polymers. The braid can be wound with various pics per inch over many thermoplastic substrates such as nylons or polyurethanes. The benefits of braided catheter shaft are its high torque-ability and kink resistance. By changing several factors during the braiding process, the characteristics of the tube can be altered to fit performance requirements. After braiding is complete, a second extrusion may be applied on top of the braided tube to encapsulate the braid and provide a smooth finish. Walls as thin as 0.007 in. can be achieved when a braid reinforced tube is required.

The porous solids such as the nanoporous materials, microporous materials, and strong hydrogels may be used to make catheters or medical fibers. These may be made with bulk incorporated polymers and may have the various features described for the same. Examples of catheters are central venous, peripheral central, midline, peripheral, tunneled, dialysis access, urinary, neurological, peritoneal, intra-aortic balloon pump, diagnostic, interventional, drug delivery, etc.), shunts, wound drains (external including ventricular, ventriculoperitoneal, and lumboperitoneal), and infusion ports. The porous solids may be used to make implantable devices, including fully implantable and percutaneously implanted, either permanent or temporary. The porous solid materials may be used to make blood-contacting devices or devices that contact bodily fluids, including ex vivo and/or in vivo devices, and including blood contacting implants. Examples of such devices drug delivery devices (e.g., insulin pump), tubing, contraceptive devices, feminine hygiene, endoscopes, grafts (including small diameter <6 mm), pacemakers, implantable cardioverter-defibrillators, cardiac resynchronization devices, cardiovascular device leads, ventricular assist devices, catheters (including cochlear implants, endotracheal tubes, tracheostomy tubes, drug delivery ports and tubing, implantable sensors (intravascular, transdermal, intracranial), ventilator pumps, and ophthalmic devices including drug delivery systems. Catheters can comprise a tubular nanoporous material with a fastener to cooperate with other devices, e.g., luer fasteners or fittings. Radiopaque agents may be added to the materials, fibers, or devices. The term radiopaque agent refers to agents commonly used in the medical device industry to add radiopacity to materials, e.g., barium sulfate, bismuth, or tungsten. RO agents may be incorporated at, e.g., from 5-50% w/w pf the total solids weight, e.g., 5, 10, 20, 30, 40, or 50%.

Medical fibers made with porous solid materials include applications such as sutures, yarns, medical textiles, braids, mesh, knitted or woven mesh, nonwoven fabrics, and devices based on the same. The fibers are strong and pliable. Materials may be made with these fibers so that they are resistant to fatigue and abrasion.

In an exemplary embodiment, the method comprises administering, into an external orifice of a subject, a polymeric material comprising a water-soluble polymer and having an aspect ratio of greater than or equal to 3:1, wherein administration of the article does not comprise the use of a sheath introducer. The polymeric material is substantially non-thrombogenic, the polymeric material has a water content of less than 5 w/w % and greater than or equal to 0.1 w/w % in the dehydrated state, and the polymeric material is configured to swell in an amount greater than or equal to 5 w/w % and less than or equal to 50 w/w % from a dehydrated state to an equilibrium water content state in less than or equal to 60 minutes.

EXAMPLES

Example 1

Samples of PVA extrusions were made by heating 200 g distilled water to 95° C. jacketed reaction vessel and allowed to heat to temperature. To this, 40 g of PVA (Sigma, 146 k-186 k) was added over 5 min time period while mixing at 200 RPM. Polymer was mixed for 1.5 hours at 300 RPM. Polymer was degassed at 90° C. for less than 2 hours. Polymer then extruded into −23° C. ethanol and then stored in ethanol at −25° C. in freezer for 24 hours. Samples were dried for 6 hours.

After drying, samples were submerged in 120° C. glycerol for 17 hours. After annealing, samples removed and allowed to cool before being rinsed with ethanol; cores removed after rinse. Samples dried for 12 hours at 50° C.

Samples of INA with barium sulfate were made by heating 50 g water in a jacketed reaction vessel at 90° C. In a side vessel, 4 g of barium sulfate and 50 g water homogenized for 15 minutes at 11 k RPM and then added to the jacketed vessel. This was mixed for 10 minutes to heat. After heating, 16 g of PVA (Sigma, 146 k-186 k) was added and mixed at 360 RPM for approximately 2 hours.

The PVA-RO polymer mixture was heated to 90° C. and extruded into −16° C. ethanol. The extrudate was allowed to dehydrate at −25° C. for 24 hours. Cores were removed and samples dried in an incubator at 50° C. for approximately 6 hours. After drying, samples were submerged in 120° C. glycerol (Sigma) for 17 hours. After annealing, samples removed and allowed to cool before being rinsed with distilled water. Samples dried at 50° C. for 12 hours and packaged for testing.

Samples were evaluated for non-thrombogenic durability testing at Thrombodyne, Inc. (Salt Lake City, UT). Each sample was cut to 15 cm in length with an N=5 per sample group. Prior to testing, samples were sterilized using a 12-hour ethylene oxide exposure; samples were hydra tested for approximately 48 hours in distilled water prior to evaluation to represent clinical use.

Fresh heparinized bovine blood with autologous $^{111}$In-labeled platelets was divided into portions for test sample and control evaluation. Samples were inserted into an in vitro blood flow loop of 0.25 in. ID polyvinyl chloride tubing for approximately 120 minutes. Blood was kept at 98° C. and pumped through the blood loop using a peristaltic pump for the duration of testing. Samples were initially checked for thrombi after 45 minutes in the blood flow loop and removed at 120 minutes. At the end of the experiment, the devices were explanted from the tubing, rinsed with saline, and placed in a gamma counter for thrombus quantification. Each experiment consisted of an independent flow system per test sample and/or control circulating blood from the same animal to enable simultaneous comparisons without cross-over effects.

Samples were measured for radioactivity and also qualitatively assessed for specific types of thrombus accumulation (i.e. adhesion or fibrin accumulation). Percent thrombosis was calculated relative to the average total thrombosis observed across all test and control groups per animal blood circulated Further Definitions The term medically acceptable refers to a material that is highly purified to be free of contaminants and is nontoxic. The term consists essentially of, as used in the context of a biomaterial or medical device, refers to a material or device that has no more than 3% w/w of other materials or components and said 3% does not make the device unsuited to intended medical uses. Equilibrium water content (EWC) is a term that refers to the water content of a material when the wet weight of the material has become constant, and before the material degrades. In general, materials with a high solids content have been observed to be at equilibrium water content at 24-48 hours. For purposes of measuring EWC, distilled water is used unless otherwise specified.

The term w/v refers to weight per volume e.g., g/L or mg/mL. The terms biomaterial and biomedical material are used interchangeably herein and encompass biomedically acceptable materials directed to a use in the biomedical arts, for example, as implants, catheters, blood-contacting materials, tissue-contacting materials, diagnostic assays, medical kits, tissue sample processing, or other medical purposes. Moreover, while the materials are suited for biomedical uses, they are not limited to the same and may be created as general-purpose materials. A physiological saline refers to a phosphate buffered solution with a pH of 7-7.4 and a human physiological osmolarity at 37° C.

The term molecular weight (MW) is measured in g/mol. The MW of a polymer refers to a weight average MW unless otherwise stated. When the polymer is part of a porous solid, the term MW refers to the polymer before it is crosslinked. When a distance between crosslinks is specified, it is the weight average MW between crosslinks unless otherwise indicated. The abbreviation k stands for thousand, M stands for million, and G stands for billion such that 50 k MW refers to 50,000 MW. Daltons is also a unit of MW and likewise refers to a weight average when used for a polymer.

Publications, journal articles, patents and patent applications referenced herein are hereby incorporated herein for all purposes, with the instant specification controlling in case of conflict. Features of embodiments set forth herein may be mixed and matched as guided by the need to make an operable process or product.

As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition.

As used herein, when a component is referred to as being "adjacent" another component, it can be directly adjacent to (e.g., in contact with) the component, or one or more intervening components also may be present. A component that is "directly adjacent" another component means that no intervening component(s) is present.

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the self-righting article. As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. An article, comprising:
   a catheter comprising a tube, the tube having a plurality of markings;
   wherein the plurality of markings comprise multiple separate segments spaced along at least a portion of a surface of the tube;
   wherein the article has a first configuration having a first water content greater than or equal to 2 w/w % and less than or equal to 40 w/w %, and wherein an average shortest distance between each segment and a nearest neighbor segment in the first configuration is a first distance;
   wherein the article has a second configuration having a second water content greater than or equal to 20 w/w % and less than or equal to 99 w/w %, wherein the average shortest distance between each segment and the nearest neighbor segment in the second configuration is a second distance;
   wherein the second water content is greater than the first water content; and wherein a ratio of the second distance to the first distance is greater than or equal to 1.02:1.

2. An article, comprising:
a catheter comprising a tube, the tube having a plurality of markings;
wherein the plurality of markings comprise multiple separate segments spaced along at least a portion of a surface of the tube;
wherein the article has a first configuration having a first water content greater than or equal to 2 w/w % and less than or equal to 40 w/w %, and wherein an average shortest distance between each segment and a nearest neighbor segment in the first configuration is a first distance;
wherein the article has a second configuration having a second water water content greater than or equal to 20 w/w % and less than or equal to 99 w/w %, wherein the average shortest distance between each segment and the nearest neighbor segment in the second configuration is a second distance;
wherein the second water content is greater than the first water content, and
wherein the second distance is equal to about 1 mm, about 10 mm, about 100 mm, about 1 cm, or about 10 cm.

3. The article of claim 2, wherein the second configuration is at equilibrium water content of the catheter.

4. The article of claim 2, wherein the catheter comprises a first water-soluble polymer.

5. The article of claim 4, wherein the first water-soluble polymer comprises poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(Nisopropylacrylamide), poly(2-hydroxymethylmethacrylate), and combinations thereof.

6. The article of claim 4, wherein the plurality of markings comprise a second water-soluble polymer and a dye.

7. The article of claim 6, wherein the first water-soluble polymer and the second water-soluble polymer are different.

8. The article of claim 6, wherein the first water-soluble polymer and the second water-soluble polymer are the same.

9. The article of claim 6, wherein the dye comprises a compound selected from the group consisting of tetrasodium;4-amino-5-hydroxy-3,6-bis[[4-(2-sulfonatooxyethylsulfonyl)phenyl]diazenyl]naphthalene-2,7-disulfonate (Reactive Black 5), copper;33-[[4-(2-hydroxyethylsulfonyl)phenyl]sulfamoyl]-2,11,20,29,39,40-hexaza-37,38-diazanidanonacyclo[28.6.1.13,10.112,19.121,28.04,9.013,18.022,27.031,36]tetraconta-1,3(40),4(9),5,7,10,12(39),13 (18),14,16,19,21,23,25,27,29,31(36),32,34-nonadecaene-6,15,24-trisulfonic acid (Reactive Blue 21), 2-Naphthalenesulfonicacid,7-(acetylamino)-4-hydroxy-3-[[4-[[2-(sulfooxy)ethyl]sulfonyl]phenyl]azo]-,disodium salt (9CI) (Reactive Orange 78), Reactive Yellow 15, Disodium 1-amino-9,10-dioxo-4-[(3-{[2-(sulfonatooxy)ethyl]sulfonyl}phenyl)amino]-9,10-dihydro-2-anthracenesulfonate (Reactive Blue 19), 1-Amino-4-[3-(4,6-dichloro-triazin-2-ylamino)-4-sulfophenylamino]anthraquinone-2-sulfonic acid (Reactive Blue 4), C.I. Reactive Red 11, 4-[2-(5-carbamoyl-1-ethyl-4-methyl-2,6-dioxopyridin-3-ylidene)hydrazinyl]-6-[(4,6-dichloro-1,3,5-triazin-2-yl) amino]benzene-1,3-disulfonate (C.I. Reactive Yellow 86), Tetrasodium 6,13-dichloro-3,10-bis [[4-[(4,6-dichloro-1,3,5-triazin-2-yl) amino] sulphonatophenyl] amino] triphenodioxazinedisulphonate (C.I. Reactive Blue 163), and/or 5-(benzoylamino)-4-hydroxy-3-[[1-sulfo-6-[[2-(sulfooxy) ethyl]sulfonyl]-2-naphthalenyl]azo]-, tetrasodium salt (C.I. Reactive Red 180).

10. The article of claim 6, wherein the second water-soluble polymer comprises poly(vinyl alcohol), poly(acrylic acid), polyethylene glycol, poly(vinyl pyrrolidone), poly (methacrylic sulfobetaine), poly(acrylic sulfobetaine), poly (methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(Nisopropylacrylamide), poly(2-hydroxymethylmethacrylate), and combinations thereof.

11. The article of claim 2, wherein the plurality of markings further comprise a salt.

12. The article of claim 11, wherein the salt comprises an agent selected from the group consisting of phosphates (e.g., MSP, DSP, TSP), borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

13. The article of claim 2,
wherein at least a portion of the plurality of markings penetrate into the tube of the catheter at a depth of between 10 μm to 10 mm.

14. The article of claim 2, wherein the catheter is selected from the group consisting of central venous catheters, peripheral central catheters, midline catheters, peripheral catheters, peripheral port catheters, central venous port catheters, tunneled catheters, dialysis access catheters, urinary catheters, neurological catheters, percutaneous transluminal angioplasty catheters, and peritoneal catheters.

15. The article of claim 2, wherein the plurality of markings do not crack or delaminate when the catheter is swelled from the first configuration to the second configuration.

\* \* \* \* \*